(12) United States Patent
Hirschman et al.

(10) Patent No.: US 10,016,618 B2
(45) Date of Patent: *Jul. 10, 2018

(54) METHODS AND SYSTEMS FOR INTEGRATED RADIOPHARMACEUTICAL GENERATION, PREPARATION, TRANSPORTATION AND ADMINISTRATION

(71) Applicant: BAYER HEALTHCARE LLC, Indianola, PA (US)

(72) Inventors: Alan D. Hirschman, Glenshaw, PA (US); Arthur E. Uber, III, Pittsburgh, PA (US); David M. Reilly, Pittsburgh, PA (US); John F. Kalafut, Pittsburgh, PA (US); Frederick W. Trombley, III, Gibsonia, PA (US); Steven J. Remis, Ford City, PA (US); Scott Griffith, Murrysville, PA (US); Douglas Descalzi, Pittsburgh, PA (US); Richard Dewit, Mt Lebanon, PA (US); David M. Griffiths, Pittsburgh, PA (US); Marc A. Mabie, Gibsonia, PA (US); Mark Trocki, Cheswick, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 301 days.

This patent is subject to a terminal disclaimer.

(21) Appl. No.: 15/142,000

(22) Filed: Apr. 29, 2016

(65) Prior Publication Data

US 2016/0303397 A1    Oct. 20, 2016

Related U.S. Application Data

(63) Continuation of application No. 12/595,165, filed as application No. PCT/US2007/089101 on Dec. 28, 2007, now Pat. No. 9,326,742.

(Continued)

(51) Int. Cl.
*A61B 6/00* (2006.01)
*A61M 36/06* (2006.01)
(Continued)

(52) U.S. Cl.
CPC ............ *A61N 5/1001* (2013.01); *A61B 5/055* (2013.01); *A61B 6/032* (2013.01); *A61B 6/037* (2013.01);
(Continued)

(58) Field of Classification Search
CPC ....... A61B 5/0205; A61B 6/508; A61B 6/037; A61B 6/0478; A61B 6/4057;
(Continued)

(56) References Cited

U.S. PATENT DOCUMENTS 3,718,138 A    2/1973  Alexandrov et al.
3,984,695 A    10/1976 Collica et al.
(Continued)

FOREIGN PATENT DOCUMENTS

EP    1616587 A1    1/2006
GB    2228168 A     8/1990
(Continued)

OTHER PUBLICATIONS

Office Action dated Dec. 2, 2014 from related U.S. Appl. No. 13/789,535.
(Continued)

*Primary Examiner* — Christine H Matthews
*Assistant Examiner* — Joshua D Lannu
(74) *Attorney, Agent, or Firm* — Joseph L. Kent; David Schramm; James R. Stevenson

(57) ABSTRACT

An integrated radiopharmaceutical patient treatment system is disclosed including a patient support platform with an associated patient stimulus apparatus, an imager proximate the patient support platform, a radiopharmaceutical fluid
(Continued)

delivery system for infusing a radiopharmaceutical fluid into a patient, a patient monitor to be associated with a patient, and an integrated system controller operably associated with the patient stimulus apparatus, imager, radiopharmaceutical fluid delivery system, and patient monitor to control and coordinate their operations. Within the patient treatment system the radiopharmaceutical fluid delivery system may be included comprising a radionuclide supply module, a radiopharmaceutical processing module, a quality control module, a patient injection module, and a controller. A hazardous fluid handling system including a docking station and a hazardous fluid transport device adapted to detachably dock with the docking station is further disclosed.

20 Claims, 35 Drawing Sheets

Related U.S. Application Data

(60) Provisional application No. 60/910,810, filed on Apr. 9, 2007, provisional application No. 60/878,334, filed on Jan. 1, 2007, provisional application No. 60/878,333, filed on Jan. 1, 2007.

(51) Int. Cl.

| | | |
|---|---|---|
| *A61M 36/08* | (2006.01) | |
| *A61N 5/10* | (2006.01) | |
| *A61B 6/03* | (2006.01) | |
| *A61B 6/04* | (2006.01) | |
| *A61M 5/172* | (2006.01) | |
| *G06F 19/00* | (2018.01) | |
| *G21G 4/08* | (2006.01) | |
| *A61B 6/10* | (2006.01) | |
| *A61B 5/055* | (2006.01) | |
| *G21F 5/015* | (2006.01) | |
| *A61B 5/0205* | (2006.01) | |
| *A61B 5/00* | (2006.01) | |
| *A61M 5/00* | (2006.01) | |
| *A61M 5/145* | (2006.01) | |
| *A61M 5/168* | (2006.01) | |
| *A61M 5/178* | (2006.01) | |

(52) U.S. Cl.
CPC ........... *A61B 6/0478* (2013.01); *A61B 6/107* (2013.01); *A61B 6/4057* (2013.01); *A61B 6/4258* (2013.01); *A61B 6/4423* (2013.01); *A61M 5/16881* (2013.01); *A61M 5/1723* (2013.01); *A61N 5/1071* (2013.01); *G06F 19/3468* (2013.01); *G21F 5/015* (2013.01); *G21G 4/08* (2013.01); *A61B 5/0205* (2013.01); *A61B 5/7289* (2013.01); *A61B 6/507* (2013.01); *A61B 6/508* (2013.01); *A61B 6/5288* (2013.01); *A61B 6/548* (2013.01); *A61M 5/007* (2013.01); *A61M 5/1456* (2013.01); *A61M 5/14546* (2013.01); *A61M 5/16827* (2013.01); *A61M 5/1785* (2013.01); *A61M 2205/3576* (2013.01); *A61N 2005/1021* (2013.01); *A61N 2005/1094* (2013.01)

(58) Field of Classification Search
CPC ..... A61B 6/4258; A61B 6/5288; A61B 6/107; A61B 6/4423; A61B 6/548; A61B 6/507; A61B 5/7289; A61M 5/007; A61M 5/14546; A61M 5/1456; A61M 5/16827; A61M 5/16881; A61M 5/1723; A61M 5/1785; A61M 2205/3576; G06F 19/3468; G21G 4/08

See application file for complete search history.

(56) References Cited

U.S. PATENT DOCUMENTS

| | | |
|---|---|---|
| 4,084,097 A | 4/1978 | Czaplinski et al. |
| 4,092,546 A | 5/1978 | Larrabee |
| 4,207,889 A | 6/1980 | Buehring et al. |
| 4,307,713 A | 12/1981 | Galkin et al. |
| 4,401,108 A | 8/1983 | Galkin et al. |
| 4,409,966 A | 10/1983 | Lambrecht et al. |
| 4,472,403 A | 9/1984 | Trijzelaar et al. |
| 4,562,829 A | 1/1986 | Bergner |
| 4,585,009 A | 4/1986 | Barker et al. |
| 4,585,941 A | 4/1986 | Bergner |
| 4,632,123 A | 12/1986 | Govaert et al. |
| 4,804,847 A | 2/1989 | Uber, III |
| 4,837,110 A | 6/1989 | Kuhlmann et al. |
| 4,838,856 A | 6/1989 | Mulreany et al. |
| 4,857,728 A | 8/1989 | Smith, Jr. |
| 5,039,863 A | 8/1991 | Matsuno et al. |
| 5,274,239 A | 12/1993 | Lane et al. |
| 5,415,843 A | 5/1995 | Andersson |
| 5,472,403 A | 12/1995 | Cornacchia et al. |
| 5,514,071 A | 5/1996 | Sielaff, Jr. et al. |
| 5,523,578 A | 6/1996 | Herskovic |
| 5,569,181 A | 10/1996 | Heilman et al. |
| 5,733,259 A | 3/1998 | Valcke et al. |
| 5,739,508 A | 4/1998 | Uber, III |
| 5,806,519 A | 9/1998 | Evans, III et al. |
| 5,840,026 A | 11/1998 | Uber, III et al. |
| 5,843,037 A | 12/1998 | Uber, III |
| 5,927,351 A | 7/1999 | Zhu et al. |
| 5,967,983 A | 10/1999 | Ashburn |
| 6,162,198 A | 12/2000 | Coffey et al. |
| 6,180,082 B1 | 1/2001 | Woltering et al. |
| 6,397,098 B1 | 5/2002 | Uber, III et al. |
| 6,425,174 B1 | 7/2002 | Reich |
| 6,542,751 B1 | 4/2003 | Blink et al. |
| 6,572,823 B1 | 6/2003 | Donahue et al. |
| 6,589,158 B2 | 7/2003 | Winkler |
| 6,767,319 B2 | 7/2004 | Reilly et al. |
| 6,773,673 B1 | 8/2004 | Layfield et al. |
| 6,970,735 B2 | 11/2005 | Uber et al. |
| 7,105,846 B2 | 9/2006 | Eguchi |
| 7,151,267 B2 | 12/2006 | Lemer |
| 7,163,031 B2 | 1/2007 | Graves et al. |
| 7,169,135 B2 | 1/2007 | Duchon et al. |
| 7,618,397 B2 | 11/2009 | Hicks |
| 7,672,710 B2 | 3/2010 | Uber, III |
| 7,734,331 B2 | 6/2010 | Dhawale et al. |
| 8,071,959 B2 | 12/2011 | Dekemp |
| 8,198,599 B2 | 6/2012 | Bouton et al. |
| 2003/0212707 A1 | 11/2003 | Uber et al. |
| 2004/0015038 A1 | 1/2004 | Lemer |
| 2004/0086437 A1 | 5/2004 | Jackson |
| 2004/0176676 A1 | 9/2004 | Graw |
| 2004/0254525 A1 | 12/2004 | Uber et al. |
| 2004/0254533 A1 | 12/2004 | Schriver et al. |
| 2004/0258615 A1 | 12/2004 | Buchanan et al. |
| 2005/0085682 A1 | 4/2005 | Sasaki et al. |
| 2005/0107698 A1 | 5/2005 | Powers et al. |
| 2005/0177239 A1 | 8/2005 | Steinberg |
| 2005/0203329 A1 | 9/2005 | Muto et al. |
| 2005/0203330 A1 | 9/2005 | Muto et al. |
| 2005/0226776 A1 | 10/2005 | Brady et al. |
| 2005/0232387 A1 | 10/2005 | Padgett et al. |
| 2005/0238576 A1 | 10/2005 | Dell et al. |
| 2005/0277833 A1 | 12/2005 | Williams |
| 2006/0004243 A1 | 1/2006 | Shimizu et al. |
| 2006/0151048 A1 | 7/2006 | Tochon-Danguy et al. |
| 2006/0188407 A1* | 8/2006 | Gable .................. A61B 5/0084 604/19 |
| 2008/0177126 A1 | 7/2008 | Tate et al. |
| 2008/0242915 A1 | 10/2008 | Jackson et al. |

(56) References Cited

U.S. PATENT DOCUMENTS

| | | |
|---|---|---|
| 2009/0131862 A1 | 5/2009 | Buck et al. |
| 2009/0177050 A1 | 7/2009 | Griffiths et al. |
| 2009/0312695 A1 | 12/2009 | Wilson et al. |
| 2011/0152679 A1 | 6/2011 | Morag |
| 2012/0016174 A1 | 1/2012 | De Taboada et al. |

FOREIGN PATENT DOCUMENTS

| | | | |
|---|---|---|---|
| JP | 2000350783 | A | 12/2000 |
| JP | 2002306609 | A | 10/2002 |
| JP | 2004290455 | A | 10/2004 |
| JP | 2005230366 | A | 9/2005 |
| JP | 2006015055 | A | 1/2006 |
| JP | 2006017660 | A | 1/2006 |
| JP | 2006132984 | A | 5/2006 |
| JP | 2006133139 | A | 5/2006 |
| JP | 2006283431 | A | 10/2006 |
| WO | 2004004787 | A2 | 1/2004 |
| WO | 2006051531 | A2 | 5/2006 |
| WO | 2006108026 | A2 | 10/2006 |
| WO | 2006129301 | A2 | 12/2006 |
| WO | 2007010534 | A2 | 1/2007 |

OTHER PUBLICATIONS

The Final Office Action dated Apr. 1, 2015 from related U.S. Appl. No. 13/789,535.

The Non-Final Office Action dated May 15, 2015 from related U.S. Appl. No. 12/595,165.

Feichtinger, M., et al., "Automatic and remote controlled ictal SPECT injection for seizure focus localization by use of a commercial contrast agent application pump," Epilepsia, vol. 48, Issue 7, pp. 1409-1413 (Jul. 2007).

Final Office Action dated Jun. 5, 2014 from related U.S. Appl. No. 12/595,165.

Lee, J. J., et al., "Ictal SPECT using an Attachable Automated Injector: Clinical Usefulness in the Prediction of Ictal Onset Zone," Acta Radiological, vol. 50, Issue 10, pp. 1160-1168 (Dec. 2009).

Non-Final Office Action dated Oct. 18, 2013, Non-Final Office Action dated Dec. 31, 2012 and Final Office Action dated Jun. 17, 2013 from related U.S. Appl. No. 12/595,165.

\* cited by examiner

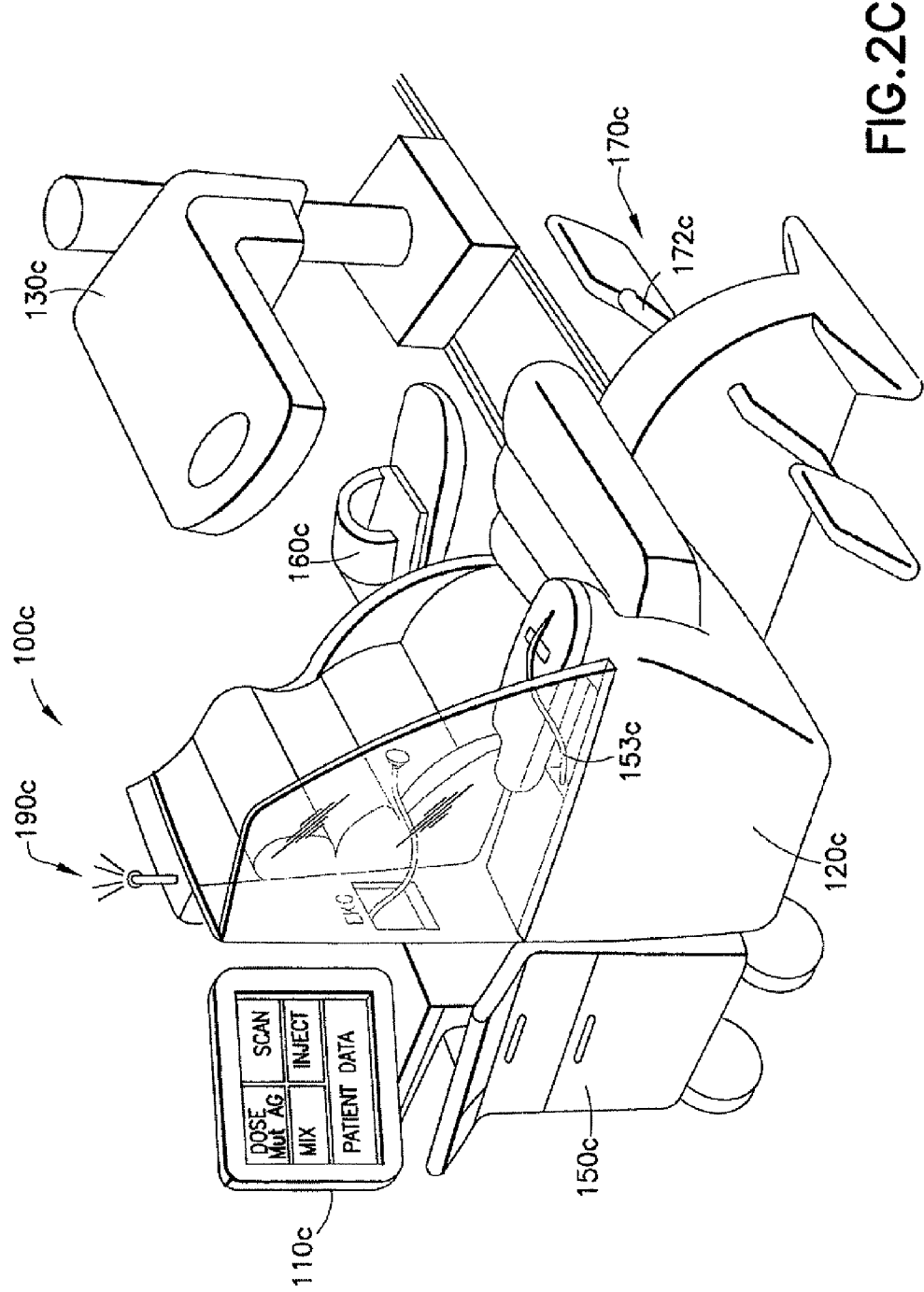

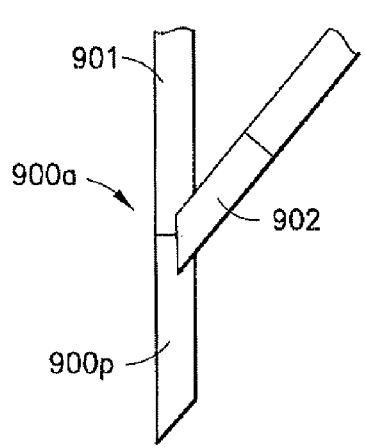
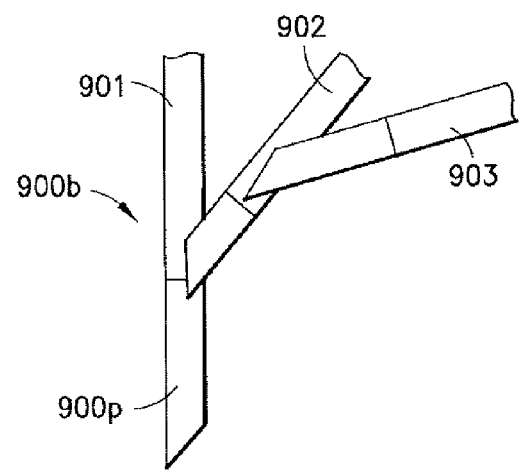
FIG.8     FIG.9
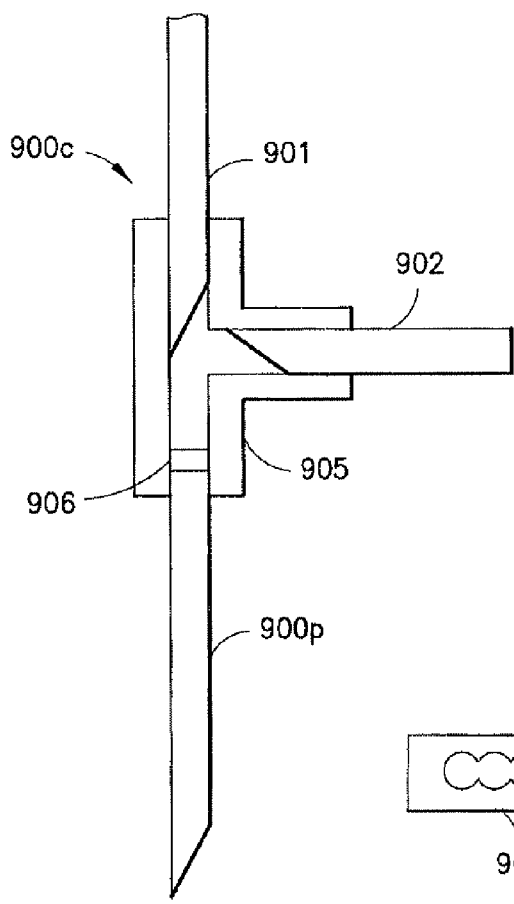
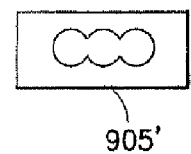
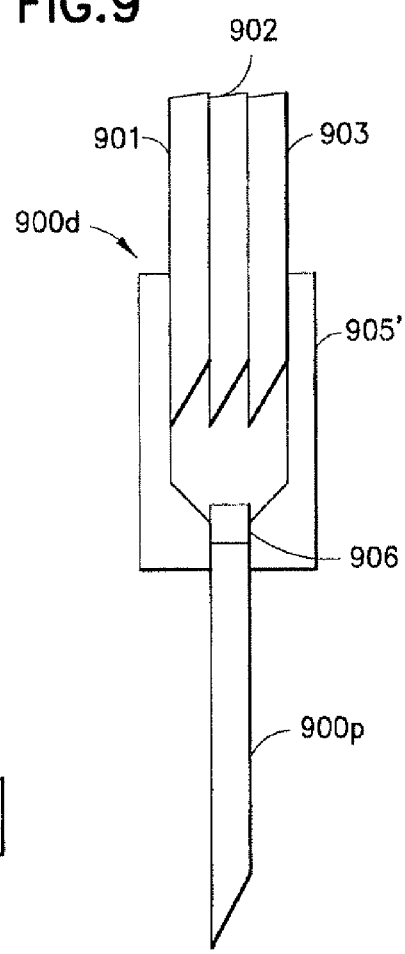
FIG.10     FIG.12     FIG.11

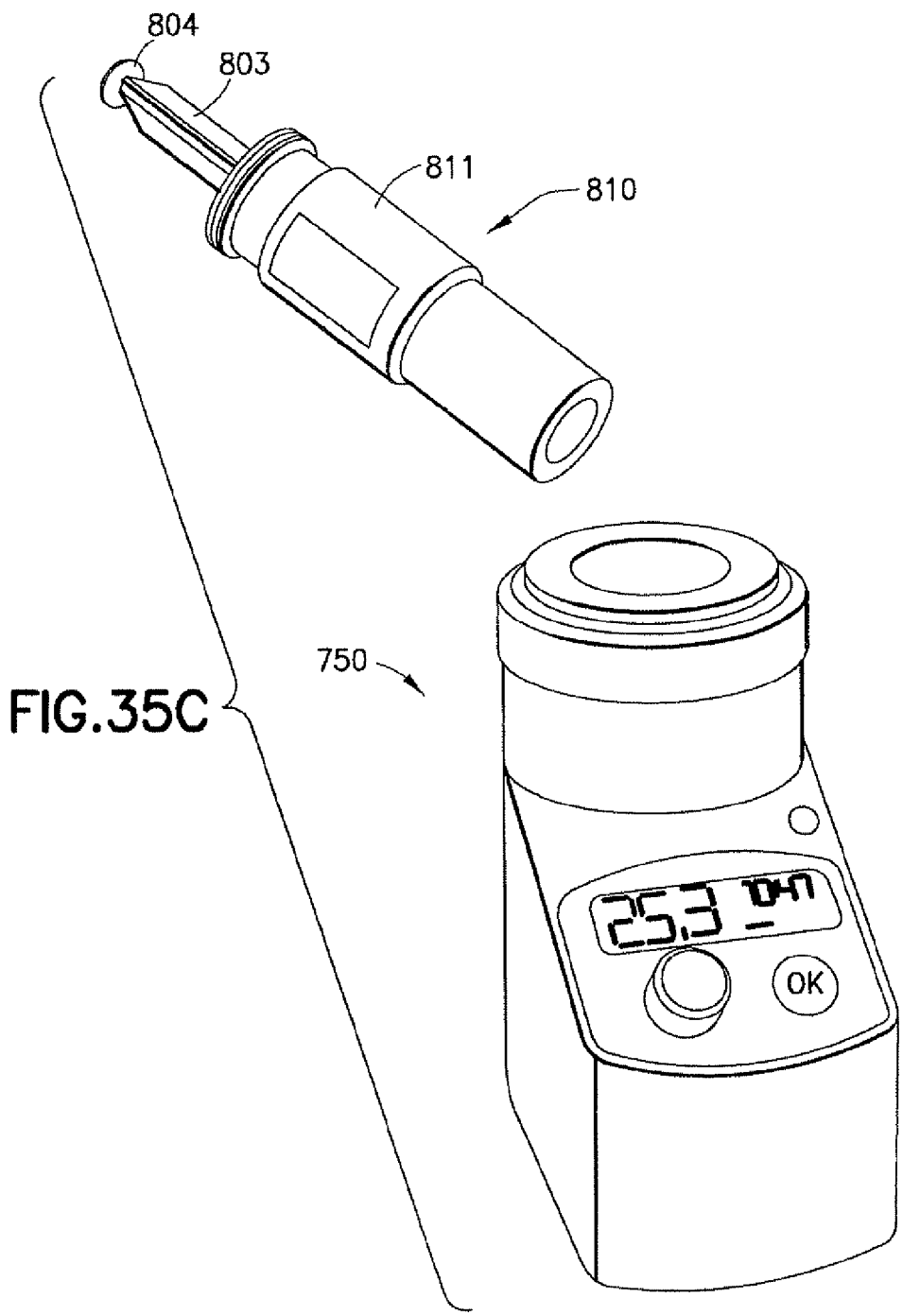

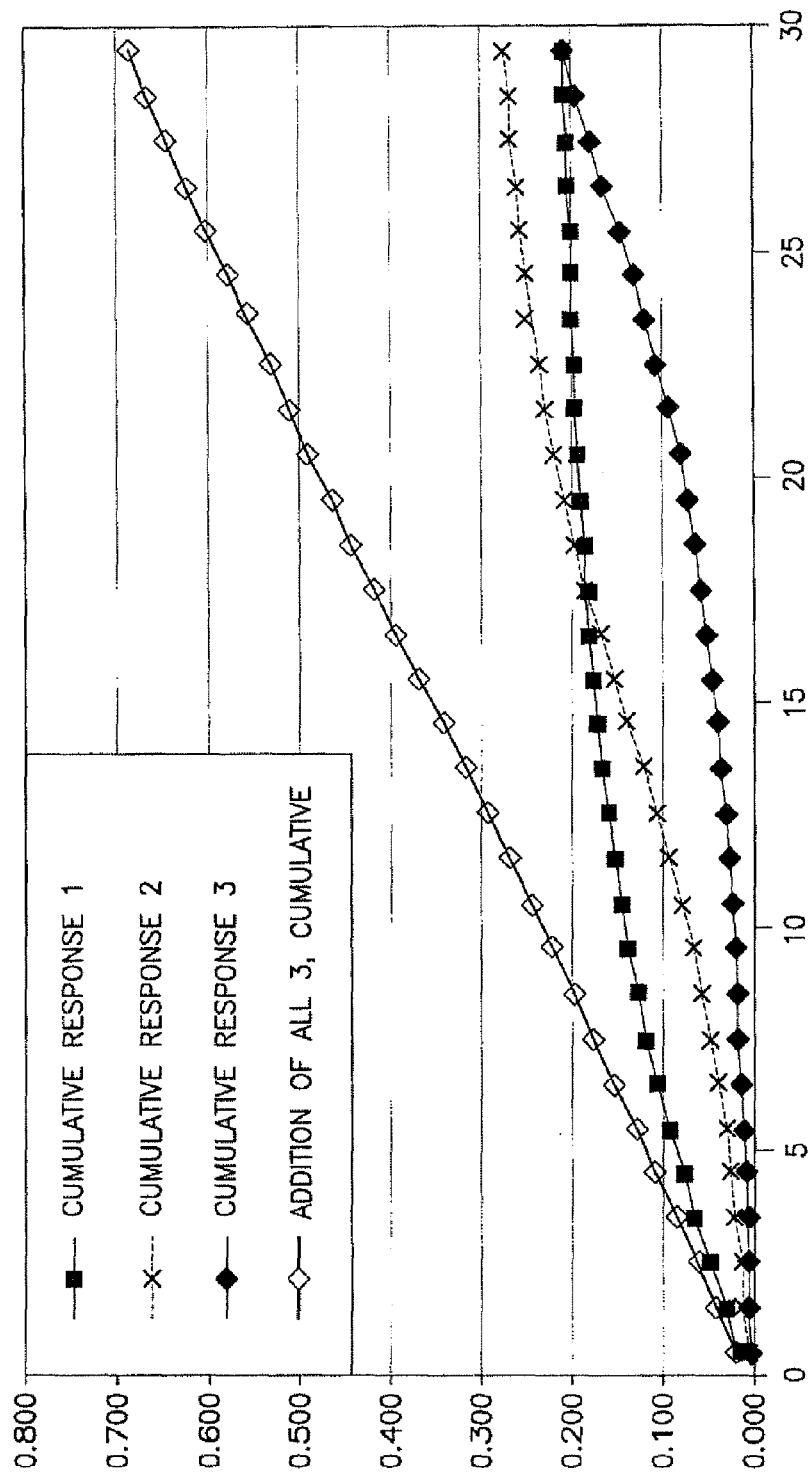

METHODS AND SYSTEMS FOR INTEGRATED RADIOPHARMACEUTICAL GENERATION, PREPARATION, TRANSPORTATION AND ADMINISTRATION

CROSS REFERENCE TO RELATED APPLICATIONS

This application is a Divisional application of U.S. Ser. No. 12/595,165, filed Jan. 20, 2011, now U.S. Pat. No. 9,326,742, which is a 371 U.S. national phase application of PCT International Application No. PCT/US 2007/089101, filed Dec. 28, 2007, and designating the United States, which claims the benefit of United States Provisional Patent Application No. 60/910,810 entitled "Methods and Systems for Integrated Radiopharmaceutical Generation, Preparation, and Administration" filed Apr. 9, 2007 and, further, claims the benefit of United States Provisional Patent Application No. 60/878,334 entitled "Methods and Equipment for Handling Radiopharmaceuticals" and United States Provisional Patent Application No. 60/878,333 entitled "Pharmaceutical Dosing Method", both filed Jan. 1, 2007, the disclosures of each of which are incorporated herein by this reference.

BACKGROUND OF THE INVENTION

Field of the Invention

The invention disclosed herein relates to generation, preparation, and administration of pharmaceutical substances, typically intrinsically harmful or toxic pharmaceutical substances such as radioactive pharmaceutical substances, generally known as radiopharmaceuticals to human and animal subjects and, more specifically, to methods and systems and associated components for the generation, preparation, transportation, and administration of fluid radiopharmaceutical substances to human and animal subjects. The non-radiation shielding aspects of the various embodiments presented herein are applicable to all medical fluid applications involving the preparation and delivery/administration of such non-radioactive medical fluids.

Description of Related Art

Administration of radioactive pharmaceutical substances or drugs, generally termed radiopharmaceuticals, is often used in the medical field to provide information or imagery of internal body structures and/or functions including, but not limited to, bone, vasculature, organs and organ systems, and other tissue. Additionally, such radiopharmaceuticals may be used as therapeutic agents to kill or inhibit the growth of targeted cells or tissue, such as cancer cells. However, radiopharmaceutical agents used in imaging procedures and therapeutic procedures typically include highly radioactive nuclides of short half-lives and are hazardous to attending medical personnel. These agents are toxic and can have physical and/or chemical effects for attending medical personnel such as clinicians, imaging technicians, nurses, and pharmacists. Excessive radiation exposure is harmful to attending medical personnel due to their occupational repeated exposure to the radiopharmaceuticals. However, due to the short half-life of typical radiopharmaceutical agents and small applied dosages, the radiation exposure risk to benefit ratio for individual patients is acceptable. The constant and repeated exposure of medical personnel to radiopharmaceuticals over an extended period of time is a significant problem in the nuclear medicine field.

A number of techniques are used in the medical field to reduce radiation exposure to attending medical personnel associated with the creation, handling, transport, dose preparation, and administration of radiopharmaceuticals to patients. These techniques encompass one or more of minimizing the time of exposure of medical personnel, maintaining distance between medical personnel and the source of radiation, and/or shielding medical personnel from the source of radiation. As a certain amount of close-proximity interfacing between medical personnel and radiopharmaceutical agents (including patients who have or are to receive radiopharmaceutical agents) is somewhat inevitable during the current practice of generating, preparing, and administering radiopharmaceutical agents to patients and caring for these patients, radiation shielding has considerable importance in the nuclear medicine field. A simple patient radiation guard is disclosed in U.S. Pat. No. 3,984,695 to Collica et al. as an example. It is well-known, for example, to use shielded containers known as "pigs" for general handling and transport of radiopharmaceutical containers (bottles, vials, etc.) and use shielded syringes to remove the radiopharmaceutical from the radiopharmaceutical containers and administer the same to individual patients. Radiopharmaceutical transport pigs are also configured to transport syringes. Examples of shielded transport pigs are disclosed in U.S. Pat. No. 5,274,239 to Lane et al. which is incorporated by reference and U.S. Pat. No. 6,425,174 to Reich, also incorporated herein by reference. An example of a shielded syringe is disclosed in U.S. Pat. No. 4,307,713 to Galkin et al. which is also incorporated herein by reference. Other shielded syringes are known from U.S. Pat. No. 6,589,158 to Winkler; United States Patent Application Publication No. 2004/0015038 to Lemer; and U.S. Pat. No. 6,162,198 to Coffey et al., all incorporated herein by reference.

As is generally known in the nuclear medicine field, radiation emanates in all directions from radioactive substances and, consequently, emanates in all directions from an unshielded container holding a radioactive substance. While radiation may be scattered or deflected, this effect is generally small enough that it is sufficient to protect personnel from the direct "shine" of radiation and not be too concerned with scattered radiation, unless the activity levels in the container are very high. Transport pigs come in various configurations for holding radiopharmaceutical containers (bottles, vials, syringes, etc.). One form often includes a removable cover that allows access to the held radiopharmaceutical container, as disclosed in United States Patent Application Publication No. 2005/0107698 to Powers et al. incorporated herein by reference. Such containers may be in the form of a vial with an elastomeric, for example, rubber, stopper, or septum which retains the radiopharmaceutical agent in the vial. When the pig cover is in place, the radiation exposure is acceptable. When the cover is opened or removed, a radiation "shine" emanates from the opening. A common sterile transfer procedure to remove the radiopharmaceutical agent from its container is to pierce the elastomeric stopper or septum with a sterile needle on a syringe. Commonly, the exposed surface of the stopper or septum is sterilized with an alcohol wipe prior to piercing the stopper or septum with the transfer needle on the syringe.

Syringes, during loading and once loaded with radiopharmaceutical agents, are commonly handled via syringe shields and shielded glove boxes or containers, but may also be transported in a suitably configured transport pig as noted previously. Syringe shields are commonly hollow cylindrical structures that accommodate the cylindrical body of the syringe and are constructed of lead or tungsten with a lead glass window that allows the handler to view the syringe plunger and liquid volume within the syringe. Due to its cylindrical configuration, syringe shields protect against radiation emissions in a generally radial direction along the length of the syringe body but the two open ends of the syringe shield provide no protection to the handler as there is radiation "shine" emanating from the two ends of the syringe shield. Devices are further known for drawing radiopharmaceutical agents into syringes. For example, U.S. Pat. No. 5,927,351 to Zhu et al. discloses a drawing station for handling radiopharmaceuticals for use in syringes, incorporated herein by reference. In radiopharmaceutical delivery applications, devices are known for remotely administering radioactive substances from syringes to minimize radiation exposures to attending medical personnel as disclosed in U.S. Pat. No. 5,514,071 to Sielaff Jr. et al. or U.S. Pat. No. 3,718,138 to Alexandrov et al. An automated device for controlled administering radioactive substances is disclosed in U.S. Pat. No. 5,472,403 to Cornacchia et al. and is incorporated herein by reference. A system approach to controlling injectors used to inject radioactive material into a patient is disclosed in published German Document No. DE 10 2005 010152.

In addition to the difficulties introduced by the hazardous nature of radiopharmaceuticals, the short half-lives of such radiopharmaceuticals further complicate the administration of a proper dosage to a patient. The radioactivity levels of the radiopharmaceutical agents used as tracers in, for instance, single-photon emission computerized tomography (SPECT) and positron emission tomography (PET) imaging procedures are measured by medical personnel, such as radio-pharmacists or nuclear medicine technologists, to determine the radiation dose that will be administered to the individual during the course of a diagnostic procedure. The radiation dose received depends on a number of factors including the half-life of the radiopharmaceutical agent and the initial radioactivity level of the radiopharmaceutical agent at the time it is injected into the individual. One known solution is to measure or calibrate the initial radioactivity of the radiopharmaceutical and time the injection so that a dose of the desired level of radioactivity is delivered (as calculated from the half-life of the radiopharmaceutical). Often, radiation levels are determined as part of the dispensing or container filling process as disclosed generally in United States Patent Application Publication No. 2006/0151048 to Tochon-Ganguy et al. or measured by a stand-alone device adapted to receive the radiopharmaceutical container as disclosed in U.S. Pat. No. 7,151,267 to Lemer or U.S. Pat. No. 7,105,846 to Eguchi. Radiation detectors have also been placed upon syringe shields and in-line with the radiopharmaceutical delivery system. For example, U.S. Pat. No. 4,401,108 to Galkin et al. discloses a syringe shield for use during drawing, calibration, and injection of radiopharmaceuticals. This syringe shield includes a radiation detector for detecting and calibrating the radioactive dosage of the radiopharmaceutical drawn into the syringe. A similar arrangement to that disclosed by Galkin et al. but in connection with a transport pig is disclosed in Japanese Publication No. JP2005-283431, assigned to Sumitomo Heavy Industries. U.S. Pat. Nos. 4,562,829 and 4,585,009 to Bergner and Barker et al., respectively, and incorporated herein by reference disclose strontium-rubidium infusion systems and a dosimetry system for use therein. The infusion system includes a generator of the strontium-rubidium radiopharmaceutical in fluid connection with a syringe used to supply pressurized saline. Saline pumped through the strontium-rubidium generator exits the generator either to the patient or to waste collection. Tubing in line between the generator and the patient passes in front of a dosimetry probe to count the number of disintegrations that occur. As the geometric efficiency (or calibration) of the detector, the flow rate through the tubing, and volume of the tubing is known, it is possible to measure the total activity delivered to the patient (for example, in milliCuries) Likewise, radiation measurements have been made upon blood flowing through the patient. For example, U.S. Pat. No. 4,409,966 to Lambrecht et al. discloses shunting of blood flow from a patient through a radiation detector. A significant quantity of information about nuclear medicine imaging devices and procedures can be found in WO 2006/651531 A2 and WO 2007/010534 A2 from Spectrum Dynamics LLC., incorporated herein by reference. A portable fluid delivery unit is known from U.S. Pat. No. 6,773,673 to Layfield et al., incorporated herein by reference.

As noted above, examples of the use of radiopharmaceutical agents in diagnostic imaging procedures include positron emission tomography (PET) and single-photon emission computerized tomography (SPECT) which are noninvasive, three-dimensional imaging procedures that provide information regarding physiological and biochemical processes in patients. In effect, the radiopharmaceutical agent acts as a tracer to interact with the targeted area. An initial step in producing PET images or SPECT images of, for example, vasculature, organs and organ systems, and/or other targeted tissue is to inject the patient with a dose of the radiopharmaceutical agent. The radiopharmaceutical agent is absorbed on or by certain cells in the body structure of interest and concentrates in this area. As an example, fluorodeoxyglucose (FDG) is a slight modification to the normal molecule of glucose, the basic energy fuel of cells, which readily accepts a radionuclide as a replacement to one of the atoms of the molecule. The radiopharmaceutical "tracer" emits a positron which creates photons that can be detected as the tissue is scanned at various angles and the photons pass through a detector array. A computer is used to reconstruct a three-dimensional color tracer image of the selected tissue structure.

With the foregoing background in place, exemplary current practice of generating, preparing, and administration of radiopharmaceuticals will now be described. Typical radiopharmaceutical treatment practice in the United States includes having the radiopharmaceutical agent initially generated off-site from a treatment location, typically a hospital, by an outside nuclear medicine facility and then delivered to the treatment location for further preparation, for example, individual dosing and administration. The treatment location, for example, a hospital, orders specific radioactive substances to be ready at specific time for specific patients. These substances are prepared by the outside nuclear medicine facility and with sufficient radioactivity that they will have the desired radioactivity level at the targeted time. For example, the outside nuclear medicine provider may have a facility equipped with a cyclotron or radioisotope generator in, for example, a lead-shielded enclosure wherein the radiopharmaceutical agent, namely, a radioactive isotope is generated or created. Further refining or dose preparation steps, namely, placing the radioisotope in injectable form, may occur at the off-treatment site. Thus, the outside provider may provide a radiopharmaceutical substance to the treatment site having a desired radioactivity level at the targeted time. Further "individual" dose preparation of the radiopharmaceutical agent may occur at the treatment site. Alternatively, the outside provider may provide a "finished" radiopharmaceutical agent ready for injection to a specified patient at a specified time so that treatment site personnel are only required to confirm that the correct radioactive dosage is present in the radiopharmaceutical agent, for example, in a stand-alone radiation dosimetry device as described previously. During the forgoing process, there is frequent close-proximity contact with radioactive materials by personnel and, as described previously, handling and transport shielding devices are needed for the protection of these personnel.

Transport pigs are commonly employed to transport the radiopharmaceutical agents, which are individual doses prepared for individual patients, to the treatment facility. At the treatment facility, data about each unit dose is entered into a facility computer either manually or through reading a bar code, floppy disk, or other similar data format, which may accompany or be on the transport pig or the radiopharmaceutical agent container. When it is time to deliver a specified unit dose to a specified patient, treatment facility personnel must remove, for example, a syringe containing the radiopharmaceutical agent from the transport pig and confirm that the dose in the syringe is within the range prescribed for that patient. Alternatively, the attending personnel must transfer the radiopharmaceutical agent to a shielded syringe as identified previously and confirm dosage. If the dose is too high, some is discarded into a shielded waste container. If the dose is too low, either a different syringe is used and/or additional agent is loaded into the syringe if available. While it possible for the attending treatment site personnel to be involved with dosage preparation, typical United States practice is to have the radiopharmaceutical agent delivered to the treatment site which will have the desired radioactivity level at the targeted time. Manual manipulation of the radiopharmaceutical agent at the treatment site is limited at the treatment site due to this procedure. Nonetheless, various manual checks are required to confirm that a correct radiopharmaceutical dose is ready for injection into a specific patient. These manual checks include visual inspections and radioactivity measurements as noted above.

As an example of the foregoing, in PET imaging, an injectable radiopharmaceutical agent such as, for instance, FDG (fluorodeoxyglucose) is fabricated in a cyclotron device at an outside nuclear medicine facility. Thereafter, the FDG is processed to be in a radiopharmaceutical form and is transferred in an individual dose container (i.e., vial, bottle, syringe, etc.) and the container loaded into a transport pig to prevent unnecessary radiation exposure to personnel, such as the radio-pharmacist, technician, and driver responsible for creation, handling, and transport of the FDG from the cyclotron site to the PET imaging site. Since the half-life of FDG is short, approximately 110 minutes, it is necessary to quickly transport the FDG to the PET imaging site. Depending upon the elapsed transport time and the initial radioactivity level of the FDG at the time of fabrication, the radioactivity level of the FDG may need to be re-measured at the PET imaging site. As an example, if the radioactivity level is too high, the transport radio-pharmacist of a radio-pharmacist at the PET imaging site may be required to dilute the FDG with a diluent such as, for instance, saline solution, and remove part of the volume or extract fluid to reduce radioactivity prior to patient injection. During this entire process, the handling of FDG from creation to patient injection may be entirely manual. Within this process, shielding products, as described previously (i.e., transport pigs, syringe shields, L-blocks, etc.) are used to shield individuals from FDG. While shielding may reduce the radiation exposure of the radio-pharmacist, the radio-pharmacist may still be exposed to emissions from the radiopharmaceutical agent during the manual mixing, volume reduction, and/or dilution process needed to obtain the required dose. After injection and often after an additional delay to allow the radiopharmaceutical to reach and be absorbed by the desired regions of interest in the body, the patient is typically placed on a moveable bed that slides by remote control into a circular opening of an imaging scanner referred to as the gantry. Positioned around the circular opening and inside the gantry are several rings of radiation detectors. In one type of radiation detector, each detector emits a brief pulse of light every time it is struck with a gamma ray coming from the radionuclide within the patient's body. The pulse of light is amplified by a photomultiplier converted to an electronic signal and the information is sent to the computer that controls the apparatus and records imaging data.

For the sake of completeness, it should be noted that in the United States it also known to have radiopharmaceutical agents delivered in a multi-dose format to the treatment site. As a result, this multi-dose format must be divided into singular doses for individual patients at the treatment site. While it possible that this dividing may occur at the point of injection or administration, it more typical for a radiopharmacist or nuclear medicine technologist to perform the dividing process in a "hot lab" at the treatment facility. Individual radiopharmaceutical doses are then transported to the administration location within the treatment facility where the doses are administered to specific patients.

In Europe, radiopharmaceutical creation and dose preparation practice differs from United States practice in that these actions typically all occur within a "hot lab" in the treatment facility again, typically, a hospital. As an example, the hospital itself typically has cyclotron or isotope generators (such as technetium generators manufactured by Mallinckrodt Inc., St. Louis, Mo.; Amersham Healthcare, 2636 South Clearbrook Drive, Arlington Heights, Ill. 60005; or GE Healthcare Limited, Amersham Place, Little Chalfont, Buckinghamshire, United Kingdom) in a shielded location in the hot lab. Two manufactures of shielded glove boxes are Comecer in Italy and Lemer Pax in France. Hospital personnel create or extract the radioactive isotope, perform additional chemistry steps necessary to formulate the radioactive drug (i.e., radiopharmaceutical) early in the day, and then prepare unit doses for individual patients, generally close to the time the patient is to be injected with the radiopharmaceutical. While an internal "hot lab" has advantages in minimizing hazardous material transport and improving internal information transfer, additional time and radiation burdens are placed on hospital staff as the measurement of radioactivity levels at the various steps still depends upon manual insertion of a container (i.e., a vial, bottle, or syringe) into a dose calibrator and then repeated adjustments of the radioactivity until the desired level is achieved. The unit dose radiation level is commonly recorded manually or by a printer.

Within the prior art, systems for delivering hazardous fluids are known as disclosed, for example, in U.S. Pat. No. 6,767,319 to Reilly et al. and United States Patent Application Publication No. 2004/0254525 to Uber, III et al., the disclosures of which are incorporated herein by reference. Another system adapted to inject a radioactive liquid into a patient is disclosed in Japanese Publication No. JP2000-350783 (see also United States Patent Application Publication No. 2005/0085682 to Sasaki et al.), assigned to Sumitomo Heavy Industries. This published patent application discloses a system which dispenses a volume of radioactive fluid into a coiled "medicine container" situated in a radiation measuring unit. When the prescribed radiation dose is accumulated in the coiled container, another syringe pushes saline through the coiled container and into a patient. A similar device and method is disclosed in Japanese Publication No. JP2002-306609, also assigned to Sumitomo Heavy Industries. Each of the immediately foregoing Japanese publications is incorporated herein by reference.

PCT Application Publication No. WO2004/004787, assigned to Universite Libre De Bruxelles—Hospital Erasme and incorporated herein by reference, discloses a method by which continuous measurement of radioactivity by dosimetry is eliminated. The disclosed method requires an initial calibration step but thereafter, radiation dose is calculated based on the predictable decay of radioactivity as a function of time. Japanese Publication No. JP2004-290455, assigned to Nemoto Kyorindo K, discloses a radiation-shielded injector system which withdraws FDG from prefilled syringes and allows other fluids such as saline to be administered. European Application Publication No. EP 1616587, assigned to University of Zurich and incorporated herein by reference, discloses a radioactive fluid dispensing device that pushes FDG into tubing within a radiation dose calibrator prior to a saline injection that administers the FDG to the patient. United States Patent Application Publication Nos. 2005/0203329 and 2005/0203330 to Muto et al. disclose a robotic, automated system for extracting radioactive fluids from a vial or bulk container into a number of unit dose syringes. This system may have application in a hospital pharmacy setting. United States Patent Application Publication No. 2005/0277833, assigned to E-Z-EM, Inc. and incorporated herein by reference, discloses an injection system for handling, mixing, dispensing, and/or injecting mixtures of pharmaceutical agents. Radiation dose is monitored by discrete detectors at several locations in the apparatus.

SUMMARY OF THE INVENTION

As the foregoing demonstrates, a need exists for integrated systems and methods capable of the generation, preparation, and administration of pharmaceutical substances and, typically, harmful or toxic pharmaceutical substances such as radioactive pharmaceutical substances or drugs, to human and animal subjects and, further, to methods and systems and associated components for the generation, preparation, and administration of fluid radiopharmaceutical substances to human and animal subjects.

Generally, embodiments and physical manifestations of an integrated system and method for generation, dose preparation, transportation, and administration of radiopharmaceuticals are provided with a focus on improving safety for attending personnel, effectiveness, ease of use, and costs involved in the creation, handling, and transport of radioactive fluids, such as FDG, for injection into a patient. In one aspect, a radiation shielded enclosure, housing, or container for individual containers (vials, bottles, syringes, etc.) of FDG is used at the point of radioisotope generation to completely contain and, further, measure a radioactive dose. As an example, such measurement is accomplished by a radiation dosimeter housed within the radiation shielded enclosure, housing, or container. This dosimeter may be calibrated for the specific geometry involved and for the specific isotopes, for example, 511 keV gamma photons, thereby eliminating the need for large, bulky, expensive dosimeters. In addition, inexpensive dosimeter(s) of similar design may be made configured to clip onto tubing between the radiation shielded enclosure, housing, or container and a patient. In use, the radiation shielded enclosure, housing, or container is transported to the point of use, typically a PET or SPECT scanner in a hospital, and is mechanically configured to dock with a fluid delivery system to deliver radioactive fluid and saline into a patient's vasculature. In other embodiments, radioactive waste is reduced by allowing accurate doses to be drawn from a shielded container into a small diameter syringe.

In another aspect, the radiopharmaceutical agent may be continuously circulated within a closed system in the fluid delivery system and mixed with saline on demand, such as by actuating a handcontroller, to control the radiation dose delivered to a patient. In such an integrated fluid delivery system, methods to optimally stage, monitor, and scan patients in a clinical environment are also provided. Elements of the integrated fluid delivery system include estimating the metabolic activity of a patient upon injection of the radiopharmaceutical agent, intelligent integration of the monitoring information into a centralized server for scheduling and organizing the work queue in an analogous manner to technology currently used in cardiac telemetry units, and control of the external environment in which the patient, post injection, is staged. The staging area may include intelligent sensors integrated with the scheduling and instrumentation server to allow for individualized lighting levels, temperature control, and configurable ventilation, radiation shielding, and patient positioning. An integrated fluid delivery system which can continuously circulate radiopharmaceutical agent to make a measured dose of radiation available "on demand" is another improvement for the nuclear medicine field. This system may optimize a radiopharmaceutical injection based on mathematical models of patient physiology, provide alternative methods of detecting radiation, and/or improved methods for isolating attending personnel from radiation emitted by a patient after injection of radiopharmaceuticals.

An exemplary application of the foregoing integrated fluid delivery system relates to the intelligent delivery and monitoring of radiopharmaceutical agents to maximize the uptake of agent into tumor sites and minimization of shunting into muscles, surrounding parenchyma, liver, and bladder. Site specific delivery (intratumoral) and monitoring using permittivity sensing is anticipated as being part of the implementation method. The explicit incorporation of physiologic levels of free glucose, metabolic analogues, renal function, tumor permeability, and tumor binding site dynamics into a control paradigm are desirable. The incorporation of the mentioned parameters into a predictive model, adaptive or robust controller will result in individualized injection trajectories for the fluid delivery or handling system, optionally including maintenance radiopharmaceutical dosing during the patient's stay in the staging area. Knowledge of the tumor permeability, vascularity, and other properties may be used in the estimation of a control signal for the radiopharmaceutical. A workstation that is able to process a CE (contrast enhanced) CT (perfusion), and/or DCE (dynamic contrast enhanced) MRI stack is envisioned that the clinician or operator interacts with when performing the fluid delivery regimen. Many radiopharmaceutical procedures (both diagnostic and therapeutic) result in suboptimal outcomes such as, for example, having FDG is shunted into a patient's bladder. The concepts described herein can improve the diagnostic or therapeutic outcome, minimize the load of radiopharmaceutical agent needed to perform the procedure, optimize uptake of the radiopharmaceutical agent into cancerous zones, and provide optimal timing and staging of the procedure.

Turning to specific embodiments described in detail herein, one embodiment relates to an integrated radiopharmaceutical patient treatment system, comprising a patient support platform with an associated patient stimulus apparatus, an imager proximate the patient support platform, a radiopharmaceutical fluid delivery system for infusing a radiopharmaceutical fluid into a patient, a patient monitor to be associated with a patient, and an integrated system controller operably associated with the patient stimulus apparatus, imager, radiopharmaceutical fluid delivery system, and patient monitor to control and coordinate their operations.

The patient support platform may support the patient in a non-prone orientation. The patient support platform may be integrated with the imager. The integrated system controller may interface with an imager controller controlling operation of the imager. The patient stimulus device may be adapted to induce cardiac stress in a patient by one or more of physical exercise, electrode stimulation, sensory stimulation, and drug stimulation. The stimulations may be used for purposes other than cardiac stress as well. The integrated system controller may be electronically linked to an information network associated with a patient treatment facility. The radiopharmaceutical fluid delivery system may comprise a plurality of fluid injectors each individually controlled by the integrated system controller.

Another embodiment described herein relates to a radiopharmaceutical fluid delivery system comprising a radionuclide supply module, a radiopharmaceutical processing module in fluid communication with the radionuclide supply module, a quality control module in fluid communication with the radiopharmaceutical processing module, a patient injection module in fluid communication with the radiopharmaceutical processing module, and a controller linked to the radionuclide supply module, the radiopharmaceutical processing module, the quality control module, and the patient injection module to control and coordinate their operations.

The radiopharmaceutical processing module, the quality control module, and the patient injection module may be supported within a radiation shielded mobile platform. A radiopharmaceutical waste fluid container may be disposed within the radiation shielded mobile platform and be in fluid communication with at least the radiopharmaceutical processing module. The patient injection module may comprise one or more fluid injectors. The radionuclide supply module may comprise a radionuclide generating device.

Another embodiment described herein relates to a hazardous fluid handling system, comprising at least one fluid delivery pump associated with a fluid source, at least one fluid withdrawal pump, and a fluid path connecting the at least one fluid delivery pump and the at least one fluid withdrawal pump to a delivery point for delivering fluid to a recipient. A controller is desirably operably associated with the at least one fluid delivery pump and the at least one fluid withdrawal pump to enable synchronous operation of the at least one fluid delivery pump and the at least one fluid withdrawal pump such that the at least one fluid delivery pump positively delivers fluid from the fluid source to the fluid path while the at least one fluid withdrawal fluid pump withdraws fluid from the fluid path.

The at least one fluid delivery pump may comprise a plurality of fluid delivery pumps connected with respective fluid sources at least one of which comprises a hazardous fluid. An in-line radiation dosimeter may be associated with the fluid path for detecting radiation emitted by a radioactive fluid in the fluid path. The at least one fluid withdrawal pump may comprise a plurality of fluid withdrawal pumps at least one of which is adapted to positively delivery fluid from an associated fluid source to the fluid path upon actuation by the controller. A fluid junction connecting respective portions of the fluid path may be associated with the at least one fluid delivery pump and at least fluid withdrawal pump. The fluid path delivery point may comprise a needle cannula integrated with the fluid junction.

A further embodiment described herein relates to a hazardous fluid delivery device, comprising a shielded housing defining an internal chamber for receiving a hazardous fluid container and an access port connected to the internal chamber to connect the internal chamber to a fluid path, a piston disposed in the hazardous fluid container, and a drive mechanism. The drive mechanism comprises a piston actuator adapted to interface with the piston via an opening in the shielded housing and reciprocally move the piston within the hazardous fluid container. The drive mechanism may be detachably associated with the shielded housing.

The drive mechanism may comprise a controlled power injector comprising a reciprocally movable piston actuator adapted to interface with the piston. The controlled power injector may comprise a cradle structure for supporting the shielded housing. The drive mechanism may comprise a motor operating as the piston actuator and detachably coupled to the piston. A control valve may be associated with the access port to regulate fluid flow to and from the hazardous fluid container. A radiation dosimeter may be provided proximate the internal chamber to measure radiation level of a radioactive fluid comprising the hazardous fluid contained in the hazardous fluid container.

In a further embodiment, a hazardous fluid handling system comprises a docking station and a hazardous fluid transport device adapted to detachably dock with the docking station. The docking station may comprise a pump, a user interface, and a control device electronically linked to the pump and the user interface. The docking station control device may be electronically linked to the hazardous fluid transport device and the pump may be in fluid communication with the hazardous fluid transport device to fill and dispense fluid to and from the hazardous fluid transport device when docked with the docking station.

The hazardous fluid transport device may comprises a housing comprising a radiation shielded internal chamber formed to contain a container holding a radioactive fluid, at least one radiation dosimeter detector disposed within the housing proximate the shielded internal chamber to detect radiation emitted by the radioactive fluid, and a dosimeter control device electronically coupled to the radiation dosimeter, the at least one radiation dosimeter providing a signal representative of the detected radiation level to the dosimeter control device.

The dosimeter control device may be electronically linked to the docking station control device such that the signal representative of the detected radiation level is displayable on the user interface. The user interface may be provided on the housing of the hazardous fluid transport device. A data recording device may be electronically linked to the dosimeter control device to record data unique to the contents of a radioactive fluid container received in the radiation shielded internal chamber in the housing. A communications interface associated with the docking station control device to link with an external electronic information network may also be included. A fluid path to an external source of hazardous fluid and in fluid communication with the pump and the hazardous fluid transport device when docked with the docking station may be used to permit the pump to fill the hazardous fluid transport device with hazardous fluid form the external hazardous fluid source. The external hazardous fluid source may comprise a radiopharmaceutical fluid source. The pump may also dispense fluid from the hazardous fluid transport device to the external location. In other embodiments, multiple dosimeters may be provided with associated control and coordination of output signals from the respective dosimeters.

Further details and advantages are described herein in connection with several embodiments of methods, systems, and apparatus for the generation, preparation, transportation and administration of pharmaceutical substances, typically intrinsically harmful or toxic pharmaceutical substances such as radioactive pharmaceutical substances, to human and animal subjects. Like parts are designated with like reference numerals throughout and, where applicable, alphabetical designations are associated with the reference numerals for clarity in describing the concepts of the inventions disclosed herein.

BRIEF DESCRIPTION OF THE DRAWINGS

FIG. 2C is a schematic representation of a representative physical implementation of the integrated systems of FIGS. 2A-2B.

FIG. 8 is an alternative embodiment of the fluid junction shown in FIG. 7.

FIG. 9 is a second alternative embodiment of the fluid junction shown in FIG. 7.

FIG. 10 is a third alternative embodiment of the fluid junction shown in FIG. 7.

FIG. 11 is a fourth alternative embodiment of the fluid junction shown in FIG. 7.

FIG. 12 is a top view of a portion of the fluid junction shown in FIG. 11.

FIGS. 35B-35C are schematic representative views of the dose adjuster of FIG. 35A according to several possible implementations.

FIGS. 39A-39C illustrate basic principles for calculated sensitivity for a small volume container such as in FIG. 38 comprising three detector positions.

DESCRIPTION OF THE PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific devices illustrated in the accompanying drawing figures and described herein are simply exemplary and should not be considered as limiting.

Figure 1:
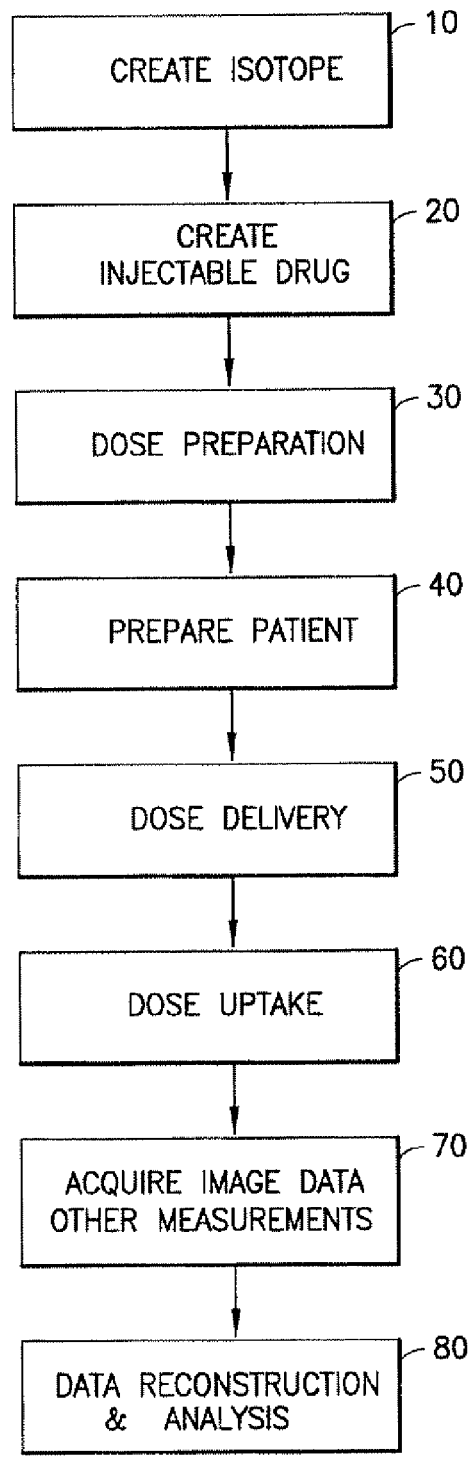
FIG. 1 is a flowchart of an exemplary process for radiopharmaceutical generation, dose preparation, and administration to a patient.

FIG. 1 is an exemplary flowchart showing a process for radiopharmaceutical generation, dose preparation, and administration to patient. In this disclosure, FIG. 1 will be discussed in connection with two specific radiopharmaceutical agents, namely, FDG (Fluorodeoxyglucose) used for cancer imaging which uses the positron emitter 18F (fluorine with an atomic mass of 18) and Cardiolite® used in coronary imaging diagnostic procedures which uses 99mTc (a metastable isotope of technetium of atomic mass 99). Nonetheless, FIG. 1 illustrates the overall procedure for the creation, refinement, and administration of injectable radioactive materials for diagnostic and/or treatment applications and typically those in fluid form (i.e., gas or liquid).

In FIG. 1, step 10 relates to creating an isotope which is the precursor material to the radiopharmaceutical agent. For example, 99mTc is created or generated in a commercially available technetium generator by natural radioactive decay of the longer-lived isotope molybdenum-99. Once created, the 99mTc is withdrawn from the generator by flushing water or saline through the generator into a container (vial, bottle, syringe, etc.). The technetium generator typically has two ports with needles. The first needle is used to puncture a vial of sterile saline and the second needle is associated with a vacuum source, for example, an evacuated container (vial, bottle, etc.). The vacuum source pulls saline from the saline vial through the generator into the evacuated container. This procedure is generally done manually by a radio-pharmacist. As an example, U.S. Pat. No. 4,837,110 describes eluting with saline-copper chloride mixture, incorporated herein by reference.

Step 20 in FIG. 1 relates to creating, synthesizing, or placing the radioactive isotope into an injectable or deliverable form or molecule. In some instances, the radioactive isotope in its raw form is intended for injection into a patient but not typically. A more typical example is to combine the radioisotope created in step 10 with a sterile powder. For example, in the manufacture of Cardiolite®, approximately 1 to 3 mL of a solution containing the created technetium (925 to 5550 MBq, (25 to 150 mCi)) is added to a sterile powder in a bulk container, typically a vial. Following the manufacturer's instructions, the vial is shaken and heated, typically in boiling water, for a predetermined period of time to promote the chemical incorporation of the technetium into the Cardiolite® molecule. After cooling, the vial (or possibly a syringe or a bottle) containing material is visually inspected for clarity and absence of particulates. The solution is now a radiopharmaceutical agent that is suitable for injection into a patient, human or animal. The Cardiolite® radiopharmaceutical agent may be stored for up to about six hours at a temperature of 15 to 25° C. The details of the chemistry and preparation of Cardiolite® are available from the manufacturer, Bristol-Meyers Squibb, 331 Treble Cove Road, N. Billerica, Mass. 01862. Containers (i.e., vials, bottles, syringes, etc.) of Cardiolite® are commonly stored in a shielded container to protect from radiation exposure.

Next, at step 30, the radio-pharmacist, or any medical personnel who is charged with preparing and possibly administrating the radiopharmaceutical, manually withdraws a quantity of solution from the bulk container, often a vial, using a shielded syringe by piercing the vial septum with the syringe needle. The needle is capped and the syringe is removed from its shield and placed in a radiation dose calibrator. After the radiation dose is measured and, depending on whether there is too little or too much radiation present, the radio-pharmacist estimates the volume that needs to be added from or returned to the bulk container (i.e., vial) from the measured radioactivity and the solution volume in the syringe. This entails removing the syringe from the dose calibrator, reinserting it into a syringe shield, and piercing the septum of the bulk container to withdraw additional solution or return some solution to the bulk container or, alternatively, to a waste container. The radio-pharmacist then again repeats the dose calibration step. If the radioactivity level is correct, further radiopharmaceutical preparation may occur. However, often a third iteration of the foregoing is required and, with each iteration, the radio-pharmacist or other medical personnel is exposed to radiation emanating from the bulk container and/or the individual dosage syringe. Generally, all these manipulations are done in a shielded glove box or behind a counter top shield so that the radiation dose to the radio-pharmacist's body core is significantly less than his or her hand dose. However, a certain level of exposure to the body core is also somewhat inevitable. When the "correct" dosage is finally obtained, the radio-pharmacist records the dosage on a piece of tape that is affixed to the syringe or the syringe shield encompassing the syringe. Alternatively, a label is produced by the dose calibrator which is affixed to the syringe or the syringe shield. Often, the dosage is only within +/−10% of the correct or desired dosage for the individual patient as the success of the foregoing procedure is tied to skill of the individual radio-pharmacist. Dose calibrators are well-known in the nuclear medicine field.

The individual patient is prepared for administration of the dose of radiopharmaceutical at step 40 by establishing access to the patient's vascular system via a needle cannula or catheter. Some radiopharmaceutical agents may be in gaseous form or are nebulized and thus are inhaled. Step 40 is shown occurring after dose preparation step 30 but it will be clear that sequential following of the flowchart of FIG. 1 is not strictly required and, for example, patient preparation step 40 may occur in parallel with any of preceding steps 10-30. Accordingly, a patient may be prepared in parallel with or even before step 30, the preparation of the individual dose. Radiopharmaceuticals are alternatively delivered orally, topically, or are injected into tissue, body cavities, or other volumes. One application of radiopharmaceutical agents is as part of a cardiac stress test wherein the patient's heart rate is increased to measure cardio-vascular performance and obtain information regarding possible vascular occlusions. Accordingly, once a conduit is established to provide the radiopharmaceutical agent to the patient, additional patient preparation may occur, such as attaching ECG electrodes to the patient and monitoring the ECG as the patient's heart rate is increased through exercise on a treadmill, stationary bicycle, or similar machine, or a pharmacological stress agent is introduced into the patient. This specific application of radiopharmaceutical agents is described in detail herein. For brevity purposes, it sufficient to state with regard to this specific application that when the patient's heart rate is sufficiently high, the correct dose of radiopharmaceutical agent is delivered to the patient intravenously at step 50 and the dosing information is recorded in the patient's medical record. After a preset period of time elapses for dose uptake as at step 60, the patient may be moved to an imaging unit for PET or SPECT imaging as examples. The time delay may be zero as, for example, delivery may take place while the patient is in the imaging unit and imaging may start immediately upon or even before injection of the radiopharmaceutical agent. Generally for a cardiac study, the stress is continued for one minute as the heart muscle absorbs the radiopharmaceutical. Imaging can take place sometime after that event, commonly within thirty minutes.

At the imaging unit, imaging data is acquired in the present example at step 70. It may be incumbent on the imaging unit operator to input patient-specific information about the patient into the imaging unit controller and select the proper study. As indicated, the imaging unit acquires data at step 70 with little additional operator interaction or intervention. After the data is acquired at step 70, it can be reconstructed and analyzed at step 80 as is known in the nuclear medicine field and, more specifically in this example, the nuclear cardiology field. At step 80, the imaging unit controller may automatically or via operator input correct for certain variables such as attenuation by the patient, and the operator optionally reformats and adjusts the information to the preferences of the individual clinician typically a physician. Moreover, at step 80 the physician reads the case study and renders an opinion which can range from concluding that the study shows an absence of perfusion, ejection fraction, or other anomalies allowing the patient to be discharged or concluding that anomalies are present and prescribing a rest study. If a rest study is to be conducted, the patient is taken out of the imaging unit and allowed to rest further. Then, a second larger dose of Cardiolite® is typically injected. After another preset period of time, for example several minutes, imaging is conducted and this typically concludes the "stress test" procedure. In some cases the rest study is done before the stress study.

In an alternative to the foregoing example, FDG, described previously, may be administered to a patient in a somewhat similar manner to the foregoing technetium (Cardiolite®) example. However, FDG is created and prepared for dosage to the patient in a slightly different manner from Cardiolite®. In this alternative sequence, positron emitter 18F, used in making FDG, is created, (at step 10), in a cyclotron or accelerator which is a very expensive piece of capital equipment. In the cyclotron, 18O water is bombarded with protons and some of the 18O changes into 18F. A batch of water with the 18F, generally one to two ml in volume, is sufficient to be used in several imaging procedures. The chemistry for incorporating the 18F into FDG is commonly done in a "hot" lab in close proximity to the cyclotron (at step 20). Generally, automated chemistry units, such as the TRACERLab MX FDG system available from GE Medical Systems, are used to create the multiple doses of FDG in a single batch. A transportable facility for accomplishing these steps is described in United States Patent Application Publication No. 2004/0086437 to Jackson, which is incorporated herein by reference.

In the hot lab, liquid sufficient for multiple doses of FDG is placed into a shielded bulk container (vial, bottle, syringe, etc.), or it is separated into individual doses or unit doses which are placed into shielded syringes, with the radioactivity determined by the prescription and imaging time for each patient and thus rendering a prepared dose for each patient as at step 30 in FIG. 1. This step is usually done automatically because the radiation from 18F is much higher energy than technetium and so it is preferable to keep the radio-pharmacist distanced from the material. Comecer of Italy makes a large, multi-ton, robotic system for accomplishing this task. The FDG (bulk or individual doses) is transported to the patient treatment site. If the cyclotron is not at the treatment site, the FDG (bulk or individual doses) is transported to the location for final dose preparation and dose delivery. If the FDG arrives in bulk form, the radio-pharmacist manually prepares individual patient doses using the manual procedures outlined previously in relation to technetium. If the FDG arrives in unit dose form, the radio-pharmacist or nuclear technologist is still required to manually confirm the dosage with a dose calibrator and make adjustments if needed.

The FDG, typically in a shielded syringe, is then transported to the injection site in, typically, a shielded transport container (i.e., a transport pig). Alternatively, some shielded containers are similar to heavy metal lunch boxes. In the injection room, a clinician, for example, a physician, nurse, or technician delivers the FDG to the patient, typically intravenously via a needle cannula or catheter inserted in the patient, as at step 40 of FIG. 1. For example, a saline drip bag may be connected to the patient via an IV needle. The clinician or technician then removes the shielded syringe from the transport pig and inserts the syringe needle into a port in the IV line to inject the radiopharmaceutical into the patient as at step 50 wherein dosage delivery occurs. Optionally, a flush with saline may be performed to quickly push all the FDG into the patient's body. The syringe is typically then returned to the shielded transport container (i.e., pig) and any residual dose is measured in the hot lab's dose calibrator. As an example, for normal cancer imaging rather than cardiac stress test imaging, the patient typically waits without physical activity in a darkened room for thirty to sixty minutes, as at step 60. The patient is then transported to an imaging unit, (PET or SPECT), and imaging data is acquired to create an image as at step 70 in FIG. 1.

In the foregoing description associated with FIG. 1 exemplary processes for radiopharmaceutical generation, dose preparation, and administration to a patient are revealed. It is evident that there are many manual steps which expose one or more medical personnel to radiation exposure. Some of the described steps involve creation of radioactive material, physical transport of radioactive material, transfer of that material between containers, and the iterative adjustment of radiation doses for patients. It is clear that opportunities for improving the foregoing processes are present for the benefit of patients and medical and/or transport personnel which this disclosure now turns to for further explanation.

Figure 2A:
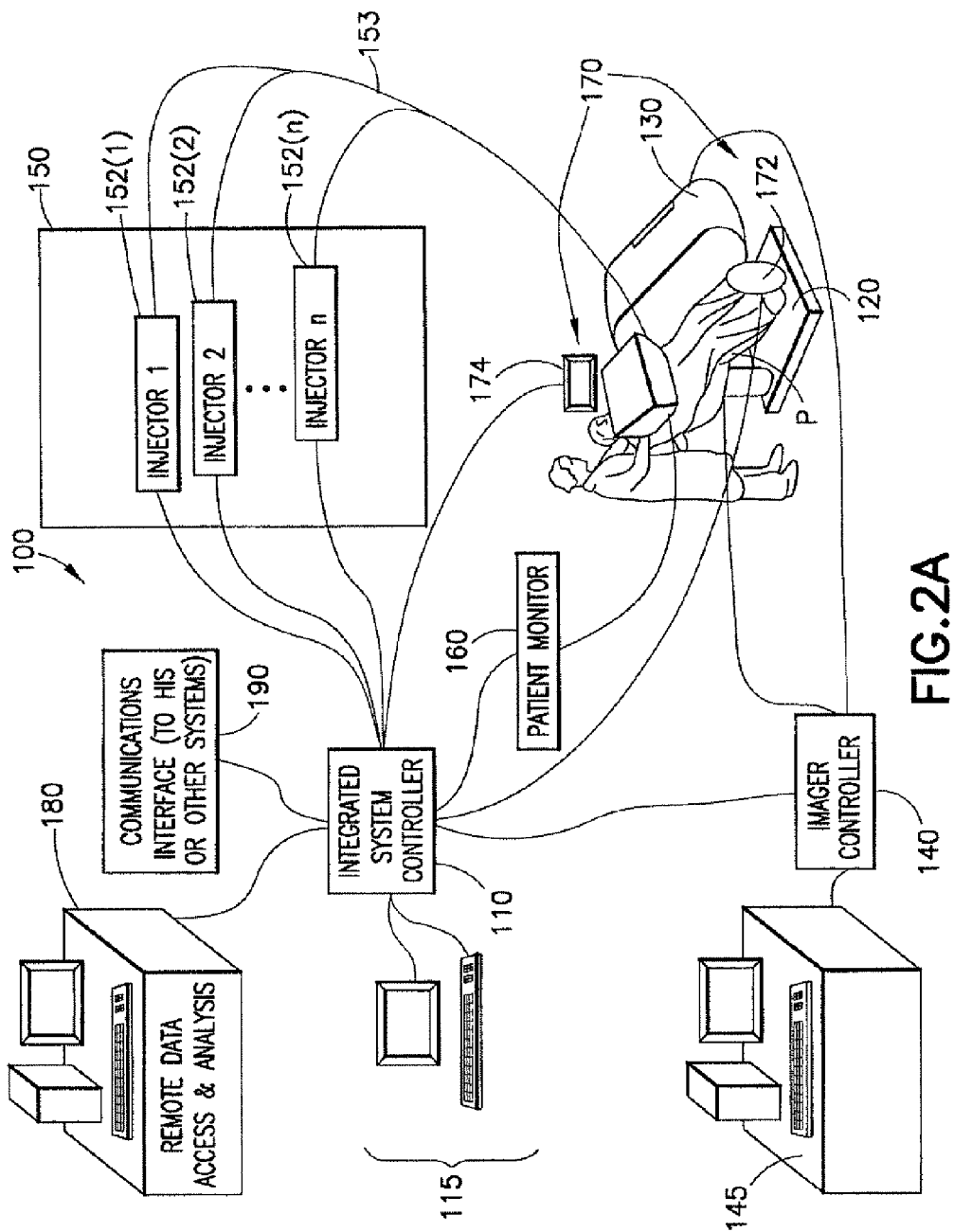
FIG. 2A is a schematic representation of an integrated system for generating, dose preparation, and administration of radiopharmaceutical agents and subsequent imaging of a patient and including features for stimulating and monitoring the patient as well and integrating the various component of the system.

Referring to FIG. 2A, a total or integrated system 100 for generating, dose preparation, and administration of radiopharmaceutical agents is illustrated. The total or integrated system 100 includes several subsystems, modules, devices, or components which will be individually described herein. The immediately following discussion broadly describes the individual or constituent units and their physical arrangement in the total or integrated system 100 (hereinafter "integrated system 100"). The integration of integrated system 100 is provided by one or more of: a physical arrangement or proximity of subsystems, modules, or components that facilitate an operator's execution of an imaging or therapeutic procedure by functional interoperability of system parts that enable safe, effective transfer of material, information, or control, and/or by a coordination of action desirably facilitated by an integrated system controller 110, typically computerized or electronic, that controls, coordinates, and/or automates various subsystems, modules, devices, or components through the steps in the desired procedure.

Figure 2B:
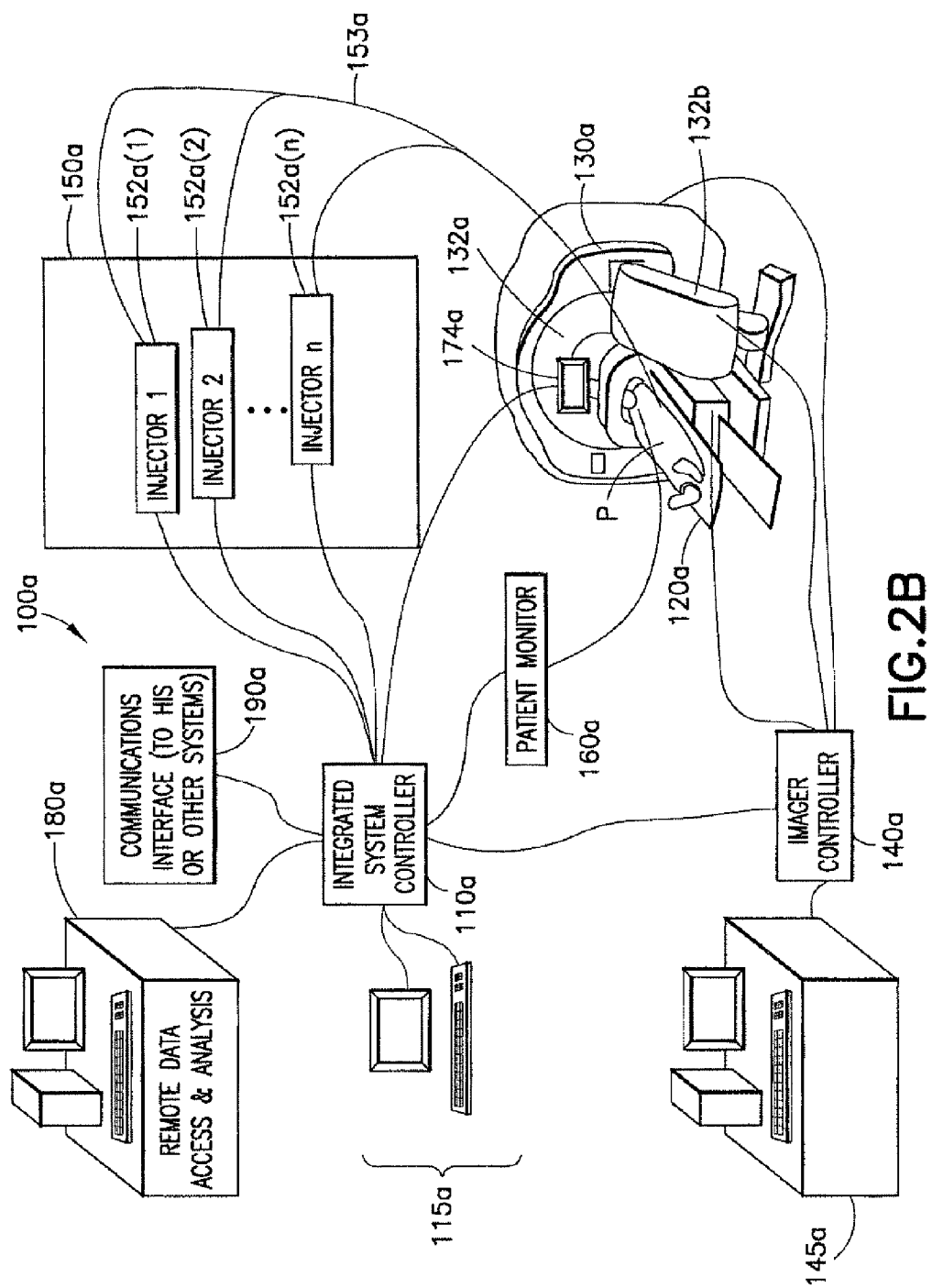
FIG. 2B is a schematic representation similar to FIG. 2A illustrating another embodiment of the integrated system.
Figure 2D:
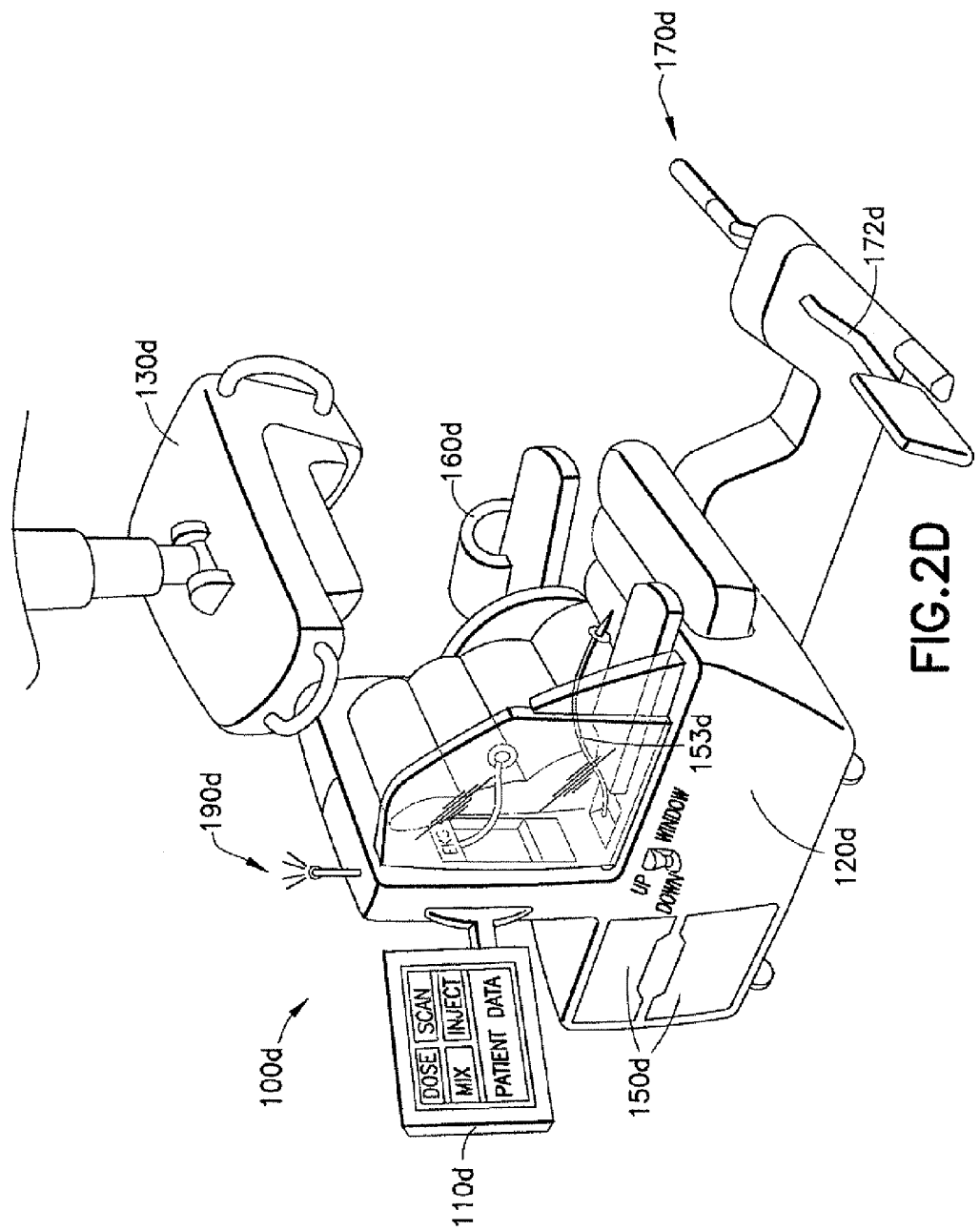
FIG. 2D is a schematic representation of another representative physical implementation of the integrated systems of FIGS. 2A-2B.

A first subsystem is a patient support 120 which supports a patient P in a desired, consistent, and controllable position with respect to an imaging system or, generically, an imager 130. In FIG. 2A, patient support 120 is a chair in which patient P is held in a semi-reclined state. In FIG. 2B, patient support 120a is an examination table whereon the patient is fully reclined. Other options are possible, for example, patient P could be upright or erect. MRI imaging units are known that allow for imaging of upright patients as manufactured by FONAR Corp., 110 Marcus Drive, Melville, N.Y. 11747. Another example is disclosed in U.S. Pat. No. 5,967,983 to Ashburn, incorporated herein by reference. FIGS. 2C-2D are schematic and ergonomic representations of representative physical embodiments of the integrated systems of FIGS. 2A-2B.

Imager 130 is used to sense energy or measure characteristics of patient P and create a data set, often viewed by the operator or physician as an image or set of images. Exemplary examples devices for imager 130 include nuclear medicine imagers (traditional gamma cameras, SPECT—Single Photon Emission Computed Tomography and PET—Positron Emission Tomography) in which energy is emitted from patient P and detected by imager 130, CT (Computerized Tomography), wherein X-ray energy is generated by imager 130 and sensed by imager 130 after passing through patient P, MRI (Magnetic Resonance Imaging) which uses magnetic fields and RF energy to measure information about patient P, ultrasound imaging, and various light or luminescent imaging. Imager 130 and patient support 120 interact so that the operator at a console 145, for example, associated with imager controller 140, may select regions of patient P to be studied, and the study may then be conducted under the control of the imager controller 140. Often, patient support 120 is considered a part of imager 130. Imager controller 140 may be embedded or otherwise integrated to be part of the imager 130 to coordinate and execute the significant tasks of data acquisition, analysis, display, and control of the various parts of the imager 130. Imager 130a may be comprised of two or more components, as in FIG. 2B, for example, a SPECT camera or imager 132b and a CT imager 132a. Imager controller 140 may be interfaced with patient support 120 to sequentially position the region to be studied in the appropriate areas of the two imager subsystems, namely, SPECT camera 132b and/or CT imager 132a. Images may be taken and combined into a single image for presentation to the operator or physician for diagnosis. In embodiments, such as that depicted in FIG. 2B, wherein there are two or more different imaging devices combined in a single imager or are in close proximity to each other so that they can be used successively on a single patient, it is preferable that fluid handling system 150a, described herein, include imaging contrast fluids or fluids appropriate for each of the imaging modalities.

Another aspect of integrated system 100 includes a subsystem or module 150 for fluid handling and delivery or administration to patient P in integrated system 100. Within fluid handling system 150, one or more fluid handling devices 152, are provided. Such delivery devices or pumps are commonly referred to as fluid injectors and each "injector" 152 is separately identified in FIG. 1 by a numerical identifier. One possible embodiment for fluid handling system 150 is described herein in connection with FIGS. 3-4. Exemplary devices for fluid injectors 152 are also described herein. However, it will be clear from FIG. 2A that one or more of fluid injectors 152 may be fluidly connected to patient P via an intravenous ("IV") fluid line 153 terminating in a needle cannula or a catheter (not shown) and appropriately inserted into patient P by medical personnel in advance of conducting the intended procedure. Fluid injectors 152 are desirably individually controlled by integrated system controller 110 to deliver one or more fluids, sequentially or simultaneously, at volumes and time varying flow rates in accordance entered or selected sequences or protocols of integrated system controller 110. Accordingly, integrated system 100 provides the ability to coordinate singular or multiple fluid injectors 152 which may be useful for more sophisticated medical procedures such as target cancer treatments or physiological function studies. The number of fluid injectors 152 and, accordingly, the number of individual fluids to be delivered to patient P is only limited by the needs of the medical procedure. Multi-fluid fluid handling system 150 could be incorporated into integrated system 100 as the only fluid delivery component of system or could be augmented by other fluid delivery vehicles as desired. Aspects of an injection system useful to facilitate the safe dosing of multiple patients from a bulk or multi-patient container are disclosed in U.S. Pat. Nos. 5,569,181; 5,806,519; 5,843,037; 5,739,508; and 5,840,026; and their progeny, all incorporated herein by reference. Multi-fluid fluid handling system 150 may be mounted in various ways that are commonly used in the medical field for fluid delivery units associated with imaging devices or scanners. Mounting on a wheeled pedestal or from an overhead counterpoise are exemplary options. Wall mounting is a third option. And, while multi-fluid fluid handling system 150 is illustrated separately from imager 130, this device may be incorporated into the body of imager 130 pursuant to the disclosure of U.S. Provisional Patent Application No. 60/807,532, filed Jul. 17, 2006, and entitled "Integrated Medical Imaging Systems", now PCT Application No. PCT/US07/073673 filed Jul. 17, 2007 under same title.

Another aspect of integrated system 100 optionally includes a patient monitor or measurement subsystem 160, module, or component which is in addition to, in combination with, or possibly substitutes for patient monitoring and measuring functions performed by imager 130. An exemplary and non-limiting listing of such measurements include heart rate, ECG (electrocardiogram), blood pressure, EEG (electroencephalography—brain activity measurement), EMG (electromyography—measurement related to muscle activity), blood oxygenation level, blood glucose level, insulin level, etc.

In the case of cardiac stress test procedures, it may be desirable to add or integrate a patient stimulus unit or apparatus 170 into integrated system 100. One example of patient stimulus unit or apparatus 170 is an apparatus or device on which patient P can physically exercise to increase the stress on the heart, such as a bicycle, treadmill, stair climber, elliptical trainer, or some other exercise machine. A bicycle-type stress patient stimulus device 172 is indicated schematically in FIG. 2A for exemplary purposes. Within cardiac stress test procedures, it may be desirable to regulate bicycle speed, resistance, or other operational parameter via integrated system controller 110 and display these values on integrated system controller 110. This is a physical patient stimulus. A sensory patient stimulus could be affected via input to one or more of the senses, for example, a viewing screen 174, audio inputs, by direct electrode stimulation of muscles, or by other physiological processes. Sensory patient stimulus could be coupled with physical patient stimulus or could entirely supplant physical patient stimulus in integrated system 100. Moreover, pharmaceutical patient stimulus could be accomplished by injection of an appropriate drug or physiologically active fluids with the goal being to stimulate or stress the patient's body, such as the heart muscle, to record images of the response. Again, this could augment one or both of physical and sensory patient stimuli. Other patient stimuli are optional, such as through electrodes, temperature, or other phenomena. It is within the scope of this disclosure to provide a system that enables a physician or researcher to use any one of or any combination of stimuli, with physical, sensory, and drug-induced patient stimulus as examples to achieve the desired stimulating effect on patient P in integrated system 100.

Given the state of the art with respect to electronics, computers, software, and control systems, integrated system controller 110 may be embodied in a single physical unit as shown in FIG. 2A or dispersed, possibly preferably, in two or more separate computers or sub-control units (not shown but readily within the skill of one skilled in the art) and which are operationally coordinated in a manner sufficient to achieve the same operational control afforded by integrated system controller 110. Integrated control of integrated system 100 allows the goals of the procedure to be accomplished with minimized operator input which reduces the possibility of operator over-tasking and, thus, reduces the chances for human error. Integrated control also enables automatic sequencing, timing, and coordination of diverse aspects such as patient positioning, stimulus, fluid delivery, and image acquisition that are beyond the ability of a human to coordinate alone. An additional aspect that tends to promote the segmentation or distribution of integrated system controller 110 is that different subsystems, components, or devices may be manufactured by different manufacturers and may optionally be able to operate without incorporation or integration into this total system. Thus, they will need to have sufficient control, communications, and user interface capability to operate on their own. By use of communications protocols, for example, those disclosed for communications between an injector and imager in U.S. Pat. No. 6,970,735 to Uber, III et al. and incorporated herein by reference, imager and injector subsystems with fully independent operation can be made to act as a single unit from the operator's point of view. Any of the many published communications standards such as Ethernet or CAN may be used as well. Integrated system controller 110 includes one or more user interfaces 115 through which the operator can set up or program the operation of integrated system 100, enter patient information, and monitor the operation of integrated system 100. Part of the benefit of integration is that the operator need only enter a piece of information once and it is available throughout the system. As with integrated system controller 110, one user interface 115 may serve to control the whole integrated system 100, several subsystems, or a single subsystem. Alternatively, there can be several interfaces that provide similar or redundant control functions located in different places, for example, at the patient's side, at imager 130, at a remote data access and analysis location 180 such as a radiology reading room or in a shielded control room to enable the operator to control or monitor integrated system 100 from the most convenient location.

Furthermore, integrated system controller 110 may also communicate information to and from other external information sources or networks via communications connection or interface 190. One example is the ability to send data or images to a PACS (Picture Archiving and Storage) system for subsequent access, "reading", and diagnosis by a doctor. Retrieving data or images from a PACS system for comparison with the current study is also advantageous. A second communications connection of significant benefit is to a Hospital Information System (HIS). This communications connection or interface 190 allows data about scheduling and patient P to be brought into the integrated system controller 110 to inform the operator of the procedure and patient conditions. This communications connection or interface 190 enables procedure results and notes to subsequently be communicated to physicians, patient records, and other appropriate systems. Examples indicating the benefits of communications between injectors and imagers are disclosed in U.S. Pat. Nos. 5,840,026 and 6,970,735, incorporated herein by reference previously.

An exemplary use of integrated system 100, as noted previously, is in performing cardiac stress tests. This test is typically prescribed when it is suspected that a patient P has a serious heart problem, specifically reduced perfusion or blood flow to a region of the heart when under stress. A technetium stress test is often prescribed by a cardiologist to confirm or eliminate the diagnosis. To conduct this test, patient P arrives at an imaging center and the necessary paperwork is completed. The procedure is explained to patient P and informed consent is received. An intravenous line is placed in the patient's arm and ECG electrodes are attached to his or her limbs and/or his or her chest and/or back. This can be done either before or after patient P is placed on patient support 120. Information or data about patient P is entered into integrated system controller 110 either by the operator and/or through communications connection or interface 190. A recommendation on patient dosing can be derived from data such as the study to be conducted, the patient's weight and build (BMI—body mass index), and mass of heart, if known. If this is a repeat study for this patient P, information about previous dosing may be accessed, and the current dosing is optionally made to be consistent with the previous study for quantitative comparison and trend analysis. After operator confirmation, an imaging agent, for example, a dose of Cardiolite® or Myoview® is prepared by fluid handling (i.e., injector) subsystem 150.

With patient P on patient support 120, a blood pressure monitor is attached, usually to the arm opposite the intravenous line. Fluid handling system 150 is interfaced to the patient's IV fluid line 153. Optionally at this time, imager 130 is positioned appropriately relative to patient P. Patient P is then stimulated to increase his or her heart rate. For example, physical stimulation may be initiated by patient P pedaling bicycle-type patient stimulus device 172. Heart rate is monitored and, when patient P reaches the target heart rate, for example, 80% of their age-adjusted maximum heart rate, integrated system controller 110 recognizes this condition and automatically, or upon confirmation by the operator, injects patient P with radiopharmaceutical agent. Patient P continues pedaling for approximately one minute. During that minute the radiopharmaceutical agent is taken up into the heart muscle in proportion to perfusion or circulation that the muscle receives. After that minute, patient P is told to stop pedaling and rest. When the patient's heart rate returns to near normal, or at least to a slow enough rate, imager 130 is started. Images are acquired in synchrony with the ECG so that images may be retrospectively reconstructed to show the shape of the heart and its perfusion at different phases of the heartbeat. Perfusion defects may be seen on the images and optionally measured quantitatively. The consistency and accuracy in dosing, timing, and imaging provided by the concepts of this disclosure will increase the usefulness of quantitative assessments which is rarely done in current practice in the nuclear medical field. Wall motion and ejection fraction are commonly also assessed.

If patient P is unable to operate a bicycle-type or another physical exertion patient stimulus device 172, for example, because of joint problems or age, pharmacological stressors may be used, such as dobutamine. In this case, fluid injector 152(2), as an example, in fluid handling system 150 is used to deliver dobutamine in gradually increasing quantities until a target heart rate is achieved. One important consideration is to arrange tubing connections to fluid injector 152(2) so that a large dose of dobutamine is not injected into patient P when fluid injector 152(1), for example, delivers the imaging radiopharmaceutical agent. A simple way to accomplish this result is to have separate, small diameter tubes or multiple lumens in a single tube from the dobutamine injector 152(2) and the radiopharmaceutical agent injector 152(1) connected very near the location where the IV fluid line 153 enters into the patient's arm.

If the stress test is normal, that is, if the heart muscle seems to be well-perfused, then there is no need for a subsequent resting test. If a part of the heart muscle is abnormal, that is under-perfused, and then a resting test is typically conducted. A significantly higher dose of the same imaging radiopharmaceutical agent is prescribed, computed, and injected but without any exercise or stressor drug to increase heart rate. After about a minute, another image may be acquired. As a general assessment, areas that are normally perfused on both images are considered healthy. Areas that are under-perfused in the stress test but normal on the rest test are at risk for a heart attack. Areas that are under-perfused on both images represent tissue damaged by a previous heart attack.

In the foregoing technetium stress test example, imager 130 is commonly not able to take an image during the time that patient P is being positioned and during the exercise interval used to increase heart rate. Also, it is normal practice to not observe the technetium in the patient's heart until several minutes after injection, commonly 15-30 minutes. An alternative arrangement in this integrated system 100 in to place an imager head or detector in association with imager 130 on a mechanical support, track, arm, or even a motorized positioning system or robotic arm to enable a single imager 130 to be shared with two patient support and stimulus apparatus 120, 170 "stations". Thus, imager 130, which may be the most expensive component of integrated system 100, may be more efficiently utilized in integrated system 100. Thus, integrated system 100 is not limited to just one of each of the subsystems, devices, or components discussed hereinabove. Exemplary benefits of the integrated system 100 illustrated in this example include the ability to automatically acquire information about patient P and the study, determine the dose to be provided based upon patient and study parameters, ensure accuracy and consistency of dose better than can be done manually, and automatically inject the dose when the heart rate or other patient parameters are appropriate.

A second exemplary use of integrated system 100a (FIG. 2B) in a clinical procedure that would benefit from the "integrated" aspects of integrated system 100a is a dynamic PET or PET/CT scan. Dynamic studies involve observing or measuring the different uptake, pharmaco-dynamics and pharmacokinetics, of an imaging radiopharmaceutical agent into different tissues. The concentration/time curves may be used to differentiate tissue and disease that cannot be sufficiently differentiated using a static image at a single specific point in time. Specific examples are provided hereinafter. A PET/CT scanner is closer to that of FIG. 2B where a patient lies on a horizontal patient support 120a that moves them between a PET and a CT section of imager 130a.

To conduct a dynamic PET/CT scan using integrated system 100a as illustrated in FIG. 2B, patient P arrives at the imaging center and the necessary paperwork is completed. The procedure is explained and informed consent is received. Intravenous fluid line 153 is associated with the patient's arm. There is generally no need to monitor the patient's ECG, although, if the region of interest includes the heart, this can be done to enable retrospective gating for image reconstruction. Information or data about patient P is entered into integrated system controller 110a, either by the operator and/or through communications connection or interface 190a. From data such as the study to be done, the patient's weight, build (BMI—body mass index), and/or lean body mass, a recommendation on dosage to be given may be derived. If this is a repeat study for this patient P, information about previous doses may be accessed and the current dose is optionally made to be consistent with the previous study for quantitative comparison unless overridden by the attending operator or physician. After operator confirmation of the quantity recommended by the system, the imaging radiopharmaceutical agent, a dose of PET agent, typically FDG is optionally prepared and delivered by fluid handling system 150a. Once patient P is properly positioned on patient support 120a, fluid injector 152a(1), as an example, is connected to IV fluid line 153, the FDG is prepared, imager 130a started, and the FDG is injected. For a typical dynamic study, the whole dose of a few milliliters is injected as quickly as possible, for example, in one or two seconds, and followed with a saline flush to ensure complete delivery to the patient. Imager 130a then acquires images of the initial uptake. A common protocol involves images of one minute length for the first five minutes, then two minute lengths for the next ten minutes, and then five minute lengths for the next forty-five minutes.

A research group from Heidelberg (Strauss et al., "Shortened PET Data Acquisition Protocol for the Quantification of F18-FDG Kinetics", J Nuc Med (2003) 44:12, 1933-1939, incorporated herein by reference) has found that acquiring images during the first ten minutes and then acquiring an image from fifty-five to sixty minutes after injection provides information that is sufficient for a dynamic scan. If this Heidelberg protocol is followed, the PET imager can be much more efficiently used, with four patients being scanned in the hour that one could be done previously. A factor in enabling this Heidelberg protocol is having integrated system 100a accurately inject a customized dose of imaging radiopharmaceutical agent, right at imager 130a for the dynamic study. A second factor in enabling the Heidelberg protocol is registration of the final image with the initial set of images. This is preferably done using a PET/CT imager and using bony landmarks for the image registration. In further detail, a low resolution CT image is done for landmark identification and attenuation correction. The imaging radiopharmaceutical agent is injected and the initial dynamic series of PET images is acquired. Patient P is removed from patient support 120a and goes into a quiet room to wait. At a point optionally about forty-five minutes after the injection, integrated system controller 110a alerts the operator that the patient needs to be brought back in ten minutes. This can be done many ways, including through a pager or cell phone. Thereby, approximately fifty-five minutes after injection, patient P is brought back to patient support 120a and positioned in approximately the same position. A low resolution CT is performed to select the PET imaging area and correct for attenuation. Then, the five minute PET image is acquired. The operator selects the region or regions of interest for which the dynamics are to be computed. The low resolution CT images from the two imaging sessions are used to synchronize or align in all three dimensions the regions of interest between the two sessions. Algorithms in integrated system controller 110a fit curves to the pixel or voxel information and extract the uptake constants, as described in the above-referenced Heidelberg protocol and paper. It is also preferred that integrated system controller 110a alert the operator if there will be a conflict for imager resources, for example, if the operator is setting up to scan one patient, and that patient's scan overlaps with the time slot needed to complete the 55-60 minute final scan of a previous patient. Similarly, with integrated system controller 110a having information about the patients to be scanned for the day, it can recommend sequencing of dynamic and non-dynamic scans to maximize the utilization of imager 130a.

As described in the foregoing, current practice in nuclear medicine typically consists of static images taken well after a radiopharmaceutical tracer has circulated through the patient's blood and has been taken up by targeted tissue. PET images with FDG are normally taken at least an hour after injection. SPECT images of cardiac perfusion with technetium-99m sestamibi, or thallium-201, for example, are acquired over a 20-30 minute period after the patient has exercised or has received an infusion of cardiac stress drugs such as adenosine or dobutamine. One reason often cited for relying upon equilibrium images in nuclear medicine is the need to integrate the relatively low number of disintegration events over time in order to improve the signal to noise statistics.

Other imaging modalities such as CT and MR are making use of the information in images sampled more frequently in time. This "dynamic imaging" approach, described previously in connection with FIG. 2B, yields additional physiological information such as quantitative perfusion and blood flow, utilization of metabolites in tissue, and tumor vascularization. With the CT and MRI modalities, images with good statistics may be acquired quickly from large ensembles of molecules. However, as the sensitivity of detectors for nuclear medicine improves, it will be possible to extract more signal and, thus, create less noisy quantitative information from multiple, time-sampled PET and SPECT images. A few representative applications are described hereinafter.

In dynamic imaging, PET images of FDG are used to distinguish inflammation from malignant processes in tissue. (Zhuang, et al., "Dual Time Point F18-FDG PET Imaging for Differentiating Malignant from Inflammatory Processes", J Nuc Med (2001) 42:9, 1412-1417, incorporated herein by reference). In general, dynamic images with radioisotopes may be combined with dynamic (kinetic) compartmental models to estimate underlying physiological parameters that differentiate between clinical states. (Coxson, et al., "Consequences of Using a Simplified Kinetic Model for Dynamic Pet Data", J Nuc Med (1997) 30:4, 660-667; and Sugawara, et al., "Germ Cell Tumor: Differentiation of Viable Tumor, Mature Teratoma, and Necrotic Tissue with FDG PET and Kinetic Modeling", Radiology, April 1999, 249-256, both incorporated herein by reference). Tumor metabolism may also be characterized from PET FDG images, and blood flow may be mapped with O-15 water images taken several minutes apart. (Zasadny, et al., "FDG Metabolism and Uptake Versus Blood Flow in Women with Untreated Primary Breast Cancers", Eur J Nuc Med (2003) 30:2, 274-280, incorporated herein by reference). Recent developments in dynamic SPECT ("dSPECT") using Teboroxime Tc-99m have shown value in identifying and quantifying cardiac flow defects while eliminating the problem of overlapping liver and heart distributions due to differences in uptake rates for those tissues. (Celler, et al., "Investigation of the Dynamic SPECT (dSPECT) Method for Teboroxime Using a 4-D Kinetic Thorax Model dMCAT", Sixth International Meeting on Fully Three-Dimensional Image Reconstruction in Radiology and Nuclear Medicine, 2001, incorporated herein by reference).

There is also a class of tracer studies that will benefit from dynamic imaging. These are "receptor blocking studies". In these studies, several fluids are injected into a patient's vasculature, typically a radioactive and non-radioactive version of the same chemical agent. These agents compete for specific receptor targets in tissue or on the surfaces of cells, thereby affecting the uptake of the radioactive components that can be imaged by SPECT or PET. The integrated system 100, 100a described in this disclosure will allow for time-sequenced administration of radioactive and non-radioactive agents in order to saturate the receptors without exceeding radiation dose limits or mass limits prescribed for an individual patient. In general, this dynamic administration of drugs or agents will require an additional fluid (such as normal saline) to flush the infusion lines of any residual materials. In other instances, it will be necessary to use an additional fluid to dilute the active drugs or agents to be isotonic with respect to blood, plasma, or extra-cellular fluid. A specific example of such dynamic receptor studies is described by Morris, et al. ("Comparison of Two Compartmental Models for Describing Receptor Ligand Kinetics and Receptor Availability in Multiple Injection PET Studies", Journal of Cerebral Blood Flow and Metabolism, (1996) 16:5, 841-853, incorporated herein by reference). A radiotracer with high specific activity ("hot") is injected over thirty minutes, for example by fluid injector 152(1) in integrates system 100 followed by an infusion of the non-radioactive ("cold") version of the tracer, for example, by fluid injector 152(2). A third fluid injector 152(3) could deliver saline to quickly flush each dose into the patient and also slowly administer saline to prevent the venous catheter from clotting or occluding. The radioactive molecule is displaced from receptor sites by the non-radioactive molecule. This process is repeated and imaged over a period of two to three hours with different concentrations of the hot and cold agents. The images allow rate parameters to be calculated and utilized in a compartmental model to quantify the health of target tissue. Because dynamic nuclear imaging is critically dependent on knowledge of time, there is a need for an individual patient "timer" to alert an operator or a computer system to perform certain actions or to collect data. The timer can range in sophistication from a simple clock, which is started when the patient is injected with one of several medical fluids, and which is set to trigger an alarm or an action automatically or manually at a specified time. A more sophisticated timing device could store information such as: time of injection, radiation level at time of injection, calculated current radiation, patient name, reason for the scan, etc. The timing device could have a communication channel with an injector, physiological monitor, imaging system, or external information management system, either directly to said device or to integrated system controller 110 and thence to the other devices. In addition, the timer device could also be used to store patient-specific physiological information about metabolism and other functions to more accurately determine the optimal injection of drugs, sampling of blood, or triggering of imaging systems. The timer device may be associated with the patient, even to the point of being carried by the patient, clipped to clothing, or strapped to their body. Alternatively, the timer device may exist as an integrated function in integrated system controller 110 or one of the subsystems or devices, for example, imager 130, and the patient can be distinguished by a hospital wrist bracelet with text, bar, RF encoding, or a similar device.

Current practice uses alternate doses of hot (radioactive) and cold (non-radioactive or already decayed) agents or pharmaceuticals separated in time to observe the "competition" for receptor sites as mentioned above. However, because of the limitations of the chemical process and the radioactive decay, there is always some cold receptor material in the hot dose, and the ratio of hot to cold receptor material is changing over time. To provide more consistent input functions and thus enable better assessment of the patient's physiological response and condition, it is desirable to inject consistent doses or ratios of both hot and cold agents. This titration can be accomplished by systems and devices of this invention wherein the hot agent is delivered through a first fluid injector or pump 152(1) and a cold agent is delivered through a second fluid injector or pump 152(2). It is anticipated that a third fluid injector or pump 152(3) be filled with saline to quickly flush fluids from the IV fluid line 153 connected to patient P and for a slow infusion to keep the vascular access open during the procedure. To accomplish this, it is necessary to first measure or know (based upon the properties and reproducibility of the chemical synthesis performed) the starting ratio of hot to cold agent and the activity of the hot agent in the "hot" fluid injector or dose pump 152(1). Subsequently, by knowing the half-life of the isotope being used, the ratio of hot to cold agent can be calculated at the time of any injection. This ratio is used to then calculate the amount of cold agent that should be injected with the hot agent to maintain a constant ratio of hot to cold agent in the dose. Injecting the hot agent "with" the cold agent can be accomplished in many ways, for example, simultaneously injecting the two agents for the same duration, injecting one right after the other at a constant flow rate, alternating partial injections of one and then the other, or any of an almost infinite number of injection protocols that achieves, in a physiologically appropriate timeframe, the condition of presenting the desired concentration of hot agent to the recipient with the desired ratio of hot to cold agent over time of the study.

An example is illustrated via Table 1 (below), using a hot agent with an arbitrary half-life of 40 minutes, an initial starting concentration of 90% hot agent, and a hot agent activity of 9 mCi/ml. For

|   | Time minutes |   | Hot Agent mCi/ml | Cold Agent "mCi/ml" | Hot Agent Volume ml | Cold Agent in Hot Volume mCi | Cold Agent Volume ml | Total volume ml |
|---|---|---|---|---|---|---|---|---|
| 1 | 0 |  | 9.000 | 1.000 | 10 |  |  |  |
| 2 | 20 | hot | 6.364 | 3.636 | 10 | 0.157 | 0.571 | 0.843 | 1.000 |
| 3 | 40 | cold | 4.500 | 5.500 | 10 |  |  | 1.000 | 1.000 |
| 4 | 60 | hot | 3.182 | 6.818 | 10 | 0.314 | 2.143 | 0.686 | 1.000 |
| 5 | 80 | cold | 2.250 | 7.750 | 10 |  |  | 1.000 | 1.000 |
| 6 | 100 |  | 1.591 | 8.409 | 10 | 0.629 | 5.285 | 0.371 | 1.000 |
| 7 | 120 |  | 1.125 | 8.875 | 10 | 0.889 | 7.889 | 0.111 | 1.000 |
| 8 | 140 |  | 0.795 | 9.205 | 11 | 1.257 | 11.571 | −0.234 | 1.023 |
|  | A |  | B | C | D | E | F | G | H | example, this hot agent is to be delivered by a first fluid injector or pump 152(1). A second fluid injector or pump 152(2) contains only cold agent at the same total molecular concentration, for example, 10 mCi/ml. Although the second agent is not hot and thus has no radioactive decay, as is known to those in the health physics field, 1 Curie is $3.7 \times 10^{10}$ disintegrations per second and given the half-life, the concentration is thereby specified and can be calculated. To simplify this example, all concentrations in the Table 1 are expressed in mCi/ml as if all those molecules were hot.

At time 0 (column A, row 1 of Table 1), the drug is prepared with a hot activity of 9 mCi/ml (column B) and a concentration of the hot agent at 90%. Thus, the "hot" agent fluid injector or pump 152(1) contains 1 mCi/ml of cold agent at time 0 (column C). The second fluid injector or pump 152(2) contains cold agent at a concentration of 10 mCi/ml (column D). This concentration does not change.

In this example, by the time the recipient (patient P) is prepared, 20 minute has elapsed (row 2). By this time, the concentration of the hot agent in fluid injector or pump 152(1) is 6.364 mCi/ml (column B). The physician or researcher will set the system to deliver their desired dose of hot agent and the desired ratio of hot to cold agent to the recipient, for this example 1 mCi at a constant hot to cold ratio of 1:9, or what is the equivalent, at a total (hot+cold) of 10 mCi. After entering this information into the system, the system continually or periodically computes the volume from the "hot" agent fluid injector or pump 152(1) and the "cold" agent fluid injector or pump 152(2) to be delivered to the recipient. In this example, at the 20 minute point, 0.157 ml (column E) is delivered from the "hot" agent fluid injector or pump 152(1) and 0.843 ml (column G) is delivered from the "cold" agent fluid injector or pump 152(2). In the "hot" agent fluid injector or pump 152(1) is 0.571 mCi of cold agent (column F).

In this example, the recipient is then imaged for approximately 20 minutes to allow sufficient time for the kinetics of the physiology to be determined. At 40 minutes (row 3), a dose of all cold agent is delivered. The operator has selected the same total dose of 10 mCi for this injection, so 1 ml of fluid is delivered from the "cold" agent fluid injector or pump 152(2) and nothing is delivered from the "hot" agent fluid injector pump 152(1). Again, the recipient is imaged for 20 minutes to collect the data on the dynamics of the physiological displacement of the hot agent by the cold agent. After that time, now at 60 minutes from the creation of the compound, a hot dose is to be administered. While the physician, technician, researcher or other user may select any of the physically achievable desired doses of hot agent and ratio of hot to cold agent, this example assumes that the same dose of 1 mCi hot agent and 1:9 ratio will be used. This can be used, for example, when some outside stimulus is stimulating the recipient. This stimulus can be anything but may be, for example, another molecule, agent, or drug that also competed with the hot and cold agent, or which selectively binds with or incapacitates the hot or cold agent. In this example, at time 60 minutes (row 4) the hot agent concentration has been reduced to 3.182 mCi/ml (column B). To achieve the user's programmed dosing, the system injects 0.314 ml (column E) from the "hot" agent fluid injector or pump 152(1) and 0.686 ml (column G) from the "cold" agent fluid injector or pump 152(2). The dose from the "hot" agent fluid injector or pump 152(1) contains 2.142 mCi of cold agent (column F). At 80 seconds, a cold dose of 1 ml is injected.

At 100 minutes and even at 120 minutes, it is possible to achieve an injection of 1 mCi of hot agent and 9 mCi of cold agent. The system can compute an injection that achieves the operator's desires. However, by 140 minutes (row 8), it is not possible to inject 1 mCi of hot agent with a 1:9 hot to cold ratio. The rote computation shows a negative number −0.234 ml of cold agent to be injected. Of course this is physically impossible, pulling a volume out of the recipient (i.e., patient P) is not desirable and will not remove only cold agent, so the system needs to take or recommend alternative actions. One alternative is to inform the operator while the initial setup is being made of the time when it will no longer be possible to meet their goals of hot and cold agent doses. Then, the operator may take appropriate actions, for example, changing (i.e., shorten) the test protocol segments so that the desired ratio can be achieved over the time of the test. A second alternative is to request that the operator select a different ratio, and optionally to suggest such a ratio. A third option, depending upon the specific molecules being used as the hot and cold agents, is to use a fourth fluid injector or pump 152(4) with a pharmaceutical which selectively binds to the cold agent and eliminates it from interacting in the physiological process under study. If the hot and cold agents are molecularly identical, as can occur with 99mTc studies, this will be impossible to achieve. However, in the case of many other isotopes, such as positron emitters, for example, FDG, the hot agent FDG is chemically slightly different than glucose to which it returns. Thus, it is possible to select and inject an entity that binds with the glucose and not with the FDG. This property is part of the reason FDG is so useful in medical imaging. FDG is taken into the cells in a manner similar to glucose for metabolism but, as it goes through the enzymatic pathway, it cannot be metabolized by one of the cells' enzymes. A molecule with properties similar to this enzyme could be used to selectively bind to glucose and not to the FDG.

In this example, because the hot and cold agents have the same starting total concentrations, the total volume is identical for all injections. This is not a limitation of the system but has been chosen only for simplicity of this example. If the total concentrations were different, the total volume delivered would change as well.

The foregoing integrated systems 100, 100a may be adapted for patient-based dose planning for diagnosis and therapy. Diagnostic imaging with radiopharmaceuticals is currently performed by intravenous administration of a single bolus of drug with a hand syringe. Therapeutic radiopharmaceuticals, such as Bexxar® or Zevalin®, are typically infused at a relatively slow and constant rate over a few minutes. The prescribed radiation dose usually accounts for patient weight but little consideration is typically given to the characteristics of tissue to be imaged or treated. The disclosed integrated systems 100, 100a provide for optimization of radio-isotope injection for diagnostic and therapeutic purposes, customized for individual patients. This disclosure has previously described computer software that implements a kinetic compartmental model. Rate constants and transfer coefficients between compartments are derived from images and physiological measurements. A key to the success of such dynamic models is accurate knowledge of the concentration of radioactivity in tissue and in the blood. This knowledge is even more important for radioisotopes with short half-lives, such as Cu-64, Tc-94, C-11, and Rb-82, because they decay on a time scale comparable to physiological processes. For rapidly decaying isotopes, a kinetic model can be obtained by monitoring three parameters: (1) total dose of radiation injected; (2) instantaneous radiation dose rate; and (3) relative proportion of "hot" and "cold" reagent, often used in receptor blocking studies. The integrated systems 100, 100a described previously are capable of measuring and controlling all of these parameters. These parameters are analogous to parameters of importance in CT or MR contrast enhanced imaging with injected X-Ray contrast agents, namely, total volume injected, flow rate, and contrast dilution. The disclosed integrated systems 100, 100a measure radioactive dose in the blood by automatically or manually withdrawing samples of blood at specific time intervals, as described hereinafter. In addition, it is necessary to know the dose "input function", which is the instantaneous radioactivity rate of the injected radioisotope. Instantaneous radioactive decay rate may be determined most accurately at the patient injection site. A dosimeter or radiation detector located as close as possible to the injection site provides the necessary data, as further described herein. Additionally, such a radiation detector in close proximity to the injection sit could monitor for extravasations or infiltrations, where the injected radiopharmaceutical leaks out of the vein and pools or collects in nearby tissue.

Sequential images (PET or SPECT) provide additional data to estimate the clearance of radioactive drugs from blood and tissue by the kidneys and liver. Images can be used to calculate the rate of uptake and clearance of radioactive drug from chemical receptors in target tissue such as a tumor. Software also accounts for the rate of radioactive decay. Knowledge of the dose input function, blood radioactivity, and other parameters extracted from images and physiological sensors allow a computer system, for example, integrated system controllers 110, 110a, to calculate a customized, optimum injection profile for each patient. This profile may differ significantly from the simple bolus or constant infusion of radioisotopes currently in practice and for simplicity of understanding in the example above. Additional information about blood flow and perfusion of diseased tissue, obtained from CT or MR images can also improve the performance of the computer model. Ultimately, the systems and methods described herein can be applied to the optimization of both diagnostic nuclear imaging and therapeutic drug delivery to targeted tissue.

As described previously in connection with FIG. 1, preparing a radiopharmaceutical agent for administration to a patient involves several steps including creating or obtaining a radionuclide, processing the radionuclide to create an injectable radiopharmaceutical, and packaging a dose, or multiple doses, for later administration to the patient. In the current process for preparing a radiopharmaceutical agent for patient administration, during and between the foregoing steps there is frequent transportation of materials and supplies due to several factors such as immobile equipment, hazardous chemicals and/or processes, economies of scale which make it advantageous to conduct a given process in a certain location, or other constraints on the processes such as short half-lives of certain radionuclides. Moreover, during the conventional process for preparing a radiopharmaceutical agent for patient administration, quality-control tests must be performed at certain instances to ensure the radiopharmaceutical agent is appropriate to be administered to a patient. Among these tests are visual inspections, chromatography, and radioactivity measurements.

After the radiopharmaceutical agent (hereinafter "radiopharmaceutical") has been created, it is typically stored for eventual administration to the patient. Fluid radiopharmaceuticals are frequently stored in individual-dose syringes, individual-dose vials, or multi-dose vials as noted previously. One challenge to creating such individual dose packages is that the radioactive decay inherent to these radiopharmaceuticals will cause a given volume of radiopharmaceutical product to reduce in activity over time. For those radiopharmaceuticals with a short half-life, the change in activity over a few hours can mean the difference between having an imaging procedure with good or poor diagnostic quality. The same half-life sensitivity can be true for multi-dose vials of radiopharmaceutical unless either the administration times and doses are known in advance, or else enough radiopharmaceutical is added to the vial to ensure a minimum activity level for the variety of possible patient radiopharmaceutical administration times from that vial.

In the situation in which the radiopharmaceutical is prepared in a multi-dose format, the multi-dose volume of radiopharmaceutical must be divided into single doses which get administered to individual patients. This dividing of doses may occur at the point of administration if an administration device is able to control the amount of activity administered to the patient. More typically, however, the contents of the multi-dose vials are divided into single doses by a nuclear medicine pharmacist or technologist in a hot lab, as noted previously. The individual radiopharmaceutical dose is then transported to the patient location at which time the entire contents of the single-dose container are administered to the patient.

Figure 3:
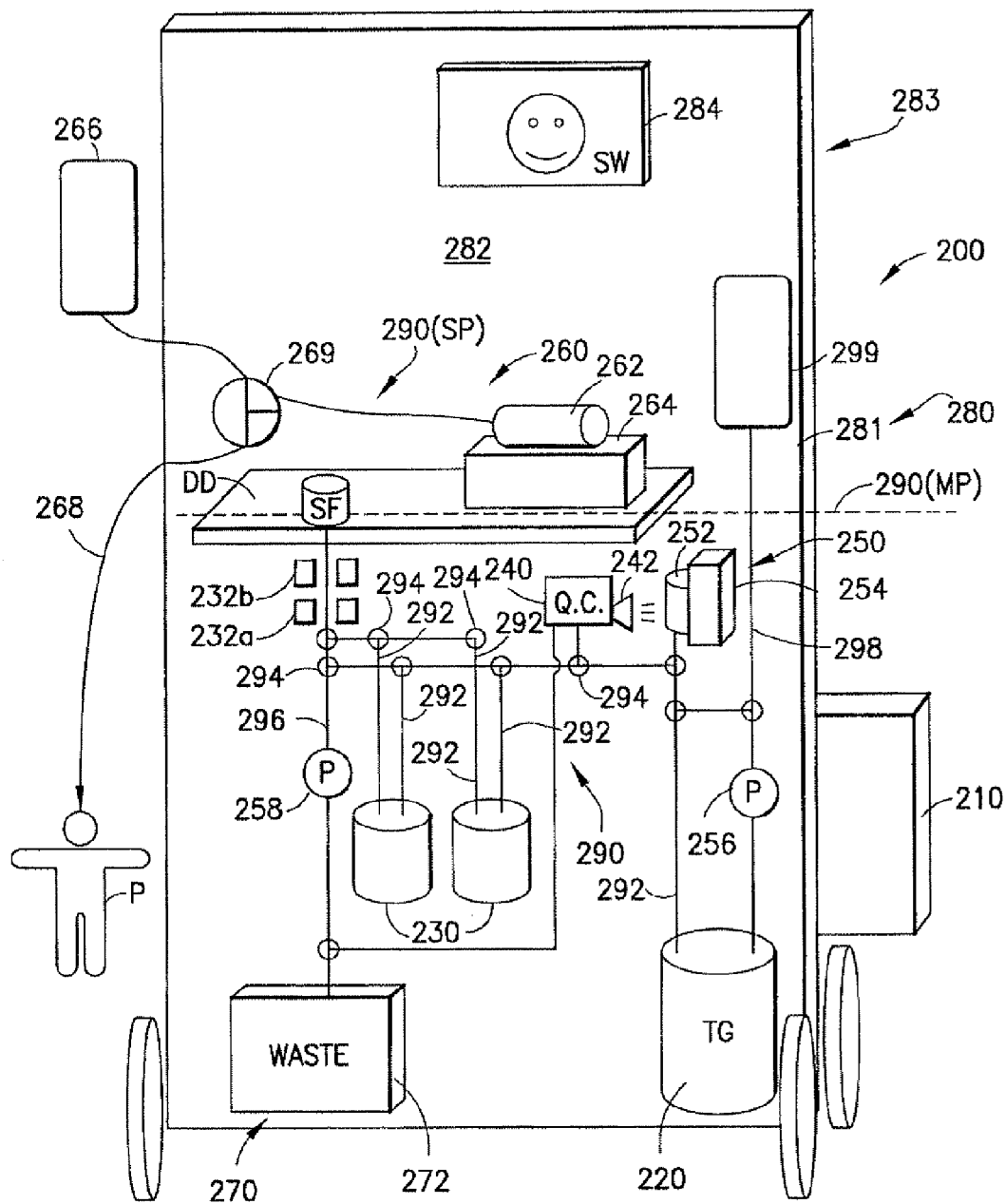
FIG. 3 is a schematic representation of a radiopharmaceutical system including features for radionuclide creation and "chemistry" processing of the radionuclide to a radiopharmaceutical and delivery of the same to a patient.
Figure 4A:
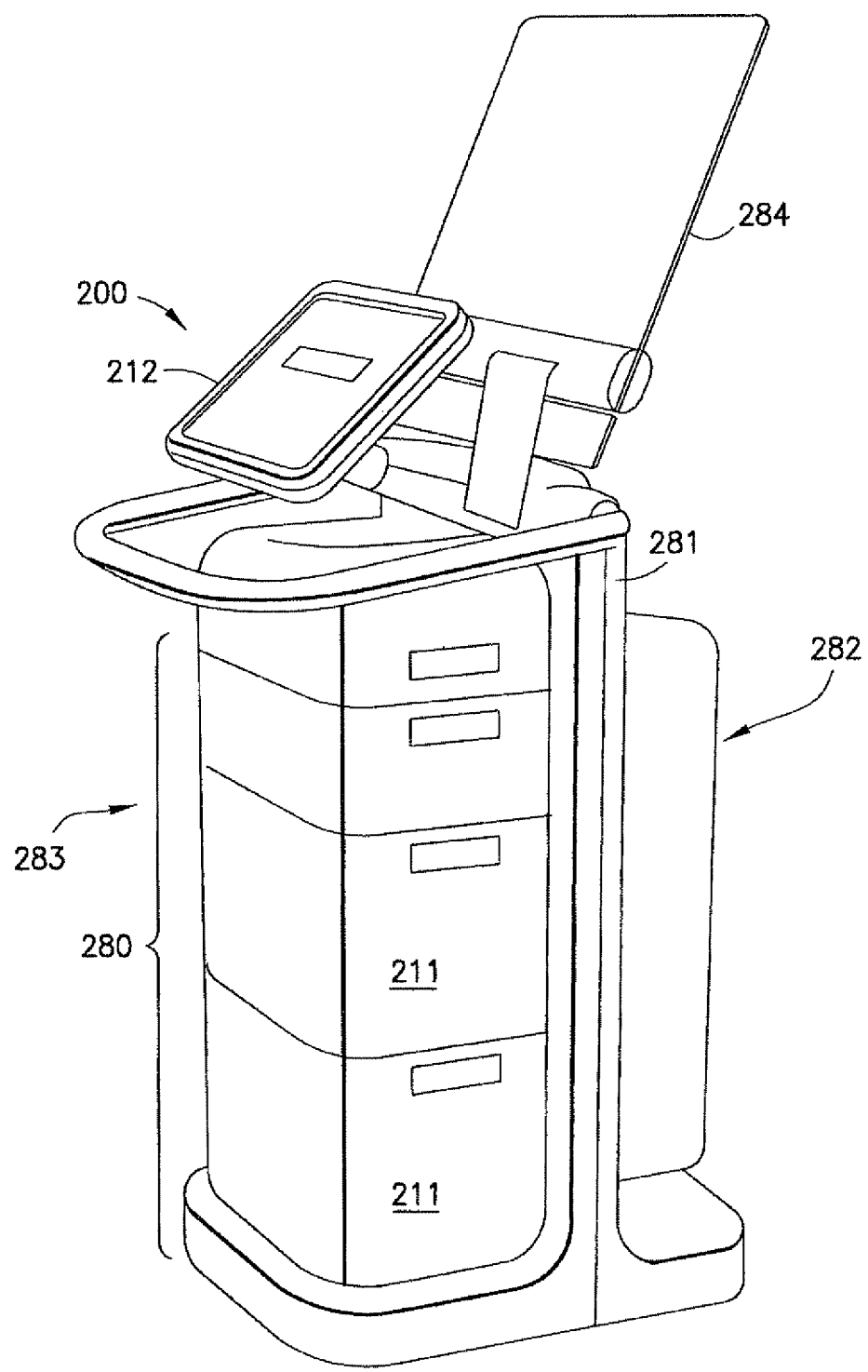
FIG. 4A is a schematic representation of one possible implementation of the radiopharmaceutical system FIG. 3.
Figure 4B:
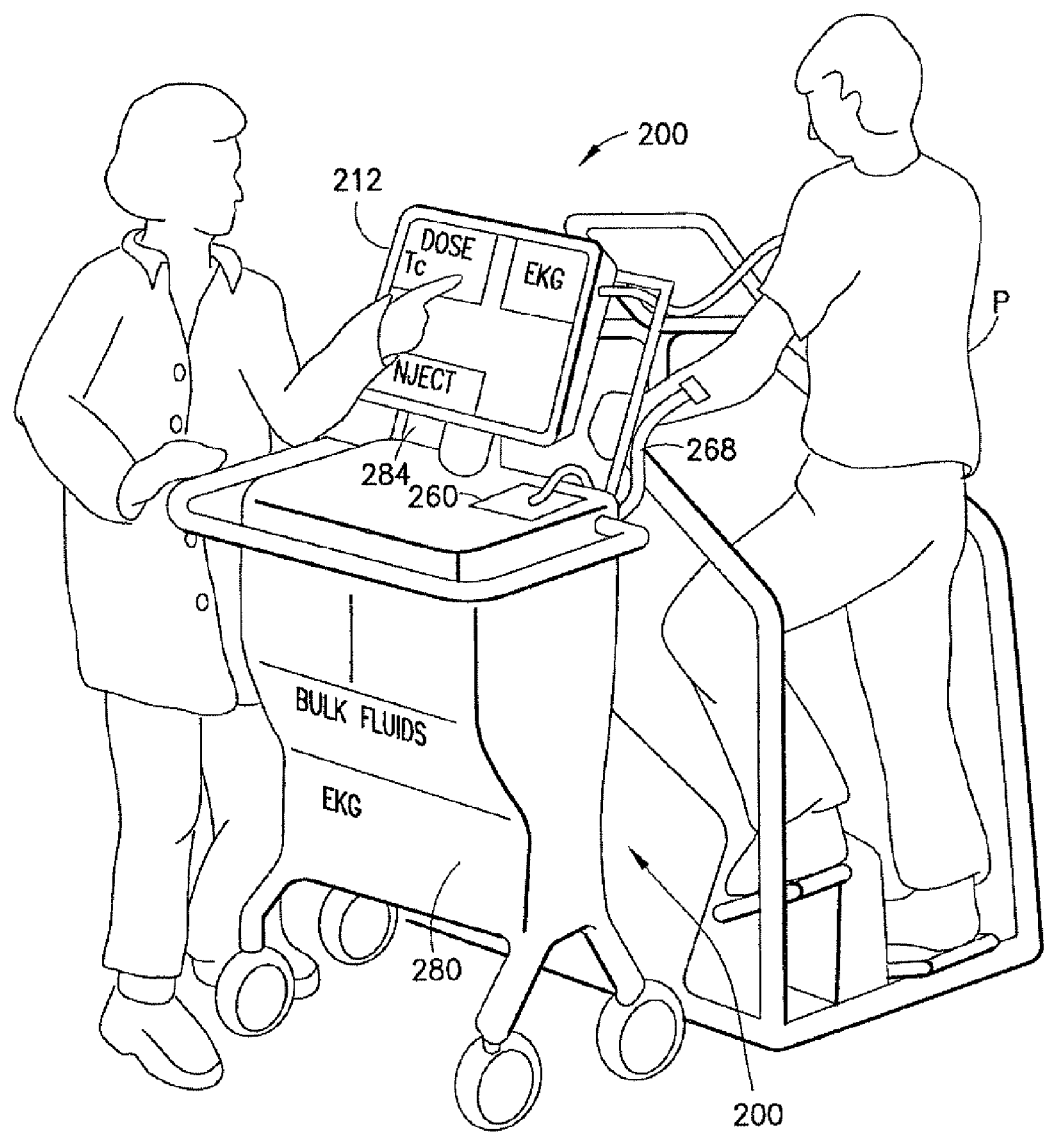
FIG. 4B is a schematic representation of another possible implementation of the radiopharmaceutical system FIG. 3.

In view of the foregoing, it would be advantageous to perform one of more of the steps of FIG. 1, such as creating an isotope (step 10), creating and injectable drug (step 20), and dose preparation (step 30) in a single system. Such a radionuclide creation and "chemistry" processing system 200 is shown in FIGS. 3-4, described hereinafter. Such a creation and processing system 200 is generally adapted to perform the functions of one or both of obtaining or creating a radionuclide and chemical processing thereof to achieve individual radiopharmaceutical doses or multi-doses. Radioactivity monitoring and quality control functions may also be embedded in the integrated creation and processing system 200, for example, in a dosing unit or component thereof. Waste disposal, radiation protection, and patient administration/injection functions are also desirably performed by the "integrated" or universal system 200. FIGS. 4A-4B show views of possible implementations of a stand alone (i.e., non-mobile) or a mobile or portable system 200, respectively, in accordance with the concepts described herein. The following discussion relates to a mobile embodiment of system 200 which, if desired, may be used as part of integrated systems 100, 100a described previously or simply as a creation and processing system 200 to create a radionuclide and process the same into a form suitable for injection into a patient(s). Accordingly, system 200 described herein may be used simply to fill individual containers (i.e., vials, bottles, syringes, etc.) with radiopharmaceutical doses which may be used for individual patients and may comprise, if desired, the capability to deliver such doses to patients. Accordingly, system 200 is not intended to be limited to use in integrated systems 100, 100a described hereinabove but has wider applications to the nuclear medicine field generally.

A desirable embodiment of a portable or mobile system 200, as shown in FIG. 3, is as a portable or mobile system comprised of several subsystems, modules, or components that are selectable to provide a variety of configurations and designs to meet the requirements of a patient treatment facility. For example, an imaging suite in a hospital that receives individual doses of radiopharmaceuticals from a radiopharmacy may choose to integrate only HIS integration, patient administration, waste disposal, and radiation protection modules, whereas an imaging suite which produces its own radionuclides may choose to integrate all the modules into their system. It is recognized that each subsystem to be discussed hereinafter may contain its own embedded sensors, controllers, communication subsystem, and power generation/storage devices. It is well known in the medical field to move functionality among shared resources, such as a system-wide power subsystem, or to leave that functionality as embedded within the subsystem, such as batteries for mobile subsystems. The ability to either embed or move to a shared platform applies to microprocessor-based functionality, graphic user interfaces (GUI's), communications, power, and thermal management such as fans.

In the depicted embodiment, a plurality of subsystems or modules are provided in system 200 and include by way of non-limiting example: a control computer 210; a radionuclide generation module 220; a radiopharmaceutical "chemistry unit" or processing module 230; a quality control module 240; dose extraction module 250; a patient administration/injection module or delivery area 260; a waste disposal module 270; and radiation protection and support component or module 280. Each of the foregoing subsystems, modules, or components will now be described. By way of general reference, the abbreviations used in FIG. 3 are as follows: SW—Shielded Window; SF—sterile filter; DD—Drip Diaper; QC—quality control; TG—Technetium Generator; and P—represented Patient.

Control computer 210 is shown in this depicted embodiment as a single computer, although alternative embodiments could use control computer 210 to coordinate among various embedded controllers for each controlled module as will be appreciated by those skilled in the computer field. Control computer 210 optionally includes a GUI 212 (FIGS. 4A-4B) for displaying relevant data and entering relevant control data and parameters into control computer 210. As one example, the GUI 212 includes a patient organizer that displays, for example, a list of upcoming injections displayed in chronological order. This GUI 212 optionally includes a soft-key labeled with "prepare this dose" next to each patient's procedure information. For example, in a cardiac stress test situation, the GUI 212 would list two procedures for each patient, the stress procedure and the rest procedure, and "prepare this dose" would be selectable for each individual procedure. When the user selects "prepare this dose" for a given procedure, control computer 210 coordinates the actions of the other subsystems or modules to create, for example, an individually labeled syringe or other container with the required dose for that procedure. The GUI 212 also optionally displays a graphic schedule of all active patients in the imaging suite. This facilitates the suite's workflow by displaying, in one place, the procedural steps which are active, their expected duration, and the current status of each patient. An optional attachment is for a wireless handheld device, such as a personal data assistant ("PDA"), to be integrated with control computer 210 to display similar GUI information while at the same time allowing the attending operator the freedom to view that information throughout the imaging suite, rather than just at the GUI 212 of control computer 210.

Control computer 210 has a label printer (not shown) optionally attached. Such label printers are well-known and may be configurable to print human-readable text, bar code or 2D symbology, or a combination of text and symbology as desired. At various points throughout the creation of radiopharmaceuticals it is anticipated that labels would be printed for containers, including vials, bottles, or syringes containing, for example, bulk radionuclides, single dose radionuclide, bulk radiopharmaceuticals, or single dose radiopharmaceuticals as desired and provided by the flexible "modularity" of system 200. The information printed onto the labels may include, for example: amount of radioactivity, volume of fluid, radiopharmaceutical name, patient name or identification number, and expected injection time. System 200 is configurable, via GUI selections, to include other useful information on the labels as desired by the imaging suite. The label printer is also configurable to create labels for patient records including, among other information, patient name, patient identification, prescribed dose, delivered dose, time of dose delivery, attending physician/nurse/technologist, etc. The label printer is also configurable to create shipping labels for Department of Transportation (DOT) approved containers which will be used to transport containers back to remote radiopharmacies or radionuclide generator sites. An optional subsystem is to include an RFID reading/writing subsystem (not shown) in place of, or in addition to, the label printer. Using this optional subsystem, RFID tags may be attached to the various containers used throughout the procedures, and information similar to what would be written on the labels is instead written onto the RFID tag. Another alternative is to place a combination paper and RFID labeler into system 200 (see Zebra R2844-Z printer/encoder from Zebra Technologies, Inc., Vernon Hills, Ill.), which provides attending medical personnel the option of producing both paper labels and RFID tags via configuration settings.

Control computer 210 is also optionally configurable to communicate with an imaging suite's information system, for example, an HIS system. Using this capability enables automatic population of patient information, expected patient injection times, and radiopharmaceutical production schedules for the suite into, for example, the GUI 212. This communication is also able to be used to update the information in the HIS system with actual injection times, volumes, and activity levels, along with any observations during the procedure. The benefit of using this feature is that the attending technologist does not have to switch between the GUI 212 associated with control computer 210 and the HIS system GUI, but rather can populate the HIS system while still at the patient side immediately upon injection. This creates workflow efficiencies as well as eliminates steps which could otherwise lead to data entry errors.

Radionuclide generation module 220, in this embodiment, is identified as a technetium generator (TG) such as a Mallinckrodt Ultra-TechneKow® DTE Technetium Tc99m Generator. However, this identification is for exemplary purposes only. Radionuclide generation module 220 may be selected to meet the intended needs of those employing system 200. Radionuclide generation module 220 produces a sterile, non-pyrogenic isotonic solution of a suitable radioisotope, in the present example Sodium Pertechnetate Tc99m, by periodically drawing saline through a lead shielded column containing molybdenum Mo99. Radionuclide generation module 220 is desirably contained within a shielded compartment of radiation protection module 280 (described herein) in order to prevent excess radiation from leaving system 200. It will be appreciated that other methods are available to produce radioisotopes including nuclear fission (reactor breeding), neutron activation processes, charged particle induced reactions (accelerators/cyclotrons), as well as the foregoing example of a radionuclide generator. Radionuclide generation module 220 may also be provided within an individualized shielded compartment provide as part of radiation protection and support component or module 280.

In one embodiment, radionuclide generation module 220 may produce bulk doses of a radionuclide suitable for the creation of multiple individual doses of radiopharmaceuticals. In another embodiment, the radionuclide generator is "milked on demand," producing only the amount of radionuclide needed for a single dose of a radiopharmaceutical. System 200 is configurable to either type of operation via control computer 210. In either case, a "self-flush" mode may be incorporated that could be triggered by control computer 210 during extended periods of non-use, such as at night. This self-flush clears excess inactive radionuclide material that has converted to the radionuclide of interest, for example, technetium, but has already decayed to its non-radioactive and non-usable state. When self-flush is used, the radionuclide generation module 220 is milked to extract the radionuclide during the period of non-use at a time sufficiently before normal operation, for example, six hours before preparation of the first dose and the fluid containing the radionuclide material is diverted directly to a waste container 272 of waste disposal module 270. Another alternative example includes two (or more) different radionuclide generation modules 220 in the same system 200.

This allows system 200 to be used to create different radiopharmaceuticals for different imaging procedures, as well as to mix different radionuclides which are incorporated in different or identical pharmaceuticals into a compound radiopharmaceutical to support dynamic imaging studies.

For radionuclides which cannot be produced on a system, such as cyclotron-produced radionuclides, radionuclide generation module 220 is designed to be replaced with a container, such a vial, bottle, or syringe, containing the radionuclide produced at an outside facility. This radionuclide container may be for a single dose of radionuclide or for a bulk dose suitable for multiple patient injections. Optionally, the container holding the bulk quantity is tipped at an angle so that the tip of a needle, for example, (through which individual doses are extracted) reaches the lowest point in the container to ensure all fluid is available to be delivered into individual doses. Moreover, multiple containers of radionuclides (beyond a singular container) may also be utilized in place of radionuclide generation module 220. This modular design enables system 200 to be used for a variety of molecular imaging suites and procedures rather than a single site and a single imaging procedure. System 200 is designed for both fluid and data exchanges between radionuclide generation module 220 and radiopharmaceutical "chemistry unit" or module 230. Control computer 210, or individual embedded computers as described previously, is used for coordinating both the data and fluid flows.

Radiopharmaceutical processing "chemistry" module 230 receives radionuclide(s) and creates radiopharmaceuticals through a variety of standard radio-pharmacy procedures. The radiopharmaceutical processing module 230 is contained within radiation protection module 280 (described herein), for example, within an individualized compartment within module 280 to prevent excessive radiation from leaving system 200. Radiopharmaceutical processing module 230 includes, for example, an agitation subsystem, multiple fluid delivery or handling subsystems to move reagents into an output container (i.e., vial, bottle, or syringe), a heating subsystem, and a control subsystem to coordinate a variety of pumps, valves, agitation devices, and heating units. In one embodiment, quality control system/module 240 (described herein) is integrated as a component of radiopharmaceutical processing system or module 230. In another embodiment, the control subsystem of radiopharmaceutical processing module 230 includes software on control computer 210 rather than on a separate embedded controller of this module. In another embodiment, radiopharmaceutical processing module 230 includes a spectrometer to compare the spectrum of the produced radionuclide in module 220 against known spectra of radionuclides and ensure the fluid is the correct radionuclide before creating the radiopharmaceutical. Flexible radiopharmaceutical chemistry modules such as the TRACERLab MX FDG system available from GE Medical Systems incorporate many of these capabilities and can be expanded to incorporate additional capabilities as well. Microfluidic modules are currently being developed and demonstrated, for example, by Hsian-Rong Tseng (Pharmacology UCLA—August 2006, incorporated herein by reference in its entirety) which will lead to small units capable of precisely producing a single dose of radiopharmaceutical, especially on a scale useful for small animal studies.

Radiopharmaceutical processing module 230 is in fluid communication with radionuclide generation module 220 or the containers of radionuclides in the case in which the radionuclide generation module 220 is replaced with delivered container(s) of radionuclide(s), patient administration module 260, and waste disposal module 270. An optional embodiment includes one or more in-line dosimeter or radiation detectors 232a and an optical clarity detector 232b in the fluid output path of the radiopharmaceutical processing module 230 for radioactivity level quality control. Optionally, radiation monitors may be associated with syringes (not shown in FIGS. 3-4) used in radiopharmaceutical processing module 230. In-line dosimeters and radiation monitors may be used throughout system 200 to measure dosages in syringes and like fluid carrying and/or containing components to measure radiation levels throughout system 200 and this information may be communicated to control computer 210 and used as a basis to control operation of the various subsystems or modules. Another variation is to deliver radiopharmaceutical fluid through a solid-state dosimetry subsystem into individual-dose syringes or transport pigs which may be labeled for the individual patient and procedure as is described elsewhere hereinabove. These individual dose syringes (or like containers such as vials or bottles) could be mounted in patient administration module 260 to be filled with radiopharmaceutical and transported for use in another area using a suitable radiation-shielded transport device or system, examples of which are provided herein in connection with FIGS. 14-20. Optionally, the fluid output from radiopharmaceutical processing module 230 is delivered, in real time, to patient administration/injection subsystem or module 260 (described herein) for direct fluid injection into patient P.

In one embodiment, radiopharmaceutical processing module 230 is coordinated via control computer 210 wherein the attending operator chooses to prepare an individual dose. Control computer 210 then coordinates the activities of radiopharmaceutical processing module 230, including such steps as verifying the extracted radionuclide material from radionuclide generation module 220, extracting a specific volume of radionuclide fluid, extracting a specific amount of one or more reagents, heating and/or agitating a container at various points throughout the procedure, and delivering a completed radiopharmaceutical fluid into a container for eventual patient injection. Another option is to use the GUI 212 associated with control computer 210 to facilitate the production of radiopharmaceutical agents by displaying text or graphics indicative of a molecular imaging procedure, for example, cardiac rest procedure, brain perfusion procedure, or FDG PET procedure. The user may then select the upcoming procedure rather than the individual radiopharmaceutical to be used. The radiopharmaceutical that is produced upon selection of an upcoming procedure is a configurable feature of system 200.

The radiopharmaceutical processing module 230 may be contained within a compartment or structure of shielded radiation protection module 280 which could include an airflow management system. This may have two aspects or functions. The first filters the incoming air through a HEPA filter to effectively create a clean hood environment so that it can operate in compliance with the United States Pharmacopiea Chapter 797 requirements for compounding sterile pharmaceuticals. The second aspect ensures that effluent air is filtered via a HEPA filter, ULPA filter, and/or charcoal filters, or similar filtering apparatus before it leaves the compartment to reduce the chance for an aerosol to be released into the room. This filter could contain a built-in dosimeter which sends a signal to control computer 210 which alerts the operator if there is an unexpected release to the air, or to change the filter when the activity level is above a settable threshold value. In another variation for limited volumes, all effluent air is directed to an expandable fluid container, such as an expandable bag, which can be easily removed and disposed of once the radioactivity inside the bag decays to an acceptable level. In another variation, radiopharmaceutical processing module 230 is connected to a facility venting system for venting to the outside.

An agitation subsystem of radiopharmaceutical processing module 230 could be a vibration table or, in another embodiment, fluid agitation may be accomplished via ultrasonic means. Another example of fluid agitation that may be used in radiopharmaceutical processing module 230 is piezoelectric actuators. Another possible agitation inducing apparatus for the agitation subsystem or module includes a single-axis mechanism, such as a motor, gear motor, or four-bar mechanism, to automatically shake the fluid container in a back and forth relatively circular motion. Another embodiment uses a single-axis mechanism, such as a linear slide, ball screw, or four-bar mechanism, to shake the fluid container in an up and down relatively linear motion.

As noted in the foregoing, radiopharmaceutical processing module 230 optionally includes a built-in dosimetry subsystem. This dosimeter is optionally used to measure the radioactivity level of the radionuclides produced by radionuclide generation module 220 and is also optionally used to measure the radioactivity level of the delivered radiopharmaceuticals. Another feature of radiopharmaceutical processing module 230 enables the user to add fluids, such as patient red blood cells, into the radiopharmaceutical process. An exemplary device for this purpose is to integrate the use of features similar to those available on the Mallinckrodt UltraTag® RBC in radiopharmaceutical processing module 230. An optional embodiment radiopharmaceutical processing module 230 includes directing the radiopharmaceutical output of the radiopharmaceutical processing module 230 directly into transport pigs or into modular shipping containers which mechanically interface with system 200, for example, by clipping into a receptacle in the shielded radiation protection module 280 or, alternatively, placing the transport pigs or modular shipping containers in place of patient injection module 260.

Quality control subsystem or module 240 is used to ensure the correct radiopharmaceutical fluid is delivered in the correct quantity (fluid volume and radioactivity level) to the correct patient. One check performed by this subsystem is an optical clarity check which ensures that undesired particulates are not mixed within the fluid. One possible embodiment uses a computer-controlled vision system 242 to accomplish this optical clarity check. This vision system may include a camera, light, and computer software to inspect the fluid for particulates. Complete vision subsystems to accomplish this functionality are available on the market, for example, from Cognex, Inc. Another embodiment includes a camera and light but instead of automatically assessing the clarity via software, images from the camera are displayed on a GUI (the control computer GUI 212 or a separate display), with a button for the operator to push to accept the fluid and a separate button to push to reject the fluid for lack of clarity. Another embodiment replaces the optical clarity check with a light scattering check or a spectroscopic clarity check using a sensor 232b. Another embodiment is for the radiopharmaceutical fluid to be viewable through a leaded glass, shielded window SW with appropriate lighting so the operator can choose to accept or reject the fluid after viewing the fluid through the leaded glass window. Optionally, the leaded glass window can include a magnification lens to facilitate viewing of the fluid. In another embodiment, the radiopharmaceutical processing module 230 places the radiopharmaceutical into a leaded glass vial associated with the quality control module 240, which the operator views for clarity. A still further embodiment includes a magnifying lens built into the leaded glass vial to facilitate the manual optical clarity check.

A further aspect of quality control module 240 includes an optional particulate filter in the fluid path between radiopharmaceutical processing module 230 and an output fluid container, such as sterile filter SF. This particulate filter prevents any particulates that may have been generated during the radionuclide generation process or during the radiopharmaceutical chemistry process from entering the vial or syringe or other container from which the fluid will be injected into a patient. A further aspect of the quality control system or module 240 is to prevent bacterial contamination of any part of the system that is in physical contact with fluid that will enter a patient. There are places and times where connections must be made in system 200 and it is desirable that sterility be preserved at these locations. For example, the technetium generator 220 can be used for many days, but the fluid path elements will probably be exchanged every 24 hours. In this case, it is desirable to sterilize the connection to technetium generator 220 before making a connection thereto. This is commonly done by manually swabbing a rubber septum with alcohol before piercing it with a sterile needle. One embodiment of preventing this contamination is to optionally include an ultraviolet light sterilization subsystem to sterilize connections or optionally selected aspects of system 200. This subsystem flashes UV light for a sufficient time to ensure sterility, for example, ten seconds, before the radiopharmaceutical fluid container is used to inject fluid into the patient. A different embodiment accomplishes the same sterilization using an ozone-generation subsystem. A further aspect of quality control module 240 includes application of antimicrobial surface treatments into the design of the various compartments and surfaces of the system. A further aspect of quality control module 240 includes the optional integration of an alcohol swab into a vial cap, or syringe plunger if syringes are used, at the time the radiopharmaceutical processing module 230 creates the dose. The operator then has easy access to a swab to be used immediately before connecting the vial or syringe with patient administration or injection module 260. Another subsystem of quality control module 240 is to optionally include a crystal photomultiplier, gas chromatography, or other subsystem to determine the specific radionuclide(s) in system 200. The energy spectrum of the fluid in system 200 is then compared with known spectra of a variety of radionuclides to ensure the correct isotope(s) is in system 200. Quality control module 240 communicates its status and any alarms to the operator preferably through control computer 210.

In the foregoing, a method of dosing according to both "hot" and "cold" atoms or molecules was described and can optionally be used in the previously described step of creating an injectable drug 20 (see FIG. 1). If the isotope being used is technetium and an amount of time has elapsed since the generator forming radionuclide generation module 220 has been eluted or "milked", there can be a significant amount of already-decayed technetium in the elutate, which is retained in the generator. Standard practice is to elute such generators at least once a day, with multiple elutations being preferred. If an elutate with a high concentration of "cold" (already decayed) technetium is added to a vial or system for reaction with a radiopharmaceutical, there is competition between the "hot" and "cold" atoms for the binding sites on the radiopharmaceutical. If there is excess radiopharmaceutical, this may be a minor problem. If there is an excess of technetium, it can result in a significant amount of the radiopharmaceutical being bound to a "cold" molecule. As mentioned above, "cold" molecules react physiologically as "hot" ones, and in the case where part of the goal of the procedure is quantification of the physiological response, for example, progression or remission of cancer, this can create uncertainty or error in the assessment and thus diagnosis and possibly in clinical actions taken in the treatment of the patient. Thus, system of 200 could optionally measure the total concentration of an isotope in the elutate using, for example, absorption, scattering, or transmission of non-ionizing radiation, spectroscopic analysis, or mass spectrometry. Combining the total concentration with a measure of the concentration of radioactivity in the elutate through a radioactivity measurement, it is possible to determine the concentrations of both the "hot" and the "cold" isotopes. The system 200 can optionally have a reservoir of a known concentration of cold isotope so that the proper amount of both "hot" and "cold" isotopes may be provided to the synthesis step 20 to enable optimum, known, and/or consistent binding of "hot" isotopes to the desired radiopharmaceutical for use in subsequent steps. This procedure can apply to other isotopes as well. For example, in the creation of 18F in a cyclotron, in the solution that leaves the cyclotron, there is additional non-radioactive fluorine "contamination" from various sources, so there is not 100% radioactive fluorine in the FDG that is produced.

In some situations, only a single dose of a radiopharmaceutical will be needed in a whole day's worth of procedures. In other cases, one more dose may be needed for an unanticipated study. In this case, it would be desirable if the pharmaceutical to be combined with the radioisotope came sealed in a pre-prepared syringe 262, such as may be present in patient administration module 260 as described herein. The pre-prepared syringe 262 could be placed into a syringe pump 264 in patient administration module 260. The radioisotope could be delivered unmodified to the syringe 262 from technetium generator 220. The activity or dose could be measured using in-line dosimeters 232*a*, 232*b*. Since only a single dose is being prepared for a single patient relatively soon before use, it does not have to take place in the desirably more heavily shielded and sterility optimized components comprising radiopharmaceutical processing module 230, unless a specific capability is needed which can only be accomplished in this module 230, or patient administration module 260 is occupied for one patient and the radiopharmaceutical to be produced with the single dose syringe or vial is for a subsequent patient.

The radiopharmaceutical which is produced in radiopharmaceutical processing module 230 and verified as acceptable in quality control module 240 may be contained in a vial or syringe, possibly contained within a transport pig, as an individual dose for an individual patient or as a bulk quantity of a radiopharmaceutical which can be used for multiple patients or procedures. As noted previously, system 200 may be adapted to deliver an individual dose to patient P by producing the dose and then filling it into syringe 262 mounted to an actuating syringe pump 264, as shown in FIG. 3, or other container in patient administration module 260. Syringe pump 264 may be actuated under the command of control computer 210 to deliver the dose to patient P. Thus, syringe 262 and syringe pump 264 may form the patient administration module 260 in the embodiment of system 200 as shown in FIG. 3. In another variation, syringe 262 receives a bulk quantity of radiopharmaceutical fluid from radiopharmaceutical processing module 230.

Moreover, in a further variation showing the flexibility of system 200, radiopharmaceutical processing module 230 may assay the radioactivity level of the dose and optionally print a label for the dose container (a shielded syringe 262) which includes information such as radiopharmaceutical type, fluid volume, radioactivity level, procedure type, and patient information. The label may be in human-readable text, symbology, or a combination of both. A further option is to place the labels in a slide-in, slide-out receptacle on top of a vial as the dose container or on the top of a plunger of a syringe as the dose container instead of on the sides of these containers to make it easier to read the printed labels. Another variation includes the option of writing label information into an RFID device that is included on the dose container. In one embodiment, the RFID tag is located on the syringe so that it is transported with the dose to syringe 262 in patient administration module 260 where it is read by a component in module 260 for further quality control. This syringe 262 can then be placed in a shield and transported and utilized in a remote delivery device as discussed elsewhere herein. Thus, patient administration module 260 according to this variation of system 200 forms a "fill station" for filling appropriate containers with radiopharmaceutical. Accordingly, it should be clear from the foregoing that system 200 is able to perform any desired combination of producing, refining, quality-checking, and delivering radiopharmaceutical fluid to a patient. A final step may be simply to load the radiopharmaceutical into a shielded syringe 262, as an example, and transport the same to remote location where its contents are injected into a patient.

An optional component of patient administration module 260 comprises the use of a biologically inert fluid, such as a saline solution in container 266, in coordination with a fluid path 268 leading to patient P. A control valve 269 may be associated with syringe 262 and saline source 266 to alternately place these fluid delivery elements into fluid communication with patient fluid path 268. Accordingly, saline from saline source 266 may be used to flush fluid path 268 of radioactive fluid. If desired, control valve 269 may be configured so that saline from saline source 266 may be drawn into syringe 262 and syringe pump 264 may then be used to direct a bolus of saline into fluid path 268 (upon proper activation of control valve 269) so that syringe 262 may also be flushed of residual radioactive fluid in addition to the components of fluid path 268 (tubes, hoses, etc.) between syringe 262 and patient P. A suitable arrangement for flushing fluid path 268 of residual hazardous fluid may be found in U.S. Pat. No. 6,767,319 to Reilly et al. previously incorporated by reference.

Another feature of individual dose production capability, wherein patient administration module 260 may be operable as a container "fill station" allows a user or operator to "dial-in", or alternatively to select via GUI 212, a dose quantity (radioactivity level) and press a single "fill" button. After the fill button is pressed, system 200 extracts the selected amount of radiopharmaceutical fluid into an individual dose container (such as syringe 262), optionally prints a label for this container, optionally automatically applies the label to the container, and optionally writes relevant information to an RFID tag on the individual dose container. An optional feature is to write the relevant label and/or RFID information onto a "memory stick," such as a USB memory drive now commonly used with personal computers and associated with the dose container. The individual dose memory stick is transported with the individual dose container and is used subsequently to ensure the correct dose is used for the correct procedure for the correct patient. At each step following the creation of the data on an individual memory stick, later or "downstream" devices are able to update information on the memory stick with relevant information, for example, the time at which the dose was injected into the patient. Optionally, an easy-to-use means is provided to ensure the correct memory stick remains with the correct dose. Examples are receptacles in a syringe shield into which the memory stick easily snaps, a keychain-type device that mates a memory stick to a dose container, and the like. A further option is to label the memory sticks and individual dose containers with symbols, such as numbers, that are readily viewable by the operator to ensure the same symbol is on the memory stick as is on the container. Optionally these symbols are produced by the labeling subsystem of control computer 210. A memory stick may be recycled through a process in which the memory stick is inserted into a USB port of control computer 210 and the like, and a program is selected to erase information off of the memory stick. It is preferred that this program first communicates with an HIS system to upload relevant patient information before erasing the contents of the memory stick.

It should be clear from this disclosure that a variety of dosimetry arrangements may be used to ensure the correct amount of radioactivity level is extracted for each individual dose. For example, a bulk fluid container, for example, in place of technetium generator 220 can be wholly inserted into a dosimeter, such as a commercially available Capintec, Inc. assaying system, and the amount that the radioactivity of the bulk fluid decreases is representative of the amount of radioactivity which was extracted for the individual dose. A different embodiment is to place the individual dose container, for example, a filled syringe 262, inside a dosimeter and measure the amount of radioactivity of the fluid delivered to the individual dose container directly. A non-radioactive fluid is typically used to flush all of the extracted radioactive fluid into the individual dose container before measuring the dose level. An optional embodiment of this feature is to use solid state dosimeters which are incorporated into a syringe or vial shield. Using this embodiment, the shield which contains the solid state dosimeter(s) is connected to a controller which includes a display screen. The display shows the amount of radioactivity measured by the dosimeter(s). This display may also contain a user-selectable list of radionuclides which is used by the dosimeter controller to calculate the radioactivity level based on calibration constants derived for each radionuclide. Multiple dosimeters may be used to provide redundancy and confirmation of leak free fluid transportation. When the correct dose is in a syringe, for example, the syringe shield is disconnected from the controller and transports with the syringe to, for example, a remote fluid injector. Optionally, such patient injection module 260 operates at the patient administering device and can include a similar dosimeter controller and display that the operator can use to verify the activity level of the radiopharmaceutical just prior to injecting the radiopharmaceutical into the patient. An enhancement of the foregoing is to incorporate a writable RFID tag along with the dosimeters, into the container shield. The dosimeter controller is enabled to write the dose information (activity level, radionuclide, time of day) into the RFID tag. This information is optionally used by patient administration module 260 to ensure accurate delivery of the correct amount of the correct radiopharmaceutical.

A further dosimeter embodiment is to place the dosimeter (for example, dosimeter 232*a*) in-line with a fluid delivery line, and control the amount of fluid extracted in real time based on dosimetry measurements of the fluid passing through the in-line dosimeter(s). A preferable embodiment of this implementation is to use solid state dosimeters as the in-line devices. A still further embodiment is to extract a small, known amount, for example less than one milliliter, of the bulk fluid into a container in a dosimeter at the time the bulk fluid is placed in the individual dose production module. The dosimeter measures the activity level of a fluid which has the same radioactive decay rate and initial radioactivity density. Therefore a calculation is made for all individual doses produced from this one bulk amount of radiopharmaceutical. This calculation determines the volume of fluid to extract from the bulk dose based on the radioactivity level of the known volume of sampled fluid and the desired radioactivity amount for the individual dose. The individual dose is then extracted by a fluid delivery means which delivers an accurate volume of fluid into the individual dose container without the need for in-line dosimetry, or for dosimetry of the final individual dose.

Another variation of individual dose production processing uses dose information which is received from the hospital information system (HIS) and automatically produces each individual dose of radiopharmaceutical at the time scheduled for delivery to the patient, for example, using system 200 of FIG. 3. This embodiment includes the option for an operator to select "create this dose now" rather than waiting for the scheduled time. A further feature is to reschedule individual doses via operator interactions. These rescheduling features facilitate changes to patient workflow for those occasions when patients arrive at the imaging suite either early or late, or for when patient workflow and imaging equipment availability support the opportunity to reschedule the injection of radiopharmaceutical into the patient. A still further enhancement includes extracting individual doses into syringes (such as syringe 262) which have distinguishing characteristics, such as different sizes or colors. These distinguishing characteristics help the operator to easily identify the type of procedure this dose is to be used for. For example, the dose may be placed into a red-tinted syringe for the stress portion of a cardiac stress test and the rest dose placed into a blue-tinted syringe. A desirable embodiment of the individual dose production module incorporates dripless syringes which further incorporate reflux valves (i.e., Halkey-Roberts valves) to enable dripless connections to needles or tubing as these syringes are being filled and when they are used for patient injection.

Figure 5:
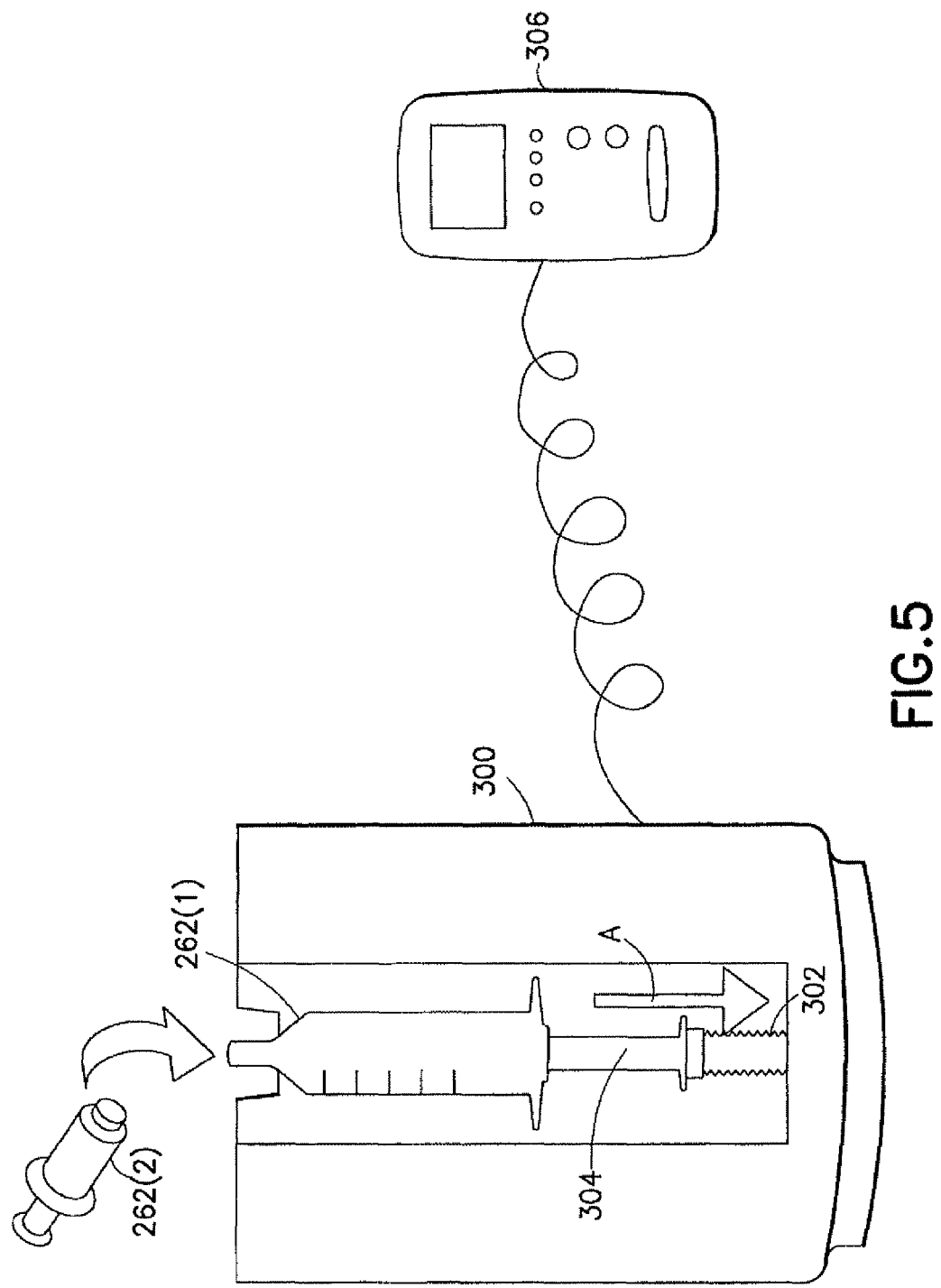
FIG. 5 is a schematic representation an individual dose radiopharmaceutical device for loading radiopharmaceutical agent into a syringe or like container or transferring the radiopharmaceutical agent between syringes or like containers.

In yet another variation, the individual dose production capability includes the ability to create an individual dose syringe using a pre-filled bulk or individual dose of radiopharmaceutical contained in a different syringe 262(2), as shown in FIG. 5. This embodiment includes the process of attaching the pre-filled bulk dose of radiopharmaceutical to a dosimeter 300 in which an individual dose syringe 262(1) is located. Inside the dosimeter 300 is a linear drive mechanism 302 which pulls back on syringe plunger 304 in the direction of arrow A causing the radiopharmaceutical fluid to be drawn into the individual dose syringe 262(1). An option of this embodiment is the ability to control the amount of activity to be drawn into the individual dose syringe 262(1) using a wired or wireless handheld remote operator interface 306.

Figure 6:
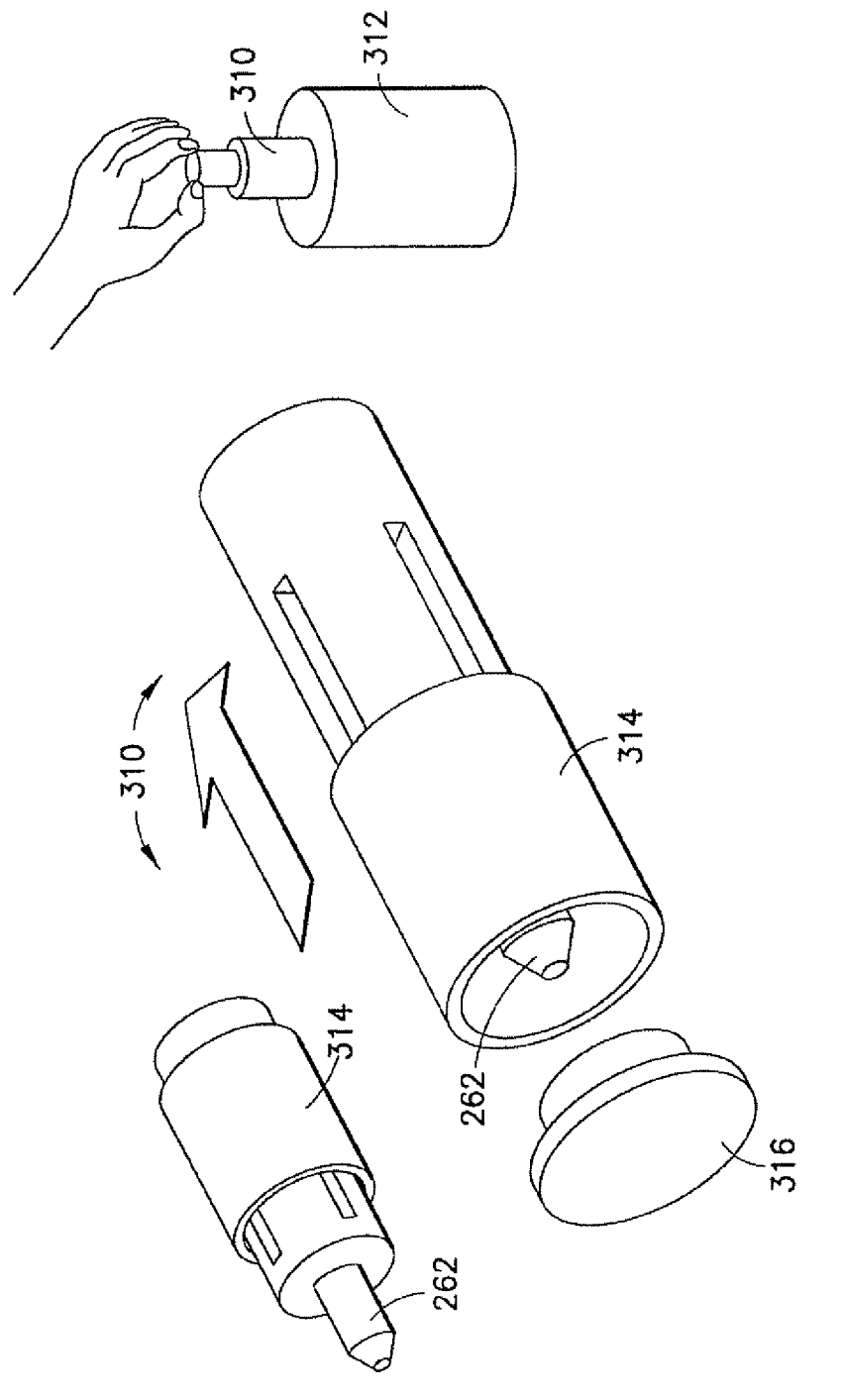
FIG. 6 is a schematic representation of a retractable transport device that may be used to transfer containers of radiopharmaceutical agent to, for example, a dosimeter.

Another embodiment suitable for use in individual radiopharmaceutical dose production and handling situations includes the ability to extract the individual dose into an interim, expandable, storage container such as a bag. This bag is then labeled including, optionally, writing information into an RFID tag attached to the bag. At the time of patient injection, the entire extractable contents of this dose are delivered to the patient in a single bolus by squeezing the expandable bag container. In another embodiment also suitable for use in individual radiopharmaceutical dose production and handling situations, an individual dose syringe 262 is extracted into a retractable pig 310 as shown in FIG. 6. This retractable pig 310 is designed to mate with the top of a typical dosimeter 312. When not mated with the dosimeter 312, the fluid-containing part of the pig 310 can be retracted inside of a telescoping shielded area or portion 314 and a cap 316 placed over the opening to prevent the pig 310 from being extended out of the shielded area 314. When the operator needs to assay the amount of radioactivity in the pig 310, the operator removes the cap 316, mates the pig 310 with the dosimeter 312, and pushes down on the top of the pig 310 to extend the fluid-containing portion into the active area of the dosimeter 312. A suitable telescoping arrangement for use between shielded area 314 and the main body of pig 310 may be adopted from U.S. Pat. No. 4,092,546 to Larrabee, incorporated herein by reference.

As described hereinabove, patient injection module 260 is that part of system 200 which may be used to deliver the radiopharmaceutical directly into patient P. As further noted previously, this module may be an integrated part of system 200 of FIG. 3, in which case system 200 also retains a fluid injection capability and, if made in portable form, may be "rolled" to close proximity to patient P before the patient P is connected to module 260 via patient fluid path 268, typically terminating in a needle cannula or catheter. An alternative configuration, also described previously, comprises patient injection module 260 as "fill station". In this configuration, individual dose syringe 262 is filled in "fill station" module 260 of system 200. Once filled with radiopharmaceutical, individual dose syringe 262 may be removed from system 200 and inserted into a separate patient injection system (such as fluid injection system 700 discussed herein in connection with FIG. 36A). A desirably feature of such a remote patient injection system is for a bulk supply of radiopharmaceutical to be extracted, processed, and loaded into individual dose syringes 262 or like containers in system 200 which, once loaded into a fluid injection system enables delivery of a known, measured subset of the bulk fluid quantity into one or more patients. Whether patient administration module 260 is integrated into a system 200, is used as a "fill station" or potentially operates as a separate, stand alone platform used to inject a radiopharmaceutical into a patient, a desirable feature of the patient injection module 260 is its own modular design. Such modularity includes the ability to include a number of fluid injection devices (such as multiple syringe pumps 264), which enables the injection of 1, 2, 3, or n (n>3) fluids into a patient. For example, system 200 can be used to inject a single radiopharmaceutical such as Cardiolite® into a patient via a single syringe pump 264 or multiple syringe pumps 264 may be provided for multiple fluids. In the embodiment illustrated in FIG. 3 (i.e., a single depicted syringe pump 264), as described previously, patient injection module 260 may include a separate saline delivery fluid path associated with saline source 266 which is used to ensure the total dose of radiopharmaceutical is administered to patient P by pushing saline into patient P after administration of the radiopharmaceutical.

Another feature of the patient administration module 260 includes injection of adenosine, or another cardiac stimulation fluid, into patient P before the radiopharmaceutical is delivered, for example, with the use of a second syringe pump or like device as part of patient administration module 260. When the patient attains a desired heart rate and maintains that heart rate for a sufficient time as determined by the protocol of the procedure, the patient administration module 260 is used to inject the radiopharmaceutical into the patient. This radiopharmaceutical administration may include an automatic flush of patient fluid path 268 with saline to ensure the entire dose is administered to patient P. A further feature includes adding fluid delivery paths in a modular fashion to inject multiple fluids including, for example, stress agents, two or more different radiopharmaceuticals, saline, and additional pharmaceutical fluids. The use of multiple fluid deliver devices or platforms facilitates the workflow of dynamic molecular imaging studies for those studies in which multiple radiopharmaceuticals, and potentially a variety of other medicaments are given to the patient intravenously.

Whether patient administration module 260 is embodied as part of a system 200 or is a distinct or stand-alone platform (akin to fluid injection system 700 discussed in detail herein), it is desired that the actual injection procedure be as simple as possible for the technologist (or other clinical staff member) because this allows that person to focus on the patient and other aspects of the procedure instead of devoting a significant amount of attention to the injection device or platform itself. Therefore, it is preferred that patient administration module 260 (or fluid injection system 700) include a setup procedure which includes obtaining a correct radiopharmaceutical dose and other fluids, priming all tubing to ensure excessive air is not injected, connecting to a patient fluid path 268, and otherwise preparing system 200 for fluid injection. After the setup is completed, it is preferred that patient administration module 260 (or fluid injection system 700) deliver the correct fluids to patient P with a simple, one-button triggering of the injection.

Patient administration module 260 may be controlled to deliver fluid in a variety of ways. For example, the radiopharmaceutical dose can be injected slowly into a continuous saline stream from saline source 266 which is already being injected or infused into a patient. Additionally, the radioactivity at the patient injection site may be measured to confirm that the radiopharmaceutical is entering patient P and is not subject to an extravasation at the injection site. Moreover, the amount of radiopharmaceutical to inject may be determined at injection time as a function of various patient parameters, for example, weight.

Other variations of patient administration module 260 may include arranging shielding which shields the clinical staff from excess radiation exposure from the radiopharmaceutical as well as from patient P after the radiopharmaceutical is injected into the patient P. For example, the components of radiation protection module 280 may be heavily shielded to protect the operator from the radionuclide generation, radiopharmaceutical preparation, and patient administration areas and also from patient P. Radiation protection module 280 may be embodied as a mobile work station (as in FIG. 4B) that includes drawers 211 and possibly internal shelving to hold medical disposables, medical tubing, tape, battery chargers, and the like. FIG. 4B is revealing in another manner as this figure demonstrates that is it is desirable to keep patient fluid path 268 as short as reasonably possible to reduce radiation exposure to people in the area while the radiopharmaceutical is being administered. This can be very important when a dose is being given as a slow infusion or when the radiation dose is high, as in radiotherapy situations. One way to accomplish this result and still provide the flexibility desired is to have any extra tubing contained in a shielded space or compartment in radiation protection module 280.

For those embodiments discussed in the foregoing wherein information is written as a bar code, stored on an RFID tag, written to a USB memory stick, or otherwise encoded and associated with a radiopharmaceutical container, patient injection module 260 (and desirably fluid injection system 700) is designed to read the encoded information. This encoded information retrieval is done for quality control, for example, to write the patient's identification and dose information to GUI 212 and have the attending operator verify that the correct dose is present. This information retrieval is also done to facilitate workflow. For example, the amount of dose to inject into a patient can be a writable parameter and patient injection module 260 (and desirably fluid injection system 700) upon reading that information, can adjust its fluid delivery via computer control to inject the correct amount, or dose, of the radiopharmaceutical and other fluids to patient P. It is preferred that patient injection module 260 (and desirably fluid injection system 700) also includes the ability to write additional information into the encoded information so that the actual injection time and dose information is recorded for future recall and uploading to an HIS system, as an example. In one exemplary embodiment patient administration module 260 is an extension of a commercially available power injector, for example, the MEDRAD, Inc. Pulsar Injector. This commercially available injector is extended by using new syringe embodiments which can cooperate with a syringe shield, such as a lead, lead loaded acrylic, or tungsten compound, around the syringe body. The shield protects from excessive radiation exposure while, at the same time, does not affect the ability of the power injector to deliver fluid at its designed volumes and flow rates.

Another desirable embodiment is to provide a small, possibly even "wearable", remote injector that is small enough to be able to be strapped to a patient's arm when it is connected into patient fluid path 268. Thus, this small, "wearable" injector may accept a syringe, desirably shielded, that is filled by the concepts described hereinabove associated with patient administration module 260. During a cardiac stress test, in which a patient must exercise in order to bring the heart rate up to a certain value, the "wearable" injector may remain attached to the patient's arm. This simplifies the injection procedure because the operator will not have to connect to a moving IV line while the patient is exercising; instead, the connection is already made. Small, wearable infusion pumps are known in the medical art, although they are usually worn on the waist for insulin or other delivery rather than on the arm. An optional feature of this embodiment is the inclusion of a tethered remote start switch that the clinical staff member may use to start the injection when the patient's heart rate reaches the desired value without having to remain at the patient's side. Another optional feature is for the remote start switch to be a wireless start switch which allows the operator the ability to start the injection from anywhere in the room with no cables or wires getting in the way of efficient and safe operation. Another optional feature is to use hydraulic or pneumatic force as the means of controlling the injection. In this embodiment, the syringe(s) containing the radiopharmaceutical and other fluids are held in a shielded device that does not include electromechanical means for injecting the fluid, but does allow connectivity to the patient IV tubing forming patient fluid path 268. The syringe plunger(s) are pushed forward using hydraulic or pneumatic pressure in a fluid line. This use of remote force to push syringe plunger(s) forward enables the initiation and control of fluid delivery from a remote location to further protect clinical staff from excess radiation exposure.

In the embodiment of patient injection module 260 that is incorporated into the design of portable system 200, radionuclide generation and radiopharmaceutical production including all quality control steps are controlled to produce a single dose of a radiopharmaceutical at the time it is needed for patient injection. Patient injection module 260 therefore injects the entire amount of the single dose, with optional other fluids as well, without the need for an additional syringe or vial to contain the radiopharmaceutical fluid between the time it is produced and the time it is delivered. Optionally, radiopharmaceutical production is controlled to produce a bulk quantity of the radiopharmaceutical, and the patient injection module 260 draws the correct amount of fluid (alternatively repeatedly draws fluid until it records that the correct amount of radioactivity has been drawn) and injects the radiopharmaceutical directly into the patient P.

System 200 includes a waste disposal module 270 as noted previously. Waste module 270 includes a waste container 272 into which excess waste fluids are placed so they can be held until the radioactive decay renders them radioactively harmless. Typically, these fluids are held in a secure location in a facility's hot lab and disposed of as bio-waste after sufficient radioactive decay. It is contemplated that different embodiments may support different clinical workflows. For example, a single container may be used for both waste fluids and waste materials (tubing, tape, swabs, and the like). Alternately, two or more waste containers 272 may be used to keep the waste fluids separate from other waste materials. In one alternative, waste disposal module 270 includes a single waste container 272, such as a bag or plastic container, which is housed inside a shielded compartment. At scheduled intervals, or when the fluid level is high, this bag or plastic container can be removed from system 200 to be stored in a safe location to allow time for the radioactive decay to occur. A separate bag or plastic container is then placed into system 200 to collect upcoming fluid waste. Another alternative or variation is to reduce the size of waste container 272 and its associated shielding by using an individual, smaller, waste container 272 that is sized to support the waste anticipated for a single patient procedure. This waste container 272 is then replaced at the same time as disposable patient tubing is replaced for the next procedure. Additionally, this disclosure contemplates the use of a cloth, similar to a disposable diaper that is placed underneath all fluid connection points. This cloth is used to catch any drips that may occur and can be disposed of in waste container 272 that holds waste material. Alternatively or in addition, hand held shielded wipes with disposable absorbent cloths and plastic backing can be made available as part of system 200. Such shielded wipes could also be a holder for the disposable diaper, and can optionally be removed, held by the operator, and used to wipe up drips elsewhere if they occur. Preferably, the absorbent in the shielded wipes contains a colored agent such that the color changes when it absorbs any liquid.

It is preferable that internal fluid path 290 in system 200 be provided in modular or kit form so that set-up is as economical and non-labor intensive as possible. It is also apparent that various adaptations to internal fluid path 290 can be designed to accomplish the functions described herein. For example, internal fluid path 290 typically comprises a plurality of individual fluid lines 292 for conducting fluids between the various subsystems and modules forming system 200. Control of fluid flows within internal fluid path 290 is desirably provided by a plurality of individual control valves 294 which may be individually controlled by control computer 210 and which are further desirably electromechanical devices. A suitable control valve embodiment for the various control valves 294 in internal fluid path 290 are automated stopcock valves. Within internal path 290, there is also provided a main waste conduit 296 leading to waste container 272 and a saline supply conduit 298 connecting a second source of saline 299 to technetium generator forming radionuclide generation module 220 in the embodiment illustrated in FIG. 3. A syringe 252 and associated syringe pump 254 may be provided as part of internal fluid path 290 to form a dose extraction module 250 of system 200. Dose extraction module 250 is used to pull a dose or doses of fluid from technetium generator or bulk vial comprising radionuclide generation module 220 and delivers this fluid via internal fluid path 290 to one or more of the chemistry/processing units forming radiopharmaceutical processing module 230. Additionally, a series of fluid pumps including a first pump 256, such as a peristaltic pump, may form part of dose extraction module and be in fluid communication with internal fluid path 290 to pull saline from second saline source or container 299 and delivers saline to one or more one or more of the chemistry/processing units of radiopharmaceutical processing module 230 and, if desired, syringe 262 in patient administration module 260. A second fluid pump 258 may also be provided in fluid communication with internal fluid path 290 and may be used to flush waste fluids to waste container 272 of waste module 270. Second pump 258 may be used to pull fluid from any of the modules and components of system 200 and deposit waste fluids into waste container 272.

Within internal fluid path 290, a multi-patient fluid path 290(MP) may be provided and comprised by the fluid path elements of internal fluid path 290 located "below" patient administration module or area 260. The fluid conducting elements of multi-patient or multi-use fluid path 290(MP) may be installed, for example, once in the morning and used or "reused" all day. A single patient or single-use fluid path 290(SP) is generally comprised by the fluid path elements of internal fluid path 290 located in and "above" patient administration module 260. These components are changed for each patient P, thereby forming a disposable, single use fluid path. It will be appreciated that single patient or single-use fluid path 290(SP) may be connected by control valve 269 to patient fluid path 268 discussed previously. A suitable "breakpoint" between single patient or single-use fluid path 290(SP) and multi-patient or multi-use fluid path 290(MP) is sterile filter SF. Sterile filter SF may optionally be part of single-use fluid path 290(SP) or multi-patient or multi-use fluid path 290(MP) as desired. Optionally, sterile filter SF may consist of two sterile filters, one of which stays with multi-patient or multi-use fluid path 290(MP) and the second of which is disposed of after each use and forms part of single patient or single-use fluid path 290(SP). Optionally, fluid paths for different radiopharmaceuticals (or other fluids) may each run through a separate line to a separate sterile filter (not shown) in patient administration area or module 260. This variation has the advantage of more assuredly preventing any cross contamination of one fluid into another, but has the difficulty of additional fluid path elements to manage. At the end of the day, as an example, all radioactive liquids are preferably flushed into shielded waste container 272 using second fluid pump 258 so that internal fluid path 290 has little or no radioactivity remaining when removed the next morning. It is desirable to include a radiation monitor, detector, or dosimeter in proximity to waste container 272, optionally inside the shielding of waste container 272 so that the radiation level may be monitored to inform the operator that it is safe to open the waste container 272 and dispose of the waste therein as non-radioactive trash. For FDG, this can generally be after an overnight decay. For technetium and other longer-lived isotopes, it is desirable that shielded waste container 272 be removed from system 200, exchanged for an empty shielded waste container 272, and separately stored for a sufficient time that the waste can be disposed of as non-radioactive waste.

The final module of system 200 is the previously-mentioned radiation protection and support component or module 280. It is obvious that this module includes shielding appropriate for the entire spectrum of radionuclides expected to be used in system 200 and provides the physical support and transport structure (for example, wheeled) for the other modules discussed previously. Generally, this module comprises an upright radiation shield component or divider 281 that divides system 200 into a radioactive pharmaceutical and patient side 282 and an operator side 283. Shield component 281 forms a main support column of module 280. Each "side" of shield component 281 may include additional radiation protection sufficient for the quantity of radioactivity to be contained. The operator will work on the operator side 283 as needed to connect parts of the system 200. During preparation and administration of a dose to patient P, the operator will also generally be on the operator side 283 formed by radiation shield 281 so that the operator is as protected as much as possible, including from radiation emanating from the patient. Doors (not shown) close and shield the patient side 282 of system 200 and can also contain aerosols and direct clean air as described herein. Accordingly, patient side 282 may be compartmentalized (such as formed as a cabinet) for the various radioactive fluid handling components provided on the patient side 282 and which may be individually radiation shielded for components such as technetium generator 220 and waste container 272 as described previously.

One feature of radiation protection module 280 is the use of shielding glass window 284 (SW) and appropriate lighting to enable the operator to view activities and fluid levels in patient administration module 260 and desirably anywhere inside system 200. Alternatively, shielding glass window 284 is replaced with a video camera (with appropriate lighting) on the radioactive or patient side 282 of the shielding glass window 284 with a display monitor on the "outside" radiation protected or operator's side 283 of system 200. Desirably, the camera's pointing direction is designed to be controlled by a simple electromechanical means, such as is popular on commercially-available webcams, which is accessible on system 200 such as proximate to GUI 212. The vertical support aspects of radiation shield 281 are shielded to protect the operator from radiation emanating from patient P and from the radiochemistry aspects of system 200. It is expected that the technetium generator and/or bulk containers comprising radionuclide generation module 220 will remain shielded to provide additional shielding. Bulk containers may remain in transport pigs with only the tops of the pigs being removed for fluid access. If such bulk containers arrive in "smart pigs" as disclosed herein, fluid access is gained without opening the smart transport pig at all. It is further anticipated that the chemistry/processing units forming radiopharmaceutical processing module 230 will also have sufficient shielding around and between them that radiation from one unit will not affect the dosimetry of another unit. This shielding further protects the system operator as well. Another feature of radiation protection module 280 includes the ability to remove part of the system's shielding along with the dose to be injected. This shielding may be in the form of a portable container or, preferably, as a larger portable shield section which protects the system operator from exposure to the fluid contents and also protects the system operator from exposure to radiation after the radiopharmaceutical has been injected into patient P. A further enhancement is that the portable shield is designed to surround the patient's arm in addition to enclosing the radiopharmaceutical dose when the radiopharmaceutical is brought to the patient administration module 260. This sleeve-like shield may remain on the patient's arm during a cardiac stress test procedure and continue to shield the radioactivity even though patient P moves while exercising. FIGS. 4A-4B show exemplary variations of the radiation protection and support component or module 280, particularly alternative constructions of shielding window 284. It should also be noted that there are cases where a radiopharmaceutical is used very infrequently. In this case, the patient treatment facility may purchase a single patient dose, and deliver this dose using the per-patient injection capability of patient administration module 260.

As described previously, integrated systems 100, 100a are capable of delivering one or more fluids, typically liquids that contain drugs such as radiopharmaceuticals, to patient P. In most fluid delivery systems known in the medical field, all the fluids that leave a delivery device, typically a pump, travel down a delivery tube and into the patient. Often, some of the fluid is disposed of or diverted to a waste container. Some known fluid delivery systems, such as that illustrated in U.S. Pat. No. 5,806,519 to Evans, III et al. have the ability to draw back a small volume of fluid so that blood can be pulled into a fluid path element to confirm that a vascular access device is in the target vessel and is not clogged. This fluid is subsequently injected into the patient or discarded. Fluid path elements from a fluid delivery system to the patient can contain several milliliters (ml) of fluid. For example, a low pressure connector tube manufactured by MEDRAD, Inc. of Pittsburgh, Pa. is sixty inches in length and has a nominal inner diameter (ID) of 0.060 inches. Thus, the volume in the tube is about three ml.

When successive deliveries of fluid are made to a patient, saline is often used to separate the fluids or to push the final fluid volume into the patient so that some or the entire dose does not remain in the tubing. Also, the connector tubing between the fluid delivery device and the patient is usually primed with saline as it must be generally free of air or bubbles. Thus, in the normal course of delivery of a medical fluid, several milliliters of saline and other fluids are also delivered to the patient. Where the patient is an adult human or a larger animal, this extra fluid is of no consequence and may actually help promote good hydration. If the animal being studied is a small animal, for example, a mouse or a preterm infant, milliliters of extra fluid can be disadvantageous. Generally a mouse has a blood volume of about two milliliters. Accordingly, there can be significant negative effects if a fluid dose greater than 20% of total blood volume is given. Often the goal is to stay below 10% or 200 microliters (μl) of total volume. Similarly, if blood is going to be drawn for sampling the blood level of a drug or compound, the goal is to stay below about 200 μl or in some cases 100 μl total. If ten samples are to be drawn, then each sample is only 10 μl.

There are several known ways to reduce the volume of fluid in the fluid path between the delivery device and a human or animal. One solution is to reduce the inner or inside diameter (ID) of the connecting tubing. A second solution is to reduce the length of the connecting tubing. However, for maneuverability, connecting tubing length should be at least about a foot in length. If the connecting tubing is filled with a non-radioactive fluid and any radioactive fluids are well shielded, then placing the delivery device relatively close to the subject and the operator does not impose significant health risk to the operator. One type of connecting tubing commonly used in animal experiments is PE 60 tubing which has an ID of 0.030 inches. Thus, a 60 inch length of PE 60 tubing would contain about 700 μl, which is better than 3 ml but still excessive. Even after reducing the length to 18 inches, the volume contained just in the tubing is about 210 μl. One further solution is to prime the connecting tubing with the radioactive drug to be injected, however, this causes the operator to receive radiation dose from the unshielded or minimally shielded connecting tubing while handling the connecting tubing to insert a needle cannula into the animal and while injecting the animal. An alternative is to use even finer tubing. For an 18 inch length, PE 20 tubing has an ID of 0.015 inches and a volume of 50 μl, and PE 10 tubing has an ID of 0.010 inches and a volume of 30 μl. While these are improvements, the volumes injected are not insignificant.

Figure 7:
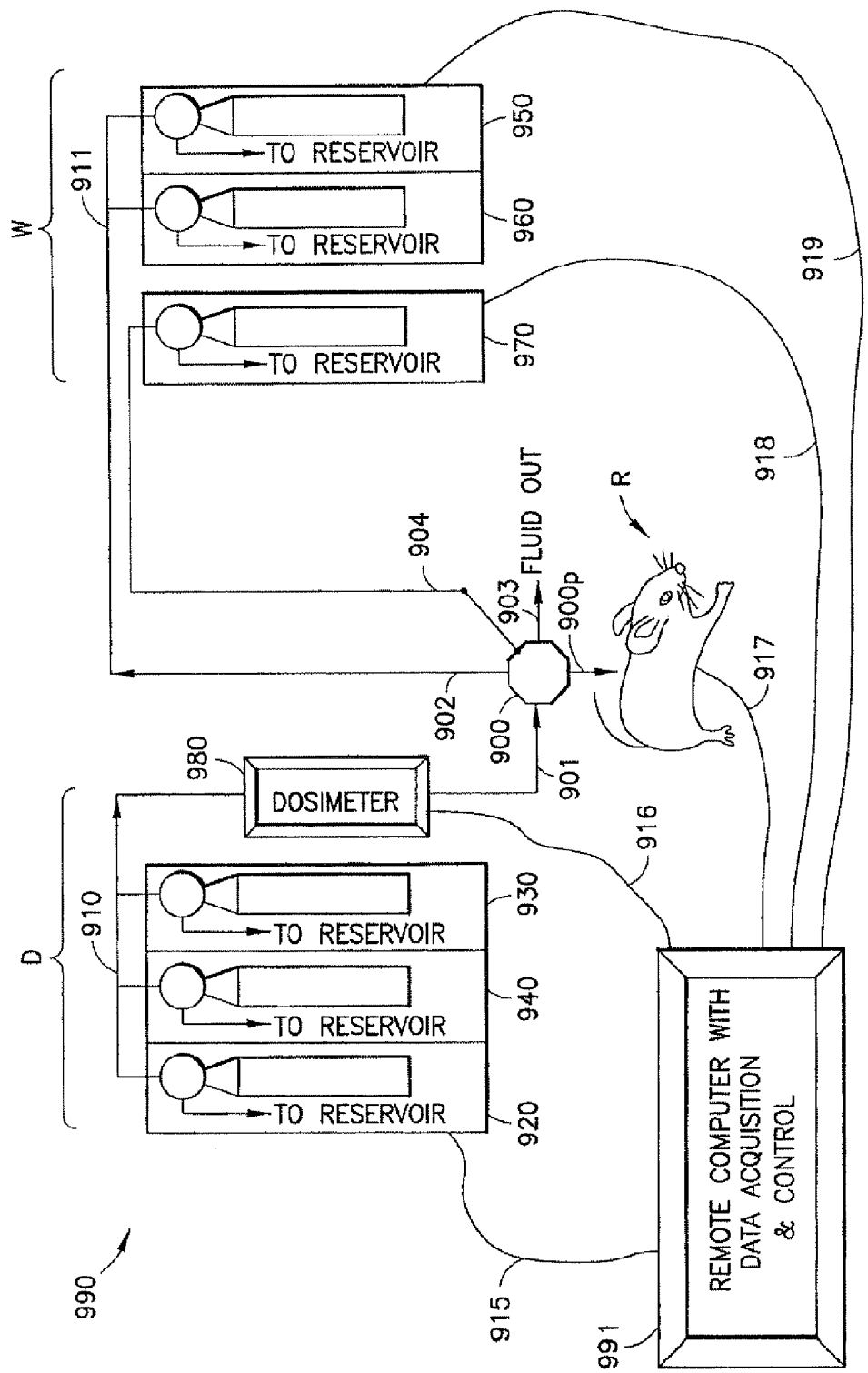
FIG. 7 is a schematic representation of a multi-fluid and multidirectional fluid handling system incorporating a fluid junction in close proximity to a recipient for delivering fluids to the recipient.

Thus, a multi-fluid and multidirectional fluid handling system 990 is now disclosed and shown in FIG. 7 which may be utilized as part of or as the whole fluid handling system 150, 150a in integrated systems 100, 100a discussed previously in connection with FIGS. 2A-2B. As shown in FIG. 7, fluid handling system 990 provides systems and methods and supporting components and devices that enable a preferred, safe, relatively inexpensive priming fluid, such as saline, to be used to prime or fill a fluid delivery path and the fluid delivery lines, typically tubing, forming the same to enable injection of a drug, such as a radiopharmaceutical, with little or no delivery of the priming fluid to a recipient R (human, animal, cell, or a container). Optionally, after the drug is injected, fluid handling system 990 is configured to replace the drug in the delivery lines with the preferred, safe priming fluid to be ready for the next drug injection. This result is achieved by having, for example, two separate fluid paths to a point close to the delivery point, the recipient R, with one fluid path connected to a delivery side, portion, or subsystem of fluid handling system 990 and the other connected to a withdrawal side, portion, or subsystem of fluid handling system 990.

Referring now in detail to FIGS. 7-12, a delivery side or subsystem "D" of fluid handling system 990 has, for example, a saline flush pump 920 optionally connected to an associated fluid reservoir so that it can be refilled, a drug pump 930 optionally connected to an associated fluid reservoir and optionally appropriately shielded for containing radioactive, chemotherapy, or other hazardous substances. A third pumping unit 940 with an associated optional fluid reservoir for refilling is also shown. Additional pumping units can be optionally be added as desired. The series of pumps 920, 930, 940 could be, for example, CavroXLP6000 pumps made by Tecan of San Jose, Calif. The pumps 920, 930, 940 are controlled by microprocessors or computers that are part of pumps 920, 930, 940 and an operator interacts with fluid handling system 990 through an interface, for example, on a computer 991 which communicates with and commands and coordinates the individual fluid pumps 920, 930, 940, other actuatable components or elements, and receives sensor or input measurements, such as heart rate or respiration. Connections between the various system components or elements are shown as lines 915, 916, 917, 918, 919 for illustration and may be any suitable connections known in the computer communications field, such as hard wired point-to-point communications or various networking arrangements, wireless communications, or the transfer of data via a card or some other physical object. Valving to allow controlled fluid delivery and refilling may be done in any number of equivalent ways, for example, automatically via dual one-way check valves, by an electromechanical control affected by control computer 991, for example, pinch valves or rotation of stopcocks, or by manual operation. Electromechanical control is particularly desirable.

Optionally, a dosimeter 980 is provided in fluid handling system 990 at an appropriate location to measure radioactive or chemical dose or concentration of drugs flowing through the fluid path of fluid handling system 990. Alternative sensing methods known to those skilled in the medical fluid delivery art may be used. Fluid from delivery side, subsystem, or module D is conducted to recipient R via a fluid junction 900 connected to first fluid path 901. In a region near recipient R, there is fluid communication between fluid junction 900 and a second fluid path 902. Suitable and exemplary fluid connections comprising fluid junction 900 between first fluid path 901 and second fluid path 902 are illustrated in FIGS. 8-12. Equivalent fluid connections may be developed by those skilled in the medical fluid delivery art.

Second fluid path 902 communicates with a second fluid handling system, generally used as a withdrawal subsystem or module and forming the "withdrawal" side "W" of fluid handling system 990. In this example, withdrawal side, subsystem, or module has two fluid pumps, a first pump 950 that can remove and discard "waste" and a second pump 960 that can also remove a fluid, for example, blood and conduct it into an associated reservoir such as a sample container. Alternatively, second pump 960 can be used to deliver an additional fluid. This is especially useful if the fluid is not compatible in some way or property with that being delivered via delivery or first side or subsystem D.

With the basic components of fluid handling system 990 set forth, operation and associated benefits of fluid handling system 990 will now be described. The following operational steps are merely exemplary in explaining the operation of fluid handling system 990 and should not be considered as limiting. In a first step of this example, saline flush pump 920, for example, a syringe pump, is filled with saline from a reservoir. Likewise, drug pump 930, another syringe pump, is filled with a drug, such as a radioactive version of a drug that bonds with a neurotransmitter receptor, and third pump 940, a third syringe pump, is filled with a non-radioactive version of the same drug. Before connecting fluid paths 901 and 902 to recipient R, a manifold 910 or similar device is filled with saline, and delivery fluid path 901 of fluid path 901 through dosimeter 980 is likewise filled with saline all the way through to a recipient delivery point or element 900p of fluid junction 900 by pumping saline from or via saline flush pump 920. Air in the line is expelled out though this process all the way to delivery point or element 900p. Delivery point or element 900p is typically a small gauge needle cannula. The volume to fill delivery fluid path 901 is either known based upon the specific elements used in fluid path 901 and programmed into control computer 991 or control computer 991 "learns" the fill volume by proceeding slowly or manually under operator observation, and the operator indicates when the air has been fully purged and delivery fluid path 901 is full of liquid. Withdrawal side or subsystem W and fluid path 902 associated therewith is primed or purged of air when waste pump 950 is activated to pull fluid toward this pump, typically at the same flow rate and at the same time as saline flush pump 920. Accordingly, fluid flows down delivery fluid path 901 and up withdrawal fluid path 902 without significant fluid exiting delivery point or element 900p. This synchronous operation is continued until fluid paths 901, 902 are purged of air and full of saline.

With fluid paths 901, 902 purged of air and full of saline, the operator can insert delivery point or element 900p, a needle cannula in most cases, into a vein, other vessel, tissue, or other target in recipient R. Fluid handling system 990 is now ready to deliver drug via drug pump 930. However, delivery fluid path 901 is now full of saline. To avoid delivering all the saline to recipient R, waste pump 950 operates at approximately the same flow rate and at the same time as drug pump 930 so that, as drug flows into delivery fluid path 901, saline flows out or through withdrawal fluid path 902 and no saline is delivered to recipient R. When it is determined, for example, via a sensor, time, or desirably volume calculation that drug has reached fluid junction 900 connecting fluid paths 901, 902, waste pump 950 is stopped while drug pump 930 continues and the intended drug is delivered to recipient R. When the intended volume of drug to be delivered by drug pump 930 has been reached, drug pump 930 is stopped and saline flush pump 920 is activated and pushes just enough saline into delivery fluid path 901, including manifold 910, and delivery point or element 900p, so that all the drug is delivered to recipient R and fluid path 901 is now refilled with saline and an injection cycle is considered complete.

Alternatively in the foregoing, drug pump 930 can continue pumping drug until control computer 991 determines that a desired dose has been delivered from delivery fluid path 901 and into recipient R. At this point, drug pump 930 is stopped. This determination is especially useful if the determination of sufficiency of dose is based upon some sensor or other measurement, possibly in real time, and not just after a predetermined volume has been delivered or predetermined amount of time has elapsed. In this situation, it cannot be known ahead of time when to stop the drug flow and start the saline flush. Delivery fluid path 901 is now full of drug and, if this is a radioactive drug, it represents an exposure hazard for the operator. To eliminate this hazard, drug pump 930 is reversed to return the drug in delivery fluid path 901 to drug pump 930 (if a syringe pump) or the drug reservoir, for example, when drug pump 930 is a peristaltic pump. To avoid pulling blood or other material from recipient R, waste pump 950 pumps fluid out at the same flow rate and during the same time that drug pump 930 pulls fluid in. These two pumps stop when control computer 991 determines that all drug has be returned to drug pump 930 or the associated upstream reservoir. Drug pump 930 then stops, and waste pump 950 can optionally continue for a small volume to flush the drug out of fluid delivery point or element 900p and into recipient R. When delivery point or element 900p is purged of drug, waste pump 950 ceases operation. This last event generally completes an injection cycle according to this alternative mode or operation and the line has again been flushed of the hazardous radiopharmaceutical or drug. Alternatively, once drug pump 930 is stopped and delivery fluid path 901 is now full of drug, the drug in fluid path 901 can be sent to the waste pump 950 by pumping fluid out of saline pump 920 and into waste pump 950 until fluid path 901 is cleared of drug. This reduces the radioactivity in fluid path 901.

It is important that the delivery rates and withdrawal rates be slow enough that cavitation does not occur. Cavitation occurs if inlet pressure to waste pump 950 falls below the vapor pressure of any gas in the saline or of water itself. If this happens, a bubble can temporarily form and some liquid will be delivered into recipient R. Then, when the flow rate decreases, some blood will be withdrawn from recipient R as the bubble collapses. The pressure drops in the fluid path elements of fluid paths 901, 902 can be calculated to a reasonable approximation and then confirmed through experimental measurement to allow designers to select fluid path elements and flow rates sufficiently low to avoid this problem and yet high enough to provide the needed injections.

After imaging recipient R, if desired, "cold" or non-radioactive drug is delivered from pump 940, for example, in the receptor studies described previously. To avoid dumping saline into recipient R, waste pump 950 is again activated at the same flow rate to remove the saline. After the proper volume has been delivered, waste pump 950 is stopped and the non-radioactive drug is delivered to recipient R. Any of the finishing procedures discussed previously may be used to ensure that delivery fluid path 901 is purged of drug and full of saline. After imaging recipient R, if desired, another dose of "hot" or radioactive drug is given at a similar or different dose using the protocol described previously to deliver only the desired fluid to recipient R. Additional doses of "cold" or "hot" drug may be given to complete the study of receptor kinetics. Only the volumes of the "hot" or "cold" drug are delivered to recipient R.

Fluid pumps 920, 930, 940, 950, 960, and 970 can be any generally positive displacement pump or other pump with a sufficiently accurate flow or volume meter so that the fluid flows can be matched as described above. Syringe pumps are schematically shown for exemplary purposes and have the benefit of potentially incorporating the total needed reservoir volume for delivery to recipient R. Peristaltic pumps, as noted previously, are suitable alternatives and have the advantage of being relatively easy to prime. A disposable gear pump, as discussed in U.S. patent application Ser. No. 11/403,119, filed Apr. 12, 2006, and entitled "Fluid Delivery System with Pump Cassette" is another possible pump device for fluid pumps 920, 930, 940, 950, 960, and 970.

Similarly, fluid junction 900 may have many embodiments as illustrated in FIGS. 7-12, with various features that meet the general needs. FIG. 8 shows a fluid junction 900 achieved by having fluid junction 900 end in a needle cannula forming delivery point or element 900p of smaller outside diameter (OD) than the ID of delivery fluid path 901. Delivery point or element 900p is simply inserted into the flexible tube forming delivery fluid path 901. This arrangement works especially well if the tubing forming delivery fluid path 901 is soft tubing such as silicone tubing. The junction formed by insertion of a needle cannula in the tubing of delivery fluid path 901 can be held in place with a dab of medical grade adhesive or even "super glue" for animal use. FIG. 9 shows a similar process used for the addition of a third line 903 which can be used for sampling blood or fluids or delivering additional fluids. FIG. 10 shows a separate T-piece connector 905 into which are press-fit tubing elements forming delivery fluid path 901, withdrawal fluid path 902, and delivery point or element 900p (needle cannula). The tubing components may be solvent bonded into the T-piece connector 905, or a medical grade adhesive can alternatively be used. FIG. 11 illustrates an alternative connector 905' which holds three fluid conduits (901, 902, 903) in side-by-side, generally parallel relationship. This arrangement has the benefit of providing a handle structure for manipulating delivery point or element (needle cannula) 900p for insertion into recipient R. Again, solvent bonding and medical grade adhesive are two exemplary methods of securing the arrangement of FIG. 11.

It is also possible for fluid junction 900 to be a stopcock that can be rotated remotely, for example, by an electromagnetic stepper or a hydraulic actuator as illustrated in FIG. 7. A hydraulic actuator has the benefit of being able to operate in close proximity to an MRI system. The hydraulic actuator is operated by a hydraulic pump 970 connected via a hydraulic fluid line 904 to fluid junction 900. Hydraulic pump 970 is controlled by the control computer 991. Pinch valves, either hydraulic or electromagnetically actuated, may also be used.

As noted in the foregoing, fluid handling system 990 may be used to collect a blood sample. A method of obtaining a blood sample is to connect a conventional blood sampling system to fluid conduit 903 (FIG. 9) and coordinate its operation with that of system 990. Another sampling arrangement, involves two additional syringe pumps and a tubing set with sufficient volume to contain all the blood samples for one recipient R. A sample of blood is drawn into a sample holding tubing set or line by activating a first pump (not shown) to withdraw blood from the recipient R. When a sample of sufficient volume is withdrawn, a second pump (not shown) is activated to inject a viscous fluid into the sample holding tubing line and is injected at the same rate that first pump is withdrawing fluid (i.e., blood). Thus, the sampling of blood is stopped and a "slug" or segment of viscous fluid is used to separate successive blood samples. One viscous fluid that can be used is X-ray contrast, for example, iso-osmolar contrast such as Visipaque® manufactured by Electric Healthcare (Amersham, Inc.). When it is time for another blood sample, the process is repeated. After all the blood samples are taken, the sample tube line is removed and the separate blood samples are dispensed into appropriate containers, such as blood collection tubes, for analysis. An alternative to a viscous liquid is air, carbon dioxide, or another gas. The bubbles effectively separate the different blood samples. This arrangement allows samples of a few microliters to be drawn. If desired, after a sample is drawn, an equal volume of saline can be administered to the animal to make up for the volume withdrawn.

As noted in the foregoing, fluid handling system 990 may be used to collect a blood sample. A method of obtaining a blood sample is to connect a conventional blood sampling system to fluid conduit 903 (FIG. 9) and coordinate its operation with that of system 990. Another sampling arrangement, involves two additional syringe pumps and a tubing set with sufficient volume to contain all the blood samples for one recipient R. A sample of blood is drawn into a sample holding tubing set or line by activating a first pump (not shown) to withdraw blood from the recipient R. When a sample of sufficient volume is withdrawn, a second pump (not shown) is activated to inject a viscous fluid into the sample holding tubing line and is injected at the same rate that first pump is withdrawing fluid (i.e., blood). Thus, the sampling of blood is stopped and a "slug" or segment of viscous fluid is used to separate successive blood samples. One viscous fluid that can be used is X-ray contrast, for example iso-osmolar contrast such as Visipaque® manufactured by Electric Healthcare (Amersham, Inc.). When it is time for another blood sample, the process is repeated. After all the blood samples are taken, the sample tube line is removed and the separate blood samples are dispensed into appropriate containers, such as blood collection tubes, for analysis. An alternative to a viscous liquid is air, carbon dioxide, or another gas. The bubbles effectively separate the different blood samples. This arrangement allows samples of a few microliters to be drawn. If desired, after a sample is drawn, an equal volume of saline can be administered to the animal to make up for the volume withdrawn.

As described in the foregoing, fluid handling system 990 is associated with one animal recipient R for the duration of a sophisticated study. Alternatively, a slightly simplified version of system 990 can be used to provide doses to successive animals with only the need to change some of the elements of fluid paths 901, 902 as desired based upon the sterility needed. It may be sufficient in most cases that only the needle 901p needs to be changed. The isolation of the reusable portion from the per-recipient portion can be improved by including a slit silicone rubber disk 906, 906' similar to those used at the end of central venous catheters and upside down dispensing bottles. Using the split silicone septum also provides the benefit that there is no fluid flow to or from the patient until the pressure differential is sufficiently high to open the septum. It may be desirable that detailed operation of fluid handling system 990 as to the details of significantly reducing or eliminating the delivery of priming fluid to the recipient R is generally transparent to or hidden from the attending operator, although this may be under operator control or influence as necessary, for example, during the initial setup of system 990. The operator only needs to specify the volume or activity of the fluid to be delivered to the recipient, the coordinated operations of the waste and other pumps are not selected or affected by the operator's choices.

Figure 13:
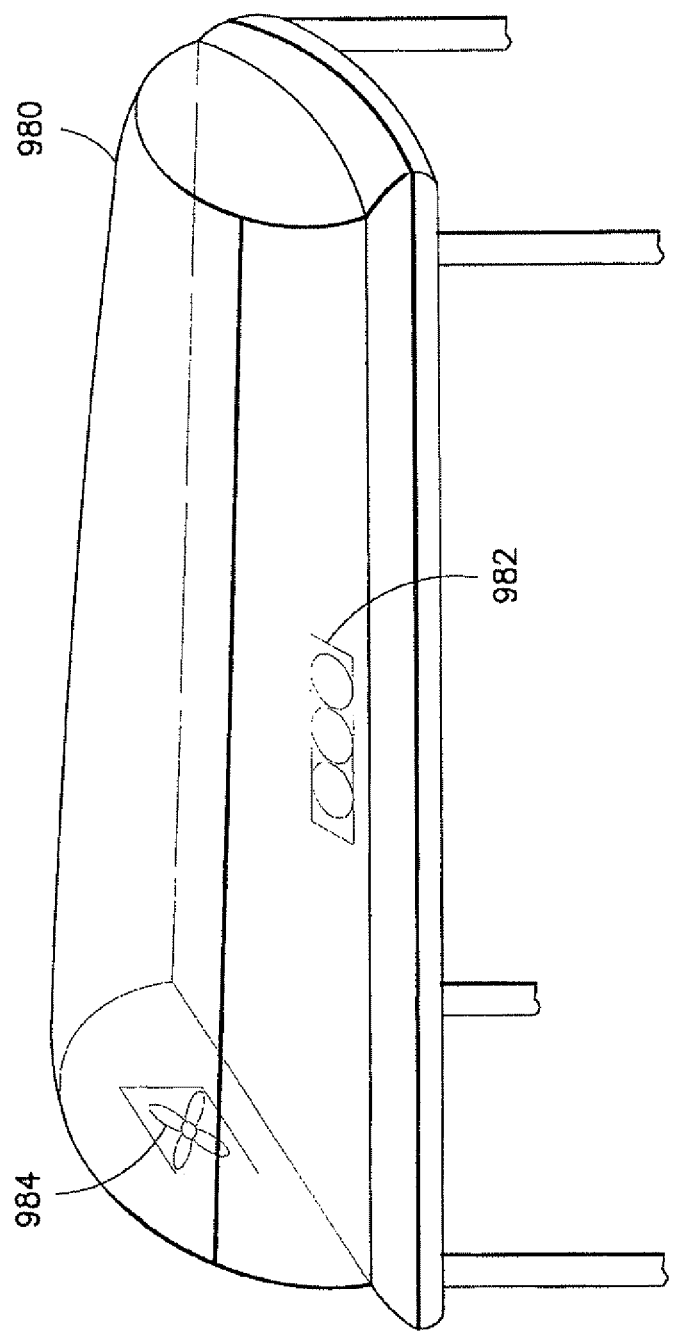
FIG. 13 is a perspective view of an embodiment of a patient shielding system.

After injection with a radiopharmaceutical agent, a patient or recipient is a potential source of radiation harmful to attending personnel. In normal practice, as mentioned previously, after injection with a radiopharmaceutical agent, a patient is usually kept in a shielded room isolated from other patients and attending personnel for about an hour until the radiotracer has distributed sufficiently for imaging. A possible alternative to current practice is to provide a patient enclosure system 980 that is shaped and configured to enclose the patient's body or major portions thereof. The patient enclosure may be portable and would eliminate the need for a separate shielded room. Patient enclosure system 980 is envisioned as a shielded chamber that keeps the patient relatively immobile and free of visual or auditory stimuli. Additionally, monitoring devices may be built into the enclosure to monitor patient vital signs such as heart rate, temperature, respiration, and metabolic rate (by monitoring respiratory gases). An example of a patient enclosure system 980 according to the foregoing concept is shown in FIG. 13, wherein monitoring devices 982 or openings for permitting patient (vital sign) leads to be passed to the exterior of the patient enclosure system 980 are provided on the body the patient enclosure system 980. As shown, it is envisioned that a ventilation device 984, for example, exhausted directly to outside air, may be provided for the comfort of the patient. Patient enclosure system 980 may resemble in size and appearance a conventional tanning booth.

As noted earlier in this disclosure, radiation shielding has considerable importance in the nuclear medicine field. It is well-known, for example, to use shielded containers known as "pigs" for handling and transport of radiopharmaceutical containers (bottles, vials, syringes etc.) and use shielded syringes to remove the radiopharmaceutical from containers and administer the same to individual patients. This disclosure now turns to a discussion of embodiments of a shielded container or pig for containing and transporting radiopharmaceutical containers but which additionally may incorporate other features such as the ability to measure radioactive dosage emanating from the radiopharmaceutical container. This improved shielded container, housing, or pig enhances safety by minimizing contact time for medical personnel, ease of use in transporting radiopharmaceuticals and preparing the same for administration to a patient, and, further, reduces the cost involved in handling radioactive fluids by integrating dosage measurement with the transport function of a shielded container in one embodiment. As will be clear to one skilled in the art, examples of radioactive fluids which may be transported by the "enhanced" shielded container discussed herein include FDG, technetium, thallium, etc. which are intended for injection into patients in their form stored within the "enhanced" shielded container or after further dosage preparation occurs, for example, at a patient treatment facility.

Referring to FIGS. 14-24, various embodiments of radiation-shielded containers, housings, or pigs for containing and transporting radiopharmaceutical containers (vials, bottles, syringes, etc.) and other purposes are illustrated. The various embodiments of a radiation-shielded container (hereinafter "RS device") incorporate, for example, an ability to measure the radioactivity of the radiopharmaceutical contained within a transported container, which again may comprise a vial, bottle, syringe and like container customary in the nuclear medicine field. In one example, measurement may be accomplished by a radiation dosimeter or detector housed within the RS device. This dosimeter may be calibrated for, for example, 511 keV gamma photons, thereby eliminating the need for independent large, bulky, and expensive dosimeters in the "hot lab" of a patient treatment facility to measure radioactive dosage present in the individual container containing the radiopharmaceutical substance or agent (hereinafter "RP container"). In an alternative arrangement, a radiation dosimeter may be adapted to clip onto tubing (not shown) extending from the RS device and through an opening in the shielding of the RS device and which connects to an intravenous line associated with a patient. An additional feature of the RS device includes the ability to engage or interface, for example, mechanically, with fluid handling system 150 described previously and, further, with the respective fluid injectors 152 associated with the fluid handling system 150. Another feature of the RS device includes the ability to allow accurate doses to be drawn from the RP container housed within the RS device into a small diameter syringe.

Figure 15:
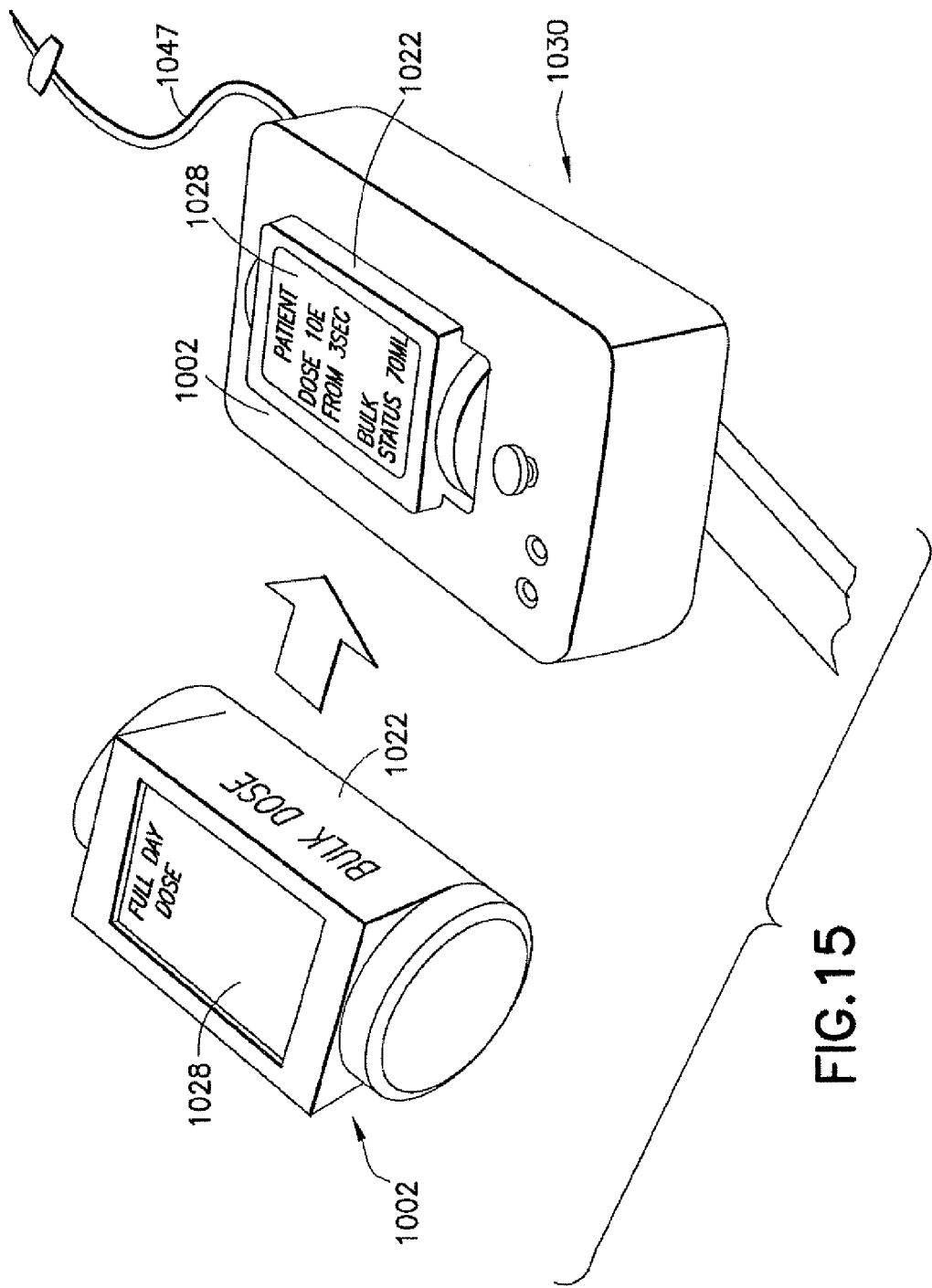
FIG. 15 is a schematic representation illustrating a possible implementation of the system shown in FIGS. 14A-14C.
Figure 16:
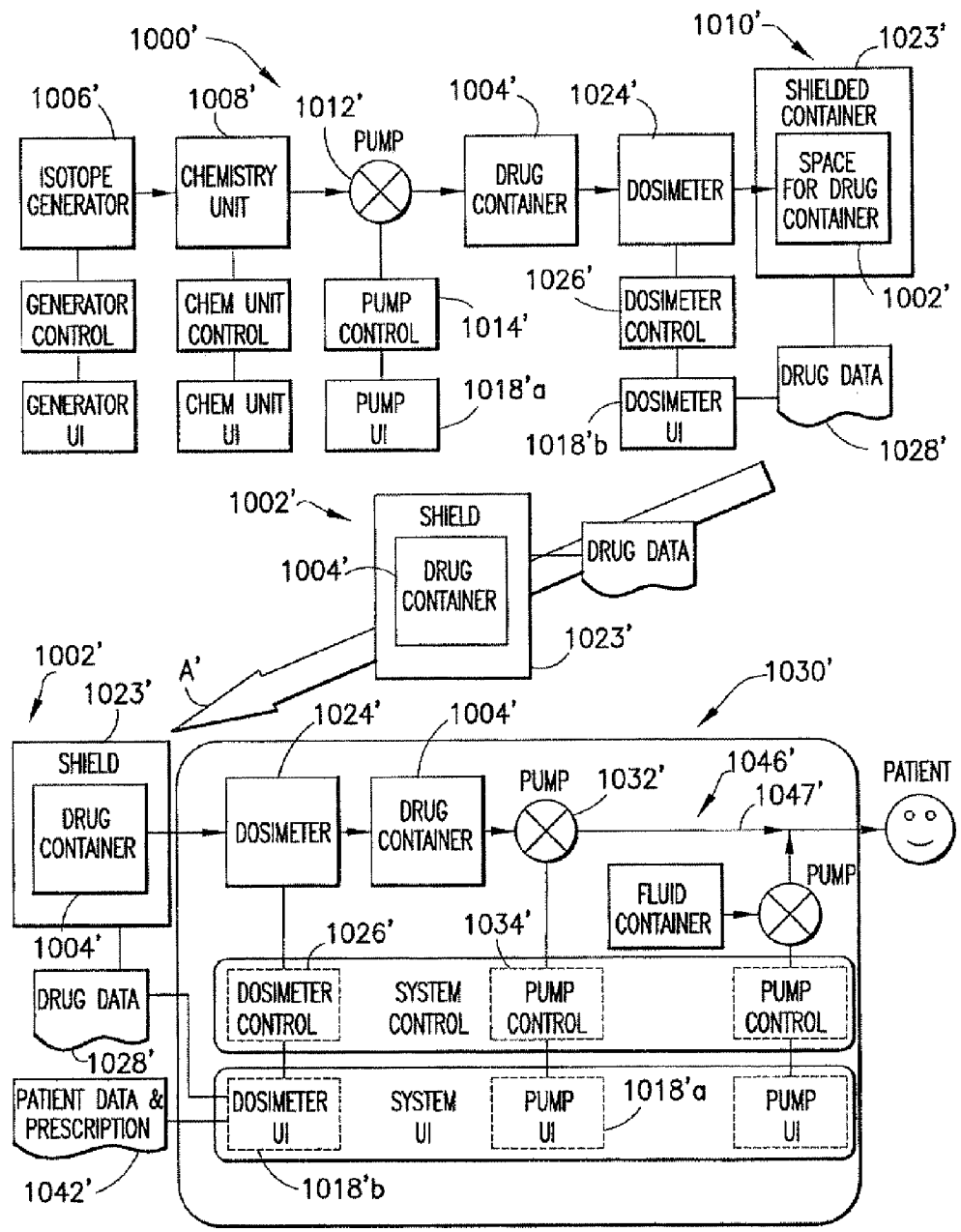
FIG. 16 is a schematic representation of another embodiment of the system for generation, preparation, transportation and administration of fluid radiopharmaceutical substances shown in FIGS. 14A-14C.

In a typical prior art radiopharmaceutical delivery situation, medical and/or transport personnel are required to handle a drug container at several steps along the delivery of a radiopharmaceutical agent to a patient which increases radiation exposure risk to these personnel. The information about the drug in a shielded container is generally conveyed on a paper label, bar code, or optionally in a magnetic or electronic medium. The information is manually entered or transferred into a laboratory information system. The dose is manually confirmed before injection. Separate pumps, if used at all, are manually programmed based upon the prescription for the patient or protocol for the research to deliver the drug. In FIGS. 14-16, an embodiment of a system 1000 for the generation, preparation, and administration of fluid radiopharmaceutical substances to human and animal subjects is schematically illustrated employing an RS device 1002 according to one embodiment. System 1000 provides a distinct improvement over the prior art radiopharmaceutical delivery situation just described by drastically decreasing the exposure time of medical and other personnel to radiopharmaceutical agents. Within system 1000, RS device 1002 encloses and houses an RP container 1004 for transport and other purposes pursuant to aspects of the invention contemplated by this disclosure. As shown, RS device 1002 is generally a shielded container or housing that encloses and houses RP container 1004 for transport as well as having the ability to obtain dosimetry data and record data associated with the drug (radiopharmaceutical) contained in RP container 1004 and, further, data associated with RS device 1002 generally. The modularity of RS device 1002 greatly minimizes or even eliminates radiation exposure risk to attending personnel which may include radio-pharmacists, transport personnel, clinicians, etc. Specific details of RS device 1002 are provided hereinafter. FIG. 15 illustrates a possible exemplary configuration of RS device 1002 for use in radiopharmaceutical system 1000.

Figure 14A:
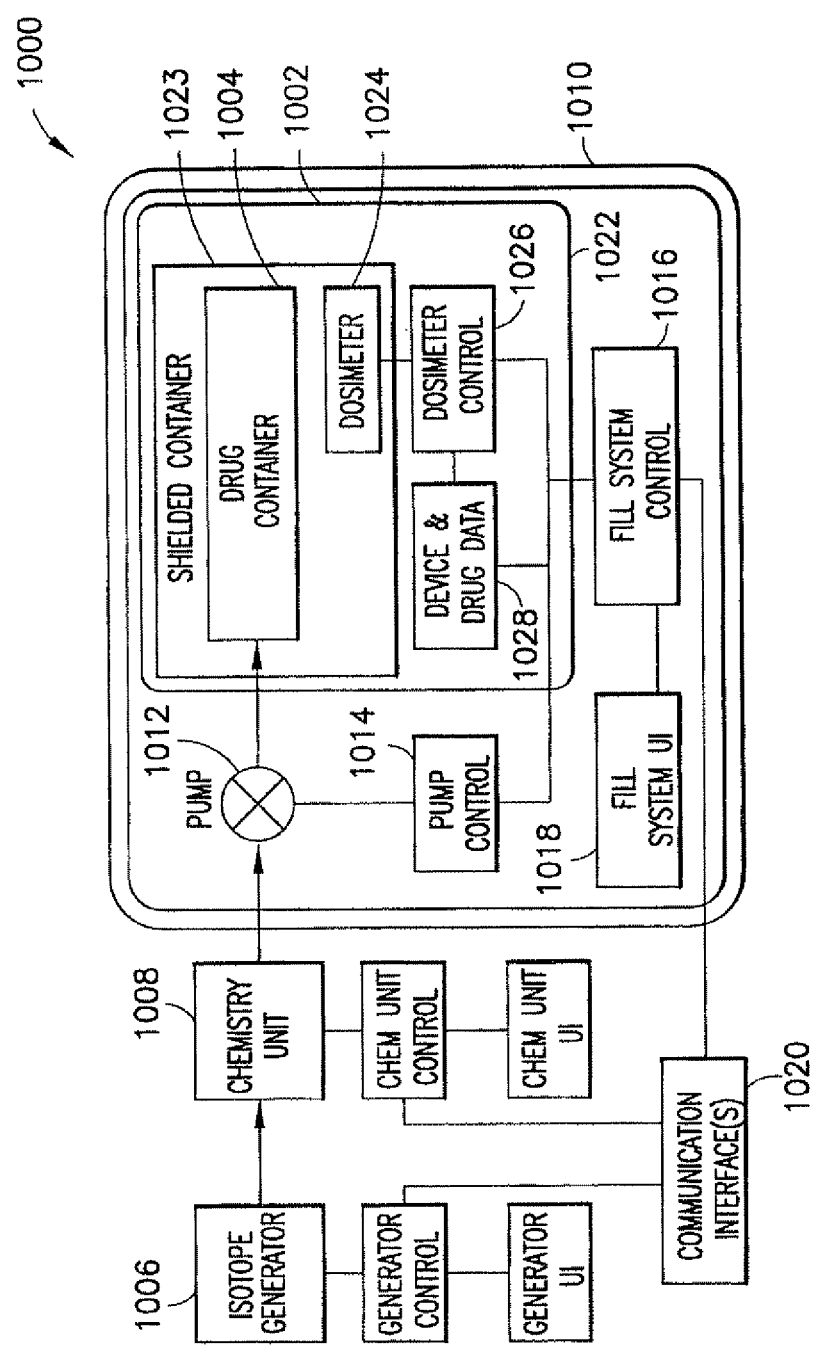
FIG. 14A is a schematic representation of a system for the generation, preparation, transportation, and administration of fluid radiopharmaceutical substances that incorporates a modular and transportable radiation-shielded transfer device for radiopharmaceutical containers.
Figure 14B:
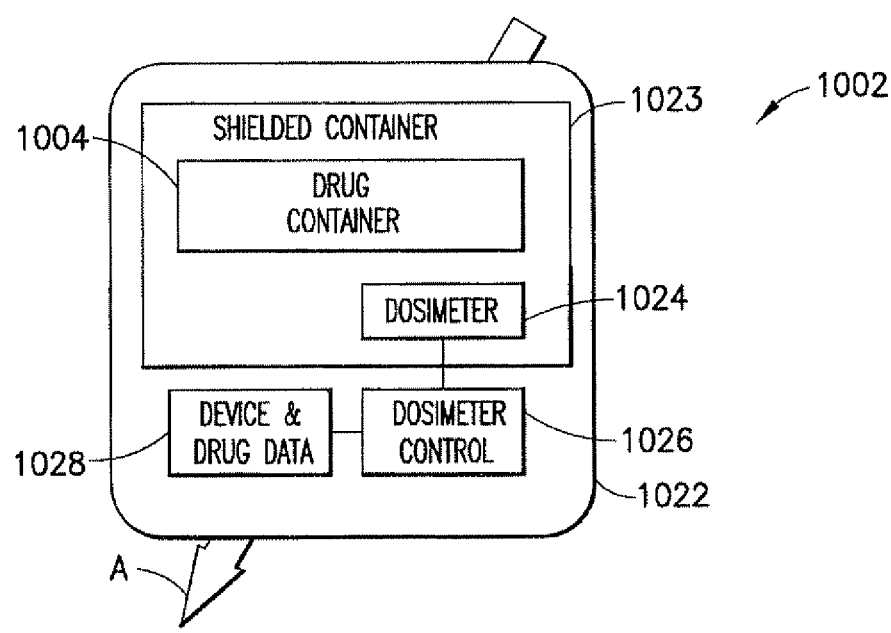
FIG. 14B is a schematic representation of the radiation-shielded transfer device shown in FIG. 14A in transit to another location.
Figure 14C:
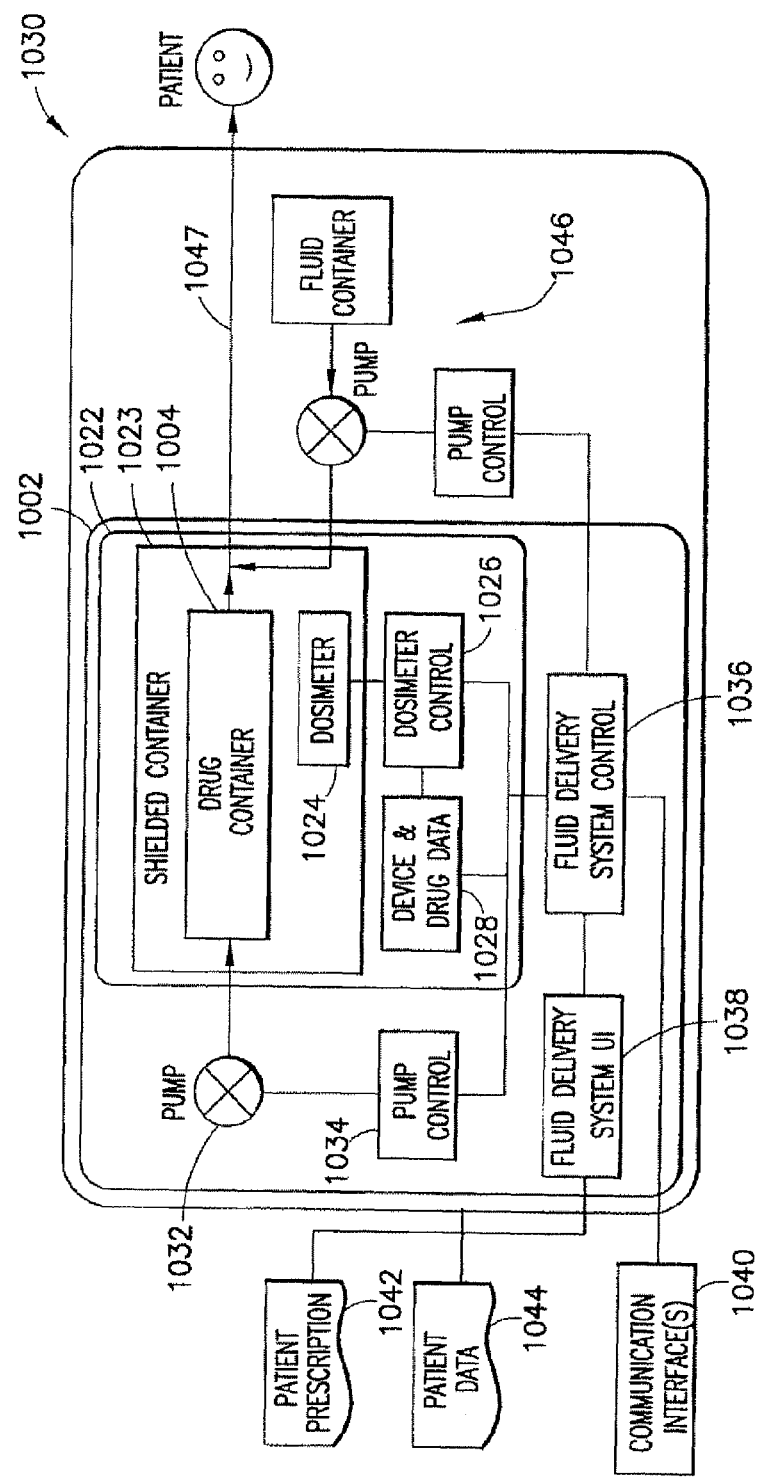
FIG. 14C is a schematic representation showing the radiation-shielded transfer device shown in FIG. 14A associated with a fluid delivery system or component at a receiving location.

As revealed by FIGS. 14A-14C, RS device 1002 according to this embodiment is initially associated with components capable of generating a suitable radioisotope, such as an isotope generator 1006, and a chemistry unit 1008 capable of reducing or transforming the generated radioactive substance into an injectable form. Such components as isotope generator 1006 and chemistry unit 1008 are discussed in detail earlier in this disclosure. As further revealed by FIGS. 14A-14C, RS device 1002 is disposed in or associated with a fill system or module 1010 wherein RP container 1004 is loaded with radiopharmaceutical. Desirably, RS device 1002 engages or interfaces with fill system or module 1010 via mechanical interconnection. As will be appreciated from the foregoing, RS device 1002, as a modular component, is intended to detachably mate with fill system 1010 which itself is likewise a modular component. Fill system 1010 includes components which permit the direct transfer of "injectable" radiopharmaceutical agent from chemistry unit 1008 to RP container 1004, namely, a pump device 1012. Pump device 1012 is controlled by a pump control 1014 which is interfaced with a fill system control 1016. Fill system control 1016 generally operates as a master control for subservient pump control 1014 and a fill system user interface 1018 is used to program and input data to fill system control 1016 for operation of pump device 1012 as well as for other components of RS device 1002 as described herein. As shown in FIG. 14A, both isotope generator 1006 and chemistry unit 1008 may be interfaced with fill system control 1016 via a communications interface 1020 and, therefore, operation of these two units may be effected by fill system control 1016 via communications interface 1020.

Generally, RP container 1004 is a syringe used to hold FDG as an example but may also be a vial, bottle, or similar container. In the form illustrated in FIGS. 14-16, a single RP container 1004 is contained within RS device 1002 but this is merely exemplary for explaining aspects of the invention and RS device 1002 may be configured to contain multiple RP containers 1004. RS device 1002 includes an outer housing 1022 and an internal shielded container or housing 1023 wherein RP container 1004 is physically contained. A dosimeter 1024 is further positioned within internal shielded housing 1023 in operational proximity to RP container 1004 and desirably provides continuous, periodic, or as requested real-time measurement of a radiation dose from RP container 1004. It is contemplated that dosimeter 1024 may be a disposable, single use, or few use item, for example, an inexpensive solid state device made of semi-conducting materials (i.e., silicon, germanium) capable of converting gamma photons emitted by radioactive substances into a real-time electrical current in a very predictable manner. Alternatively, dosimeter 1024 may be reusable and be protected from contamination by a disposable member, sleeve, or shield. Dosimeter 1024 is connected to a dosimeter control 1026 which again is interfaced for control purposes with fill system control 1016. A further aspect of RS device 1002 is a device and drug data recording device 1028 which permits the recording of pertinent data concerning the radiopharmaceutical in RP container 1004, such as the date and time of manufacture and initial radioactivity level, dosimeter calibration curve, container volume, type of fluid, etc. This component may also include identifying indicia (serial number) or other data in electronic or physical form regarding RS device 1002. Moreover, this component interfaces directly with dosimeter control 1026 so that continuous dosimeter readings are recorded and which may be displayed, for example, on fill system user interface 1018 for inspection by attending personnel such as the radio-pharmacist charged with filling RP container 1004 with a desired radiopharmaceutical agent. A monitor which can alert or alarm may be associated with or part of dosimeter control 1026 to alert the operator if there is any change from the steady half-life decay that could indicate a leakage of liquid or a failure of some other system component.

As FIG. 14A demonstrates, generation, dosage preparation, and transfer of injectable radiopharmaceutical agent to RS device 1002 may be accomplished with minimal (or no) physical contact between a radioactive fluid and production personnel, typically a radio-pharmacist. The radiopharmaceutical is delivered straight from production to its container already pre-loaded into a transport device, namely RS device 1002, without physical contact occurring between a human being and the radiopharmaceutical. The provision of pump device 1012 in fill system 1010 and the ability to control this pump device 1012 via suitable electronics allows a correct dosage to be loaded into RP container 1004 and this dosage may be recorded in device and drug data recording device 1028. Dosimetry data is also continuously available at the fill system user interface 1018 on demand. Essentially, it is conceivable according to the foregoing disclosure that a dose of radiopharmaceutical is retained within RS device 1002 until it is injected into a patient.

As FIG. 14B illustrates, when a correct dosage of radiopharmaceutical is dispensed or loaded into RP container 1004 and dosimetry confirmed, RS device 1002 may be "unplugged" in total from fill system 1010. As noted previously, additional data regarding the radiopharmaceutical may be recorded on device and drug data recording device 1028, such as date and time of manufacture, initial radioactivity level, expiration time, manufacturer, etc. This component may also include identifying data concerning RS device 1002 itself. FIG. 14B shows with an arrow A, RS device 1002 in transport to a patient treatment facility. At the patient treatment facility, for example, a hospital, RS device 1002 is desirably docked with a fluid delivery system or installation 1030, as shown in FIG. 14C. Fluid delivery system 1030 includes a primary fluid delivery device in the form of a pump device 1032 adapted to be placed in fluid communication with RP container 1004 when RS device 1002 is docked physically with fluid delivery system 1030. As with fill system 1010, pump device 1032 may be controlled by a pump control 1034. Pump control 1034 is interfaced for control purposes with a fluid delivery system control 1036 in a similar manner to the way pump control 1014 is interfaced with fill system control 1016 discussed previously. Fluid delivery system control 1036 generally operates as a master control for pump control 1034 and a fluid delivery system user interface 1038 is used to program and input data to fluid delivery system control 1036 for operation of pump device 1032.

As further shown in FIG. 14C, other components may be interfaced with fluid delivery system control 1036 including a communications interface 1040 whereby, for example, communications connection may be made to an HIS (Hospital Information System). This allows data about scheduling and the patient to be injected with radiopharmaceutical agent to be brought into the integrated fluid delivery system control 1036 to inform the operator of the procedure and patient conditions or data. The communications connection or interface 1040 further enables the procedure results and notes to be subsequently communicated to physicians, patient records, and other appropriate systems. As shown separately in FIG. 14C, specific data or control inputs may be provided concerning the patient to be injected, including patient data 1042 and the prescribed dosage or patient prescription 1044, which is provided to fluid delivery system user interface 1038 or, potentially, fluid delivery system control 1036. Alternatively, patient specific data and prescribed dosage data may be provided via an HIS connection provided by communications interface 1040. In any of the foregoing alternatives, the fluid delivery system operator has access to patient data and prescribed dosage via fluid delivery system control 1036 and fluid delivery system user interface 1038.

FIG. 14C further shows that, with RS device 1002 docked with fluid delivery system 1030, fluid delivery system control 1036 is operatively associated with device and drug data recorder 1028 and dosimeter control 1026 and may interrogate these components for any of the data items identified previously but, at this stage, dosimetry information regarding the radiopharmaceutical within RP container 1004 is likely very important. This designated importance is because the fluid delivery system operator will likely be concerned with confirming the dosimetry of the radiopharmaceutical so that this data may be compared to that inputted from patient data input 1042, patient prescription input 1044, or both. Other data may also be of value such as the date and time the RP container 1004 was filled with radiopharmaceutical, its initial radioactivity, initial volume, etc. if, for example, a specific ratioed hot/cold mix was to be injected. Fluid delivery system 1030 furthermore desirably at least includes a secondary fluid delivery system 1046 typically for the delivery of saline following or preceding the injection of radiopharmaceutical to patient P. As saline delivery is well-known in the medical field, it is sufficient to note for this disclosure that saline delivery may be automated or controlled via fluid delivery system control 1036. Additional fluids, pumps, and pump controls may be employed as well to deliver additional fluids that are needed for the various procedures for which the device will be used. FIG. 15 is a schematic representation of RS device 1002 pursuant to the foregoing and showing how RS device 1002 may dock with fluid delivery system 1030 which includes a schematic representation of a patient fluid path 1047 leading to a patient. It will be apparent that RS device 1002 may also be "filled" using the features of system 200 described previously, wherein RS device 1002 may be filled with a desired radiopharmaceutical dose while "docked" physically in the patient administration module 260 (which may also operate as a "fill station") of system 200 as described previously. Optionally, an RS device 1002 may be mated with the patient injection module 260 of system 200.

FIG. 16 shows another embodiment of system 1000' which is similar to that shown in FIGS. 14A-14C but with several modifications. In system 1000', isotope generator 1006' and chemistry unit 1008' are similar in configuration to that described previously. In system 1000', however, fill system 1010' comprises a separate pump device 1012' that is controlled by pump control 1014' and is used to directly fill RP container 1004'. RP container 1004' is then inserted into separate, stand-alone dosimeter 1024' which has an associated dosimeter control 1026'. In system 1000', fill station control 1016' is eliminated or segmented from that disclosed hereinabove in that pump control 1014' and dosimeter control 1026' are distinct or separate control devices that respectively operate pump device 1012' and dosimeter 1026'. Moreover, fill system user interface 1018 described previously is also eliminated or segmented in favor a two distinct user separate user interfaces 1018a', 1018b' respectively associated with pump control 1014' and dosimeter control 1026' for entering data for operation of these devices. Once a dosage reading is taken with dosimeter 1026', RP container 1004' is inserted into shielded housing 1023' of RS device 1002' and dosimetry information is communicated to drug data recording device 1028'. RS device 1002' may then be transported to fluid delivery system 1030' as represented by arrow A' in FIG. 16.

At fluid delivery system 1030', RP container 1004' is removed from shielded housing 1023' of RS device 1002' and inserted into a dosimeter 1024' similar to that present in fill station 1010' and now forming part of fluid delivery system 1030'. A dosimetry reading is taken and this may be compared to the readings stored on drug data recording device 1028' of RS device 1002' which is interfaced with dosimeter control 1026' via dosimeter user interface 1018b' at fluid delivery system 1030'. Dosimeter control 1026' may conduct a dosimetry comparison to ensure that the delivery radiopharmaceutical agent is of proper strength and has the expected radioactive decay level for the time elapsed since RP container 1004' at fill station 1010'. Patient data input 1042' and desirably patient prescription input may also be linked or provided as an input to dosimeter user interface 1018b' in the manner described previously in connection with system 1000 (i.e., from a hospital information system and the like). RP container 1004' may then be associated with delivery pump device 1032' of fluid delivery system 1030'. In a similar manner to fill station 1010', dosimeter 1024' comprises an associated dosimeter control 1026' and dedicated user interface 1018b' and pump device 1032' comprises an associated pump control 1032' and dedicated user interface 1018a' so that dosimeter 1026' and pump device 1032' may be separately controlled in fluid delivery system 1030'. A secondary fluid delivery system 1046' may also form part of fluid delivery system 1030' in the manner described previously, with pump device 1032' and secondary fluid delivery system 1046' providing radiopharmaceutical agent and another fluid, typically saline, to patient fluid path 1047' either sequentially or simultaneously. It will be apparent with respect to both systems 1000, 1000' that the disclosed control devices and user interface devices may be provided in close proximity to the device which is operated by the control device and associated user interface or such control devices and associated user interfaces may be remote from the operated devices and linked by wires or wirelessly to the operated devices. Hand-held control devices with associated user interface elements are also within the scope of this disclosure.

Figure 17:
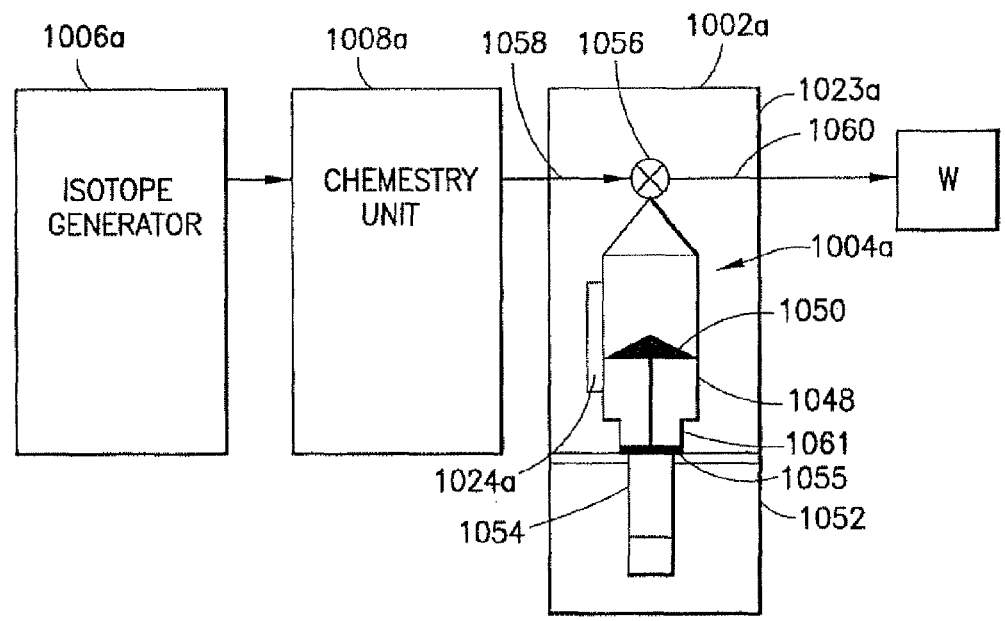
FIG. 17 is a schematic representation of another embodiment of the radiation-shielded transfer device of shown in FIGS. 14A-14C.
Figure 18:
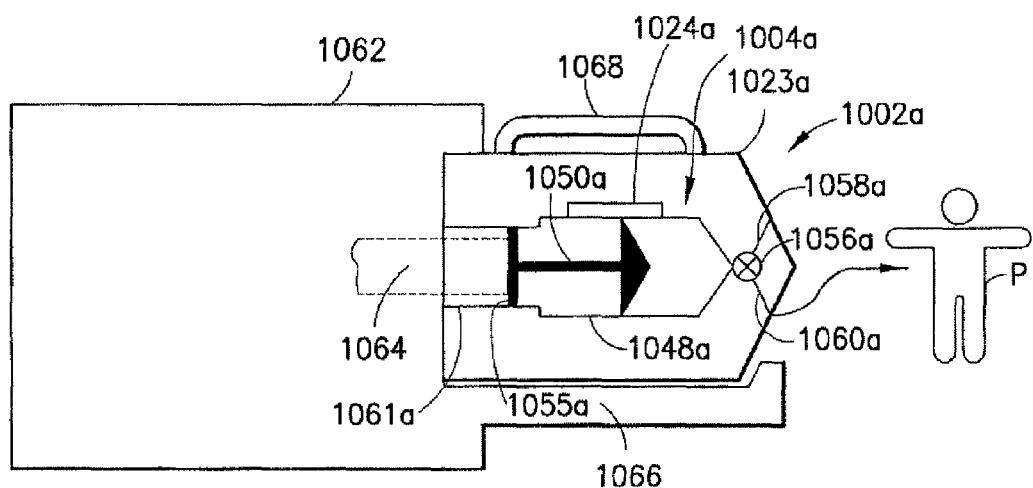
FIG. 18 is a schematic representation showing an embodiment of the radiation-shielded transfer device adapted to interface with a controlled power injector.

Another embodiment of RS device 1002a shown schematically associated with a chemistry unit 1008a and isotope generator 1006*a* described herein above is shown in FIG. 17. In this embodiment, RP container 1004*a* is shown disposed within RS device 1002*a* and shielded by shielded container or housing 1023*a* in a similar manner to the foregoing. Dosimeter 1024*a* is further disposed within in shielded container 1023*a*, which forms the shielding transport structure of RS device 1002*a* in this embodiment. Dosimeter 1024*a* is located in suitable proximity to the body of RP container 1004*a*, in this case a syringe 1048 comprising a movable plunger 1050 and disposed in an internal chamber or cavity defined within RS device 1002*a*. Syringe 1048 may be filled within RS device 1002*a* in the manner described previously, for example, via a pump device associated with chemistry unit 1008 or disposed between chemistry unit 1008 and RS device 1002*a* or by movement of plunger 1050 as described herein. As in the foregoing embodiments, it is desirable that dosimeter 1024*a* housed in shielded housing 1023*a* performs real-time measurement of radiation dose from the syringe 1048 with data displayed, for example, on a user interface associated with the exterior of shielded housing 1023*a*, as depicted generally in FIG. 15 discussed previously. It is possible to use an inexpensive dosimeter, perhaps even a disposable dosimeter, because the energy of gamma rays from a positron-emitting material, such as FDG, is always 511 KeV and inexpensive solid state devices for this purpose may be used for any of the dosimeter devices identified in this disclosure if desired.

As further shown in FIG. 17, RS device 1002*a* is configured so that it can optionally mate with a reusable drive mechanism 1052. Drive mechanism 1052 is generally adapted to engage or interface with syringe plunger 1050 via a piston actuator 1054 to effect movement of syringe plunger 1050 in syringe 1048, for example, to fill and dispense fluid into/from syringe 1048. Syringe plunger 1050 may comprise a rear disc seal 1055 with may be radiation shielded to prevent a rear "shine" of radioactivity from escaping RS device 1002*a* and shielded housing 1023*a* in particular. For example, the inlet to syringe 1048 may be connected to the output of chemistry unit 1008*a* via a control valve 1056. As described previously, chemistry unit 1008*a* is typically provided as part of radiopharmaceutical system 1000. Control valve 1052, which may be a remotely controlled valve, may be used to respectively open or close either or both of an inlet port 1058 and an outlet port 1060 in the body of RS device 1002*a* to place syringe 1048 in fluid communication with chemistry unit 1008 and, for example, a waste dump W. Drive mechanism 1052 is adapted to engage or cooperate with the body of RS device 1002*a* and shielded housing 1023*a* thereof so that piston actuator 1054 engages or interfaces with syringe plunger 1050 to operate and effect movement of the same. However, as shown, drive mechanism 1052 may generally be considered to be part of RS device 1002 and just a separable component therefrom. Accordingly, drive mechanism 1052 may readily separate from the body of RS device 1002*a* so that it may be used on multiple different RS devices 1002*a*.

In operation, when it is desired to fill syringe 1048 with radiopharmaceutical agent, a motor coupled or linked to piston actuator 1054 may be operated to withdraw syringe plunger 1050 in syringe 1048 thereby drawing in fluid through inlet port 1058 leading to control valve 1056, desirably remotely operated to an open position. When syringe 1048 is filled with a selected dose of agent, control valve 1056 is operated to close the fluid connection with chemistry unit 1008*a*. If an incorrect amount of fluid is contained within syringe 1048, control valve 1056 may be operated so that the inlet to syringe 1048 is in fluid communication with waste dump W, typically a shielded waster container well-known in nuclear medicine field, to allow excess radiopharmaceutical agent to be dispensed from syringe 1048 via forward actuation of piston actuator 1054 to eject a selected amount of excess radiopharmaceutical agent into waste dump W. Optionally, several RS devices 1002*a* may be connected in series so that they can be individually filled with individual doses from the chemistry unit. They can optionally be provided as a preconnected set of sterile units, similar to that of U.S. Pat. No. 5,569,181, incorporated herein by reference, to improve the sterility of the filling. After filling, the units are separated and capped. Once a correct amount of radiopharmaceutical agent is present in syringe 1048, RS device 1002*a* may be transported in total to a patient treatment site. At the patient treatment site, when it is desired to deliver the dose of radiopharmaceutical agent to a patient, outlet port 1060 is intravenously connected with the patient via a suitable sterile path. At this point, drive mechanism 1052 may be actuated in a controlled manner to cause syringe plunger 1050 to move distally or forward in syringe 1048 and inject the radiopharmaceutical agent into the patient. This is accomplished generally in the manner described previously, wherein the motor driving piston actuator 1054 moves the piston actuator 1054 forward to engage syringe plunger 1050 and move the syringe plunger 1050 distally or forward within syringe 1050. The interface between piston actuator 1054 may be any convenient interface whereby the piston actuator 1054 engages syringe plunger 1050 to effect movement thereof. An opening 1061 is provided in shielded container 1023*a* of RS device 1002*a* to allow piston actuator 1054 to physically interface with syringe plunger 1050. As will be apparent, a sterile path is desirably provided between outlet port 1060 and any external connection with the outside environment (i.e., waste dump W or patient). In another variation, it is possible for dosimeter 1024*a* to be a part of reusable drive mechanism 1052. Depending upon the cost of the dosimeter, this may be preferable in some situations.

More typically, however, RS device 1002*a* may be adapted to engage a controlled power injector 1062, such as the MEDRAD, Inc. Stellant DX Injector, or the injector disclosed in United States Patent Application Publication No. 2004/0254533 (Ser. No. 10/326,582), incorporated herein by reference. In this configuration, shown in FIG. 18, drive mechanism 1052 is removed from the body of RS device 1002*a* and the RS device 1002*a* directly associated with, for example mechanically engaged with, power injector 1062. Power injector 1062 includes a piston actuator 1064 which desirable interfaces with syringe plunger 1050 in a similar to piston actuator 1054 discussed previously. Power injector 1062 desirably includes a cradle structure or support 1066 for supporting RS device 1002*a* to the power injector 1062 and, further, may serve as a locking structure for physically locking or docking RS device 1002*a* to injector 1062. A handle or other similar carrying apparatus 1068 may be provided for manipulating and transporting RS device 1002*a*. Handle or carrying apparatus 1068 is typically integral with shielded container 1023*a* of RS device 1002*a* and may be used as part of the structure used to mount and optionally lock RS device 1002*a* to power injector 1062. The use of a controlled power injector may be preferred for the fluid dispensing procedure discussed in connection with FIG. 17 due to the ability to precisely control the fluid delivery from syringe 1048 as is known to those versed in the use of controlled power injectors for fluid delivery procedures. Once the radiopharmaceutical dose is delivered to patient P via actuation of syringe plunger 1050 within syringe 1048 by power injector 1062 or, alternatively by actuation of syringe plunger 1050 by drive mechanism 1052, the entire RS device 1002a is desirably returned to a radiopharmacy for processing. As described herein, prior to returning the used or spent RS device 1002a to a radiopharmacy, the internal components of RS device 1002a may be flushed with saline to ensure substantially complete injection of radiopharmaceutical agent into the patient and, further, to ensure maximum removal of radiopharmaceutical agent. Typically, the returned RS device 1002, 1002a is "shelved" for a calculated period of time to allow any residual or retained radioactive material to decay to a safe level. Disposable components in RS device 1002, 1002a, such as RP container 1004 and dosimeter 1024 in RS device 1002 and syringe 1048 in RS device 1002a, as examples, are removed and disposed of according to regulatory standards. Replacement "disposables" may be loaded into RS devices 1000, 1002a making this device suitable for subsequent refilling and reuse. In this way, there is almost no radiation dose exposure to end-use processing personnel.

Figure 19:
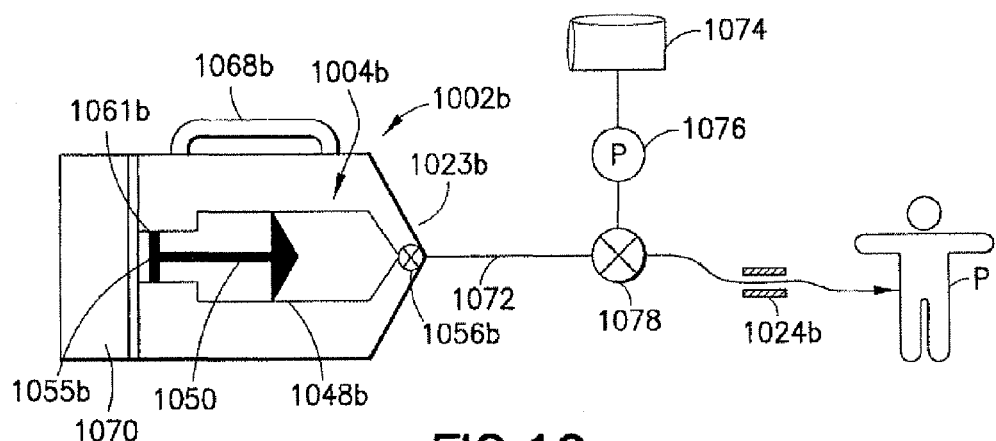
FIG. 19 is a schematic representation showing another embodiment of the radiation-shielded transfer device with an associated "clip-on" dosimeter.

Another embodiment of a self-contained RS device 1002b, which eliminates the need for an internal dose calibrator in shielded container 1023b, is shown in FIG. 19. This embodiment of RS device 1002b is adapted for association with power injector 1062 discussed previously. A removable, shielded end cap 1070 is provided in place of drive mechanism 1052 discussed previously which is removed to allow piston actuator 1064 associated with injector 1062 to engage syringe plunger 1050b of syringe 1048b in the manner described previously. A concentric hole or opening 1061b in the body of RS device 1002b and, more particularly, in shielded housing 1023b, coaxial with syringe plunger 1050b allows engagement of piston actuator 1064 with syringe plunger 1050b. The motorized drive mechanism 1052 discussed previously or even a manually-driven piston to push syringe plunger 1050b may also be utilized if desired. The embodiment of RS device 1002b shown in FIG. 19 also eliminates the need for an internal dosimeter as in RS devices 1002, 1002a discussed previously. In this embodiment, an in-line, "clip on" dosimeter 1024b is used to calibrate radiation dose and is coupled directly to a patient tube 1072 leading to a patient P. Dosimeter 1024b desirably provides radiation dose in real time as fluid flows to patient P. In accordance with the embodiment of FIG. 19, an instantaneous radiation dose to the patient P can preferably be measured and integrated over the duration of an injection, which continues until the prescribed radiation dose has been delivered to the patient P. The clip-on dosimeter 1024b is typically in continuous communication with the control system of injector 1062 or to another control computer. As further shown in FIG. 19, saline 1074 may be associated with patient tube 1072 via a delivery pump 1076, such as a peristaltic pump or syringe pump, and a control valve 1078 to permit flushing of patient tube 1072 once the radiation dose is injected into patient P. If the dosimeter 1024b is in the position shown in FIG. 19, it sees alternatively radioactive drug and saline. Alternatively, the dosimeter 1024b may be positioned between the RS device 1002b and control valve 1078. In this case, it only sees the radioactive drug unless the pump is reversed at some point a saline is pulled into syringe 1048.

Figure 20:
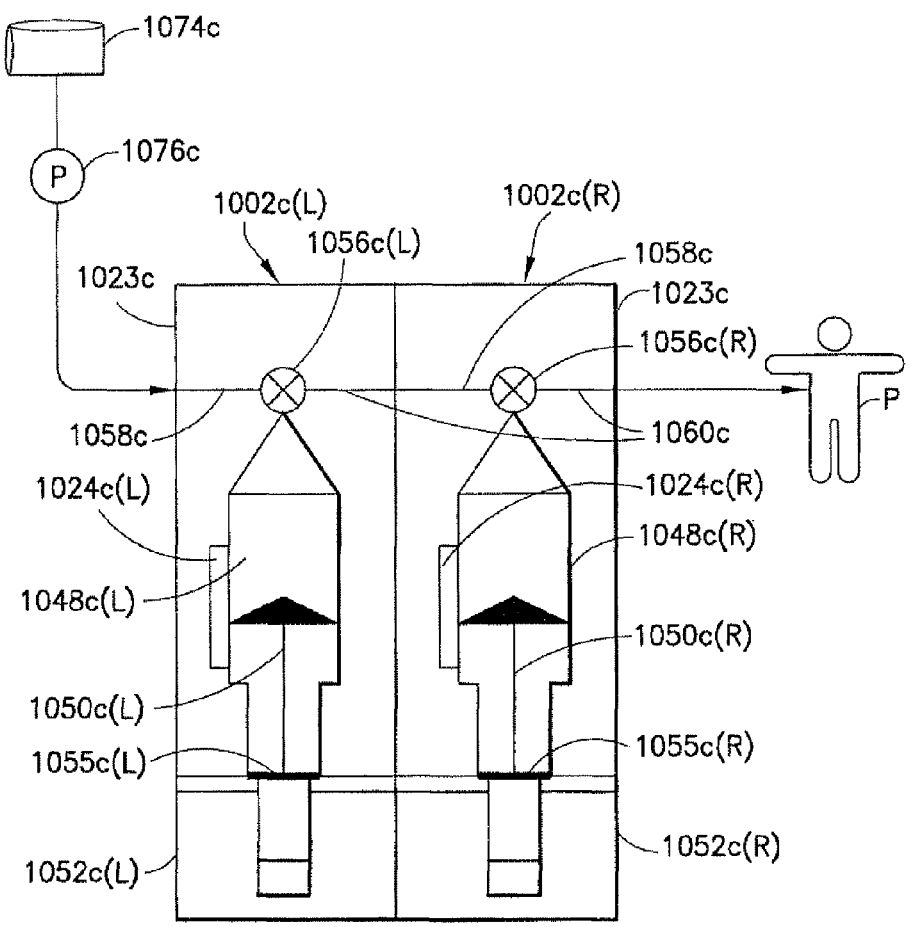
FIGS. 20-21 are schematic representations showing an arrangement wherein radiopharmaceutical agent may be moved between two radiation-shielded transfer devices or two containers disposed within a single such device.
Figure 21:
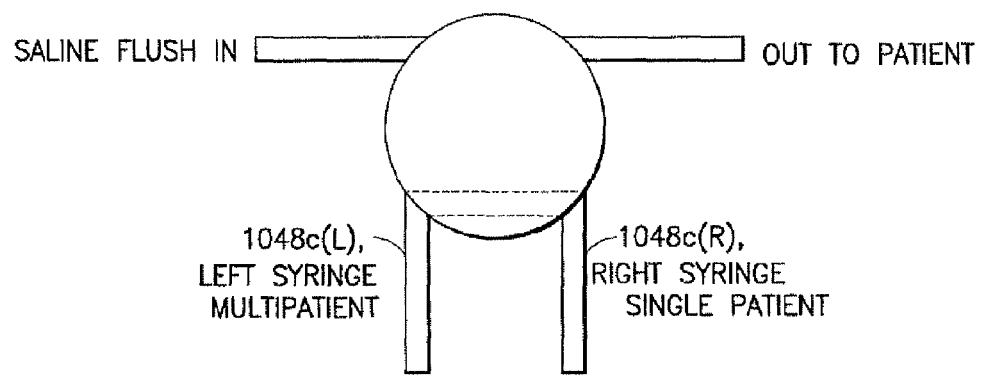

FIGS. 20-21 disclose an arrangement wherein radioactive pharmaceutical agent may be moved between two syringes 1048c(L) and 1048c(R) within, for example, a single RS device 1002c or between two RS devices 1002c in appropriate fluid communication as illustrated. For example, radiopharmaceutical agent may be transferred from a first, transport syringe 1048c(L) within first RS device 1002c(L) into a separate, single dose RP syringe 1048c(R) located in second RS device 1002c(R). Syringes 1048c(L) is desirably larger than syringe 1048c(R) to accommodate multiple doses of radiopharmaceutical while syringe 1048c(R) may be single dose syringe as indicated. Syringes 1048c(L), 1048c(R) are shown of similar size in FIG. 20 only for expedience in explaining features of the invention. The dose increase in one syringe 1048c(R) and the concomitant decrease in the other syringe 1048c(L) can both be measured via on-board dosimeters 1024c(R), 1024c(L) to confirm that the system is leak free and fully functional and that the material is what was expected. Respective drive mechanisms 1052c associated each RS device 1002c, or a power injector as in FIG. 18, may be used to provide the motive forces needed to transfer fluid. Once filled with a single dose of radiopharmaceutical agent, the single dose syringe 1048c(R) may be placed in connection with patient P and actuated to inject the radiopharmaceutical agent in the manner described previously and this is desirably followed by a saline flush.

Radioactive fluid is moved as described in the foregoing from a "larger" syringe 1048c(L), as an example, to a single dose measurement container, syringe 1048c(R), generally for safety purposes. For example, a volume expected to be half of a desired dose of radiopharmaceutical agent is moved from "left" syringe 1048c(L) to "right" syringe 1048c(R). This dose increase on the right and decrease on the left is measured, as indicated previously, to confirm that the system is leak free and fully functional and that the radioactive material concentration is what is expected. Then the remainder of the dose is delivered from the left to the right syringes 1048c(L), 1048c(R) and a second dosimetry measurement is confirmed. Finally, left syringe 1048c(L) is isolated and disconnected from the fluid path. The radiopharmaceutical agent is then delivered from right syringe 1048c(R) followed by a saline flush via saline source 1074c and delivery pump 1076c, again such as a peristaltic pump or syringe pump. Alternatively, the saline flush can be pulled directly into syringe 1048c(R) and then delivered therefrom. This procedure provides multiple checks on the radiation dose measurement and ensures that the whole volume in a multi-patient system can never be delivered to patient P by a single failure. In this embodiment, it is important to account for the radioactive fluid in the volume of the tubing forming inlet and outlet lines or ports 1058c, 1060c and control valves 1056c between the two syringes 1048c(L), 1048c(R). This volume is desirably minimized. Ideally, the control valves 1056c could be made in one plastic piece with almost no volume, utilizes pinch valves, or could be merged into one four input control valve since there is no need to directly connect left syringe 1048c(L) to the line leading to patient P. The valving shown in FIG. 21 is shown with the connection between the left and the right syringes 1048c(L), 1048c(R) for dose extraction and confirmation. Rotating the inner member 90° counterclockwise connects right syringe 1048c(R) to patient P for delivery. Rotating the inner member an additional 90° counterclockwise connects saline flush 1074c, 1076c to patient P for flushing of the fluid path to patient P including the valving and internal ports associated with the RS devices 1002c.

Figure 22A:
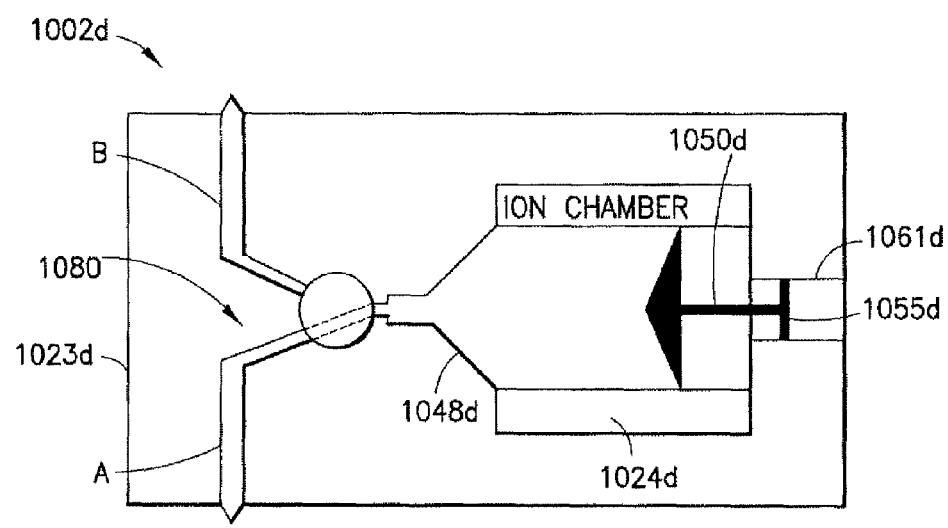
FIGS. 22A-22B are schematic representations of yet another embodiment of the radiation-shielded transfer device.

FIG. 22A shows a no dead space valve arrangement 1080 associated with RS device 1002d according to another embodiment. It is generally preferable that valves be operated automatically in relation to fluid delivery systems as discussed in U.S. Pat. No. 5,840,026 to Uber, III. et al., the disclosure of which was incorporated herein by reference previously. In FIG. 22A, valve arrangement 1080 is shown in a position to fill or dispense syringe 1048d from port A. In the case of fluid delivery, when the delivery is completed, valve arrangement 1080 is rotated approximately 120° so that the fluid path now connects port B to port A. Saline is pumped in port B to drive radioactive fluid from port A and into patient P. The fluid paths from ports A and B are designed so that they are tortuous, with at least no direct line of site from the outlet to the volumes where radioactive fluid is stored. Alternatively, at least two and preferably three normally closed pinch valves could replace the valve arrangement 1080 shown in FIG. 22A. The pinch valves could be spring biased into the off direction and could be activated via electromechanical devices or by mechanical, hydraulic, compressed air, or other forces from outside the shielding housing 1023d. Shield housing 1023d may be designed to open in a clam-shell mode so that tubing can be replaced after use and either flushing or a wait of sufficient time to make it safe for an operator to make such a replacement.

Figure 22B:
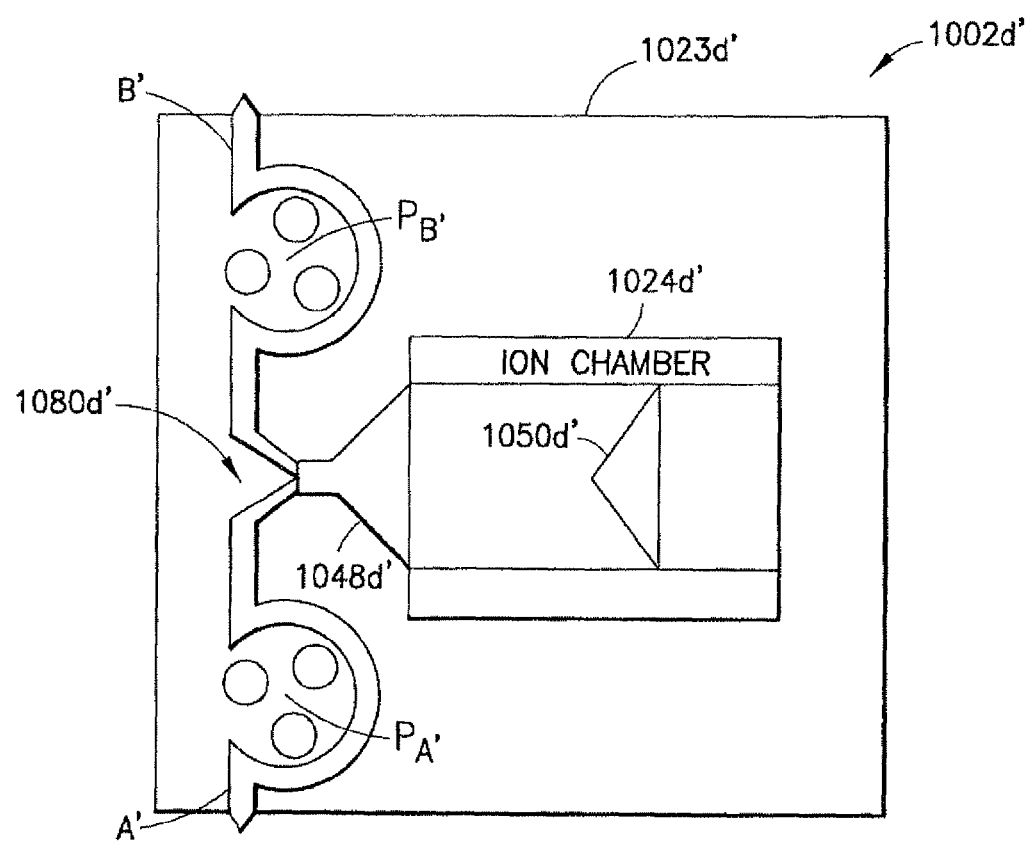

FIG. 22B shows a functionally similar arrangement as in FIG. 22A, with actuated syringe 1048d being replaced by a passive syringe 1048d' (one in which the plunger moves because of pressure changes inside the syringe barrel or body) and two peristaltic pumps $P_A'$ and $P_B'$ replacing the specific valve arrangement 1080d and actuating mechanism for syringe 1050d described hereinabove in connection with FIG. 22A. A benefit of this alternative arrangement is the elimination of the need for a sliding shielding element (1055d) to shield radiation that would otherwise come out through opening 1061d through which syringe plunger 1050d may be engaged as shown in FIG. 22A. Also, peristaltic pumps are simpler in some aspects than syringe pumps. Connection to a source of motive power can be simply by means of a splined shaft. This is simpler than normal syringe attachment strategies. However peristaltic pumps are generally less accurate in an absolute sense than syringe pumps because their flow is a function of the internal diameter of extruded tubing, which is generally not that tightly controllable. However, in this situation, because the activity is being measured before or during delivery, delivery accuracy is generally in terms of activity and not volume. Another advantage of the embodiment of FIG. 22B is that the "bottom" half of claim-shell shielding housing 1023d, 1023d' can serve as a tray, so that if there is any liquid spilled it will be contained and not leak out. The foregoing disclosure and illustration of peristaltic pumps in FIG. 22B is not intended to exclude other suitable types of pumps for the intended application.

As mentioned elsewhere herein with respect to prior art methods of dose calibration, to measure the dose of a radiopharmaceutical with a normal dose calibrator, such as the CRC-15R sold by Capintec, Inc of Ramsey, N.J., the dose of radiopharmaceutical fluid in a container is removed from shielding and lowered into the center of a hollow, generally cylindrically shaped ion chamber. This geometry is used because its sensitivity or calibration is relatively insensitive to the shape and exact positioning of the radiopharmaceutical container. In a number of embodiments described in this disclosure, a dosimeter or radiation detector is explicitly included behind shielding, for example, in FIG. 3, or inside a shielding pig for a radiopharmaceutical, for example in FIGS. 14A-14C and FIGS. 17-18 and 19-22, so that the operator is not required to remove the radiopharmaceutical from shielding and thus be exposed to radiation. This can optionally be incorporated into various other embodiments of this invention as well. If the radiation detector is a hollow, generally cylindrical ion chamber, for example, device 1024d in FIGS. 22A-22B, that surrounds a syringe, vial, or other container, then the radiation measurement will be relatively independent of the position of the radiopharmaceutical fluid in the container. Such an ion chamber may be conventional in the nuclear art as from U.S. Pat. No. 4,804,847 incorporated herein by reference.

In general, a simplified radiation detector, for example, a tubular ion chamber or a linear solid state detector, lying along one side of a fluid volume, the current measured increases supralinearly compared to the fluid volume in the container for a constant radiation dose density (Ci/ml). This result is because at higher volumes more liquid is near more of the ion chamber. In the example embodiments of this disclosure, because internal geometry is known and controlled it is possible to correct for this deviation through calculation and or measurements. This considerably simplifies and reduces dosimetry costs and helps make it feasible to have a dosimeter that is transported with a transport "pig" device such as RS device 1002.

Figure 39A:
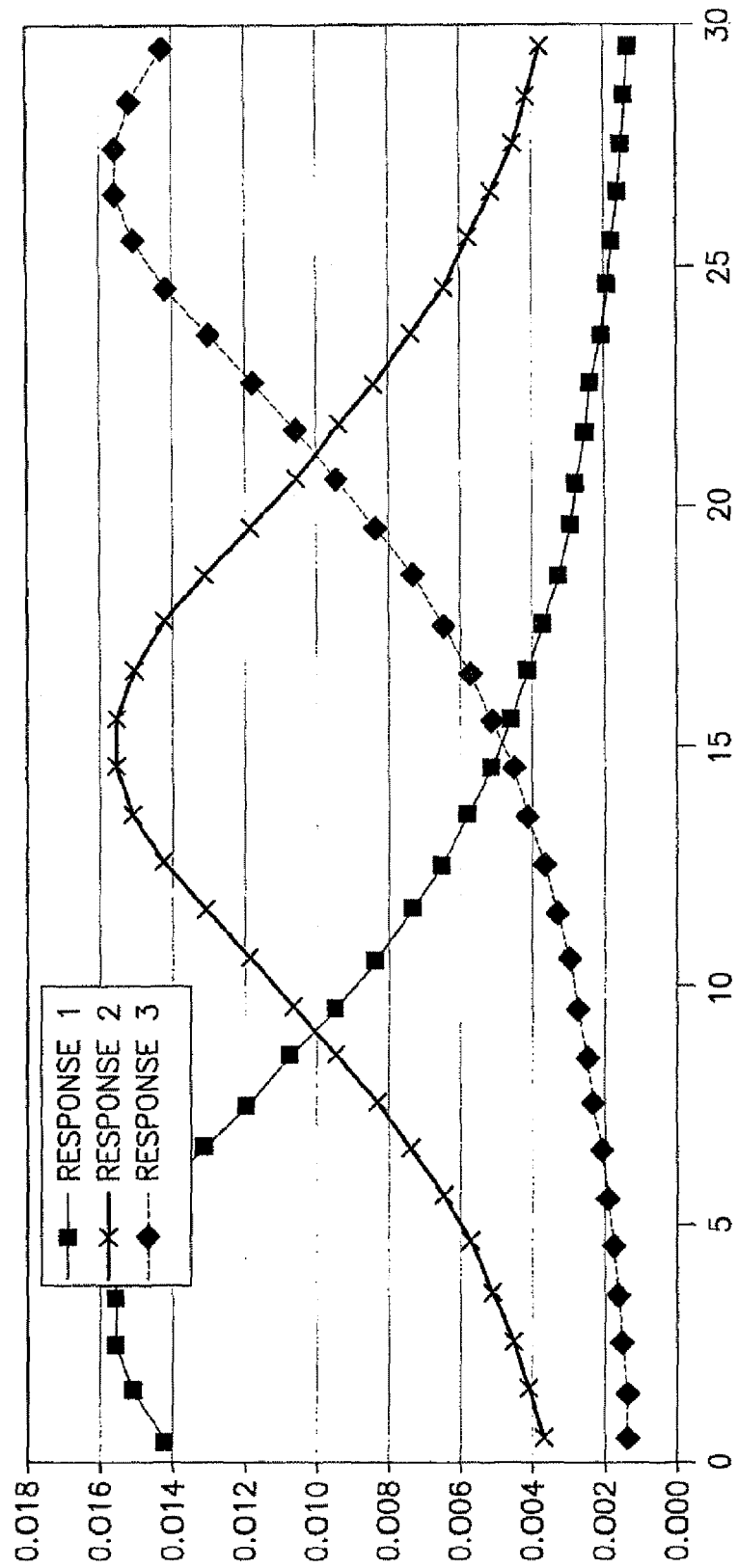
Figure 39B:
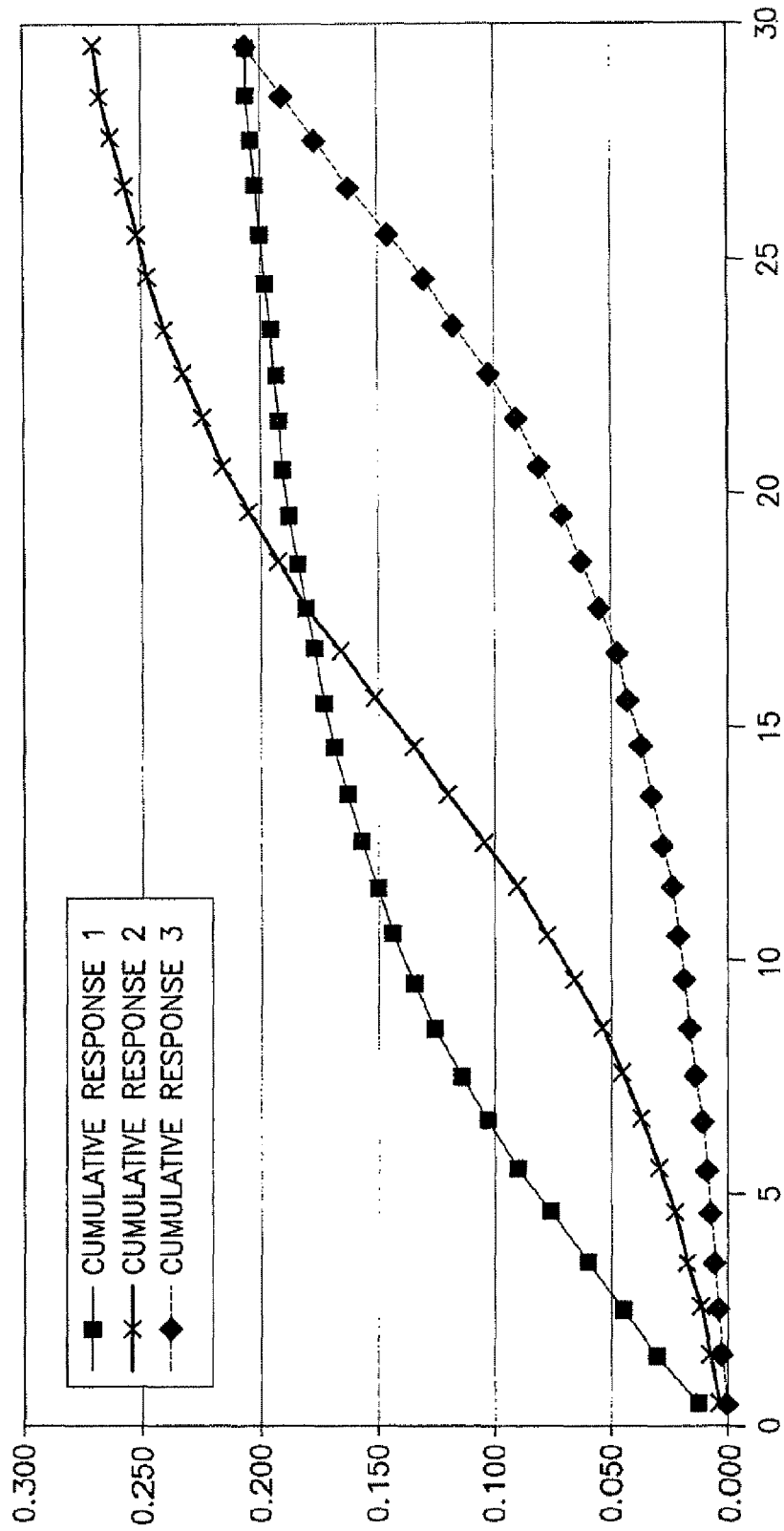

If the radiation detector is a single small area/volume detector, then its response is highly geometry dependent, and the calibration or conversion factor (mCi per current or voltage) is only applicable for that specific geometry. Referring briefly to FIGS. 38 and 39A-39C, these figures show application of basic principles for calculated sensitivity for a small volume dosimeter comprising three detector positions D1, D2, D3, all shown in FIG. 38. In this exemplary embodiment, all three detectors D1, D2, D3 are 8 mm radially from a center axis L of container C which has a length of 30 mm. The first detector D1 is 3 mm down from a top end of container C. The second detector D2 is in the middle, 15 mm from the top end, and the third detector D3 is 3 mm up from the bottom end of container C. FIG. 39A shows the relative detector response (y-axis) for a 1 mm thick volume of radiopharmaceutical at various positions (x-axis) from the top end of container C. The geometric variance of the sensitivity is apparent. In the situation where container C is a syringe, with a luer tip connector at the top end, "position 0" in this example, FIG. 39B shows the detector response as the syringe is filled with increasing volumes of a radiopharmaceutical of constant activity density (mCi/ml). The x-axis in FIG. 39B represents the cumulative fill in milliliters. For clarity of explanation, the effect of the luer connector, neck, and any plunger shape are excluded, and the detectors and syringe diameter are chosen to be small, for example a 0.5 ml or a 1 ml standard syringe. It can be seen that the response of the first detector D1 tends to saturate and become very non-linear. The behavior of the other two detectors D2, D3 is also slow. Thus, if only a single detector was used, in addition to the dosimeter measurement, information about the volume and position of fluid in container C needs to be known and factored into the calculation to determine the total radiation dosage because of the geometric sensitivity of the detector varies so significantly with fill volume. If the responses of detectors D1, D2, D3 are simply added, they effectively become a single long detector and a relatively linear total response is achieved as shown in FIG. 39C. However, just adding the responses wastes some information that could be used to ensure safe operation.

In an optional embodiment wherein dosimeters D1, D2, D3 are present in RS device 1002 of FIGS. 14A-14C and comprise dosimeter 1024, the outputs of two or more dosimeters D1, D2, D3 are individually measured and communicated to the dosimeter control unit 1026 using the features of RS Device 1002 of FIGS. 14A-14C. The dosimeter control unit 1026 can take the two or more dosimeter readings, compare them in some manner, for example, by computing the ratios of each pair of dosimeter readings, and optionally compare the ratios with the measurement of the fill volume available from pump controls 1014, 1034 (or from power injector 1062 in the alternative embodiment of RS device 1002a in FIG. 18) to ensure that there are no anomalies, errors, or problems. Two detectors and syringe piston position data provide enough information to determine if there is any error or bubbles or such. Three detectors and syringe piston position data provide enough information to detect any error or bubbles and estimate the source of the discrepancy. The foregoing application may also be extended to integrated systems 100, 100b described in connection with FIGS. 2A-2B. Problems that can be detected in this way are bubbles in the radiopharmaceutical fluid, spills, or leaks outside the radiopharmaceutical container 1004, or an error in any of the dosimeters D1, D2, D3 or the fill volume measurement. If three or more dosimeters D1, D2, D3 are present, this can be done without fill volume information, or a check of the fill volume information can be performed as well. This ability to confirm the lack of these and other problems through the use of a multiplicity of independent dosimeter measurements, optionally in cooperation with fill volume information, is important because typical radiation shielding is generally opaque, thick, and heavy, and direct observation of a radiopharmaceutical container exposes the operator to radiation. Thus, the foregoing problems, particularly small fluid leaks or air bubbles, cannot be easily known from operator observation since human senses do no respond to low doses of ionizing radiation.

Figure 23:
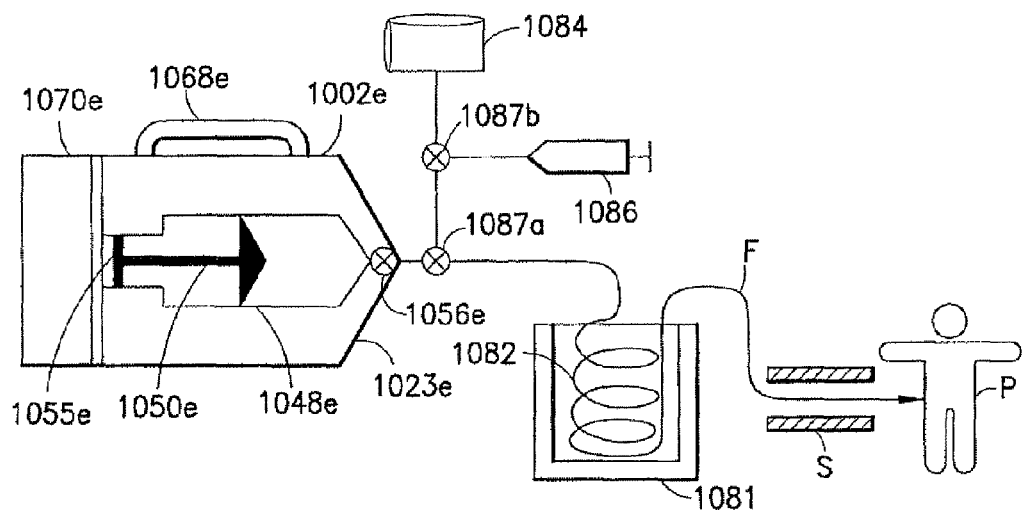
FIG. 23 is a schematic representation showing the radiation-shielded transfer device of FIG. 19 associated with a standard ionization chamber.

In another embodiment utilizing RS device 1002e shown in FIG. 23, a standard ionization chamber 1081 (dose calibrator) holds coiled tubing 1082 which may contain a measured volume of radioactive fluid delivered from unit dose syringe 1048e. Syringe 1048d containing, for example, FDG is held in RS device 1002e and this radioactive fluid is pushed from syringe 1048e via, for example, manual means or controlled power injector 1062 described previously. Saline may be pulled from a bulk container 1084 into a saline syringe 1086 and then injected into coiled tubing 1082 to flush fluid path of any residual radioactive fluid. The tubing forming the fluid path to patient P may be shielded S to reduce radiation exposure to attending personnel. Two control valves 1087a, 1087b, desirably automated valves, may be used to control fluid flow in the fluid path F connecting to patient P.

Figure 24:
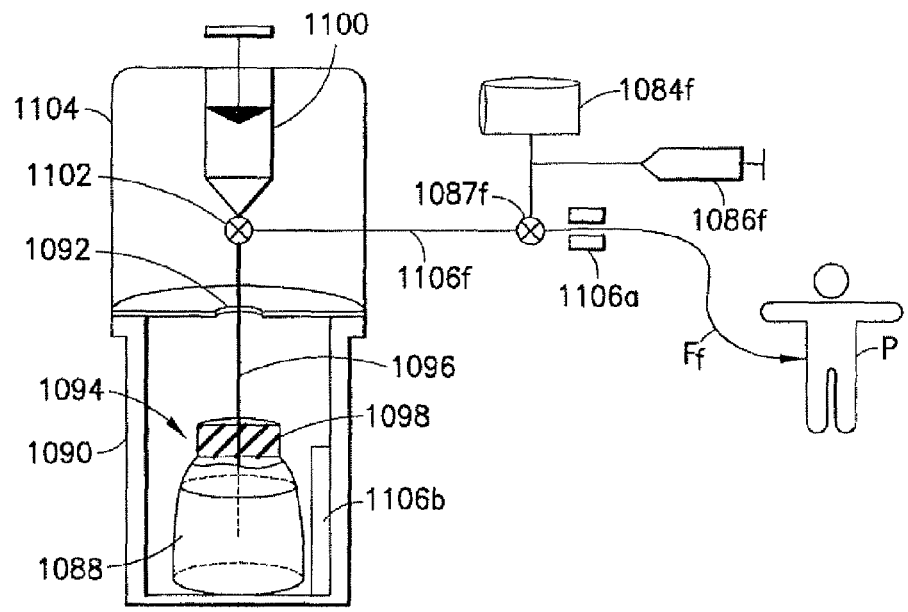
FIG. 24 is a schematic representation showing a multi-dose container delivered in a transport container or pig with a specialized access port and shielded housing.

In another alternative arrangement shown in FIG. 24, multi-dose containers 1088, vials, for example, may be delivered in a shielded transport container or pig 1090 with a specialized access port 1092 at its top end 1094. Access port 1092 allows an elongated needle or pipette 1096 to be guided and inserted down into a rubber septum 1098 sealing radiopharmaceutical container 1088 which reduces radiation exposure to the operator. Radiopharmaceutical agent may be withdrawn into a small syringe 1100 through, for example, a check valve 1102. Syringe 1100 may be contained in a shielded housing 1104 as illustrated. When the syringe plunger of syringe 1100 is depressed, mechanical check valve 1102 directs flow of radiopharmaceutical agent into patient P through fluid path $F_f$ which may be shielded in whole or in part along its length. A clip-on dosimeter 1106a may be associated with fluid path $F_f$ as described previously in this disclosure, or any of the other dosimeter arrangements described previously may be utilized. As further shown in FIG. 24, a second dosimeter 1106b may be disposed within transport pig 1090. Saline flushing may be accomplished using bulk saline container 1084f saline syringe 1086f in the manner described previously in connection with FIG. 23, for example, via a control valve 1087f. Another embodiment has a dosimeter in operable association with vial container 1088, and it is the dose that is removed from this vial container 1088 that is sensed to measure the dose that will be delivered to patient P. This system has also has the benefit that the full dose in the vial container 1088 can never be delivered to a patient P.

Figure 25:
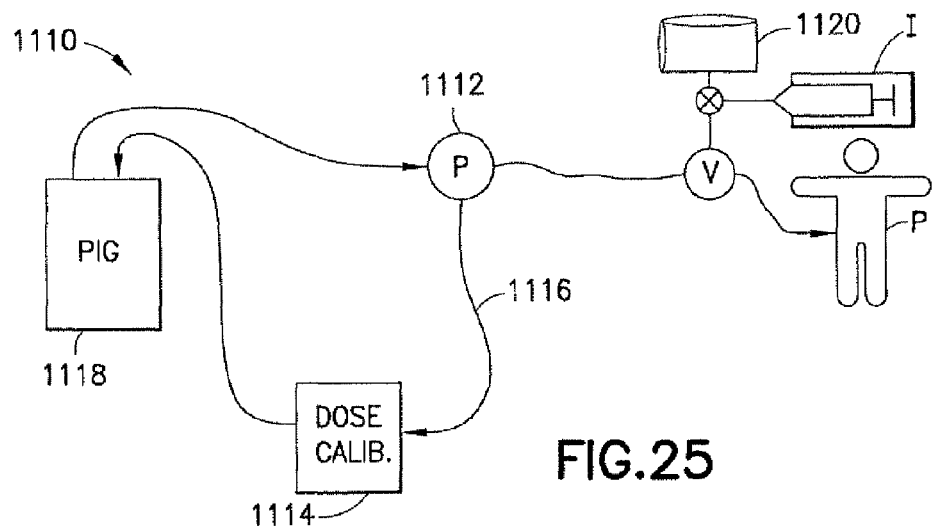
FIG. 25 is a schematic representation of a closed loop system that continuously circulates radiopharmaceutical agent and which may be accessed on demand by a system operator.

Another system for delivery a radiopharmaceutical agent to a patient P is shown in FIG. 25. This system is a closed loop system 1110 that continuously circulates radiopharmaceutical agent via a fluid pumping system or device so that agent may be delivered on demand at a desired volume. An analogous water piping arrangement to closed loop system 1110 is found in a hotel or other large facility hot water system. In these applications, a user will turn on the hot water tap and find hot water immediately instead of having to wait until the water warms the pipes. This saves time and minimizes waste. This type of closed loop pumping system can be adapted for use in delivering critical radiopharmaceuticals that require constant monitoring for strength or radiation activity or solutions that require constant movement to ensure proper mixing. This is especially true for radiopharmaceuticals that have a constantly changing radiation activity level and a short half-life, such as FDG.

Within closed loop system 1110, a pump 1112 continuously circulates the pharmaceutical, such as radiopharmaceutical agent in the form of FDG fluid, through a dose calibrator 1114. A fluid path 1116 connects pump 1112, dose calibrator 1114 and, further, a transport "pig" container 1118 wherein a vial container and the like containing the source of radiopharmaceutical agent is located. In the case of FDG, as an example, this radiopharmaceutical has a short half-life of 110 minutes. Thus, it is valuable to know the radiation activity level of this agent prior to delivery, such that patients receive a proper strength for a useful diagnosis. By constantly circulating this agent through dose calibrator 1114 or other radiation detector, radiation level is continuously monitored and available which provides a known value to a system controller (not shown). This is accomplished because the volume of fluid in operable association with the dose calibrator 1114 is known and, therefore, the total radiation activity may be determined at any time. This "real time" information is the basis for delivering a correct dose to patient P. It is also beneficial because it does not require a secondary testing operation, which wastes time, increase procedure costs, and potentially exposes the operator to unnecessary radiation. Furthermore, patient P may have follow-up procedures which require the exact radiation activity level as previous procedures to ensure radiopharmaceutical uptake is the same and provide a relative disease state over time.

Closed loop system 1110 may be used to supply injection fluid to a controlled power syringe injector I, such as a MEDRAD, Inc. Stellant DX Injector, or the injector disclosed in United States Patent Application Publication No. 2004/0254533 previously incorporated by reference. Prior to initiating an injection the injector operator will program the injector I. One of the input parameters may be the radiation activity level provided by dose calibrator 1114 and, since the injector "knows" the radiation activity level, it can determine the proper injection parameters by using an internally installed algorithm or the operator can program the injection parameters by completing the calculations manually. When the operator initiates an injection, a control valve V diverts the fluid to patient P instead of the continuous circulation loop. Bulk saline 1120 may also be provided as shown to initiate flushing of control valve V and the portion of fluid path 1116 extending to patient P from control valve V.

Several advantages are provided by the foregoing closed loop system 1110. For example, by providing an atmospheric vent and filter (not shown) at the point where transport pig 1118 attaches to the fluid path 1116, it will vent any capture air in the continuous circulation loop. This venting would be accomplished automatically as fluid travels through the fluid path 1116. This is an inexpensive, convenient, and easy method to prevent vascular air injection to patient P. Additionally, connectors at transport pig 1118 provide a convenient method for changing the container housed in transport pig 1118 thereby replenishing the injection volume without having to remove other system components and reinstalling new ones. This is an advantage when the number of scheduled patients exceeds the volume of the container(s) in transport pig 1118. Generally, multiple patients would not be exposed to cross contamination because prevention devices at the patient interface with fluid path 1116, such as check valves and swabable valve connectors, are used. There is yet another advantage of closed loop system 1110 when using multiple transport pig containers 1118 in system 1110. When a transport pig 1118 is changed, the remaining fluid in system 1110 does not need to be evacuated because it will soon reach equilibrium both in radiation activity and temperature as it circulates. The pump 1112 is simply stopped, transport pig 1118 is exchanged, and pump 1112 is restarted to mix the fluid. Minimizing the capacity of system 1110 through small diameter tubing in fluid path 1116 and a small chamber pump for pump 1112 can further enhance this benefit.

Figure 26:
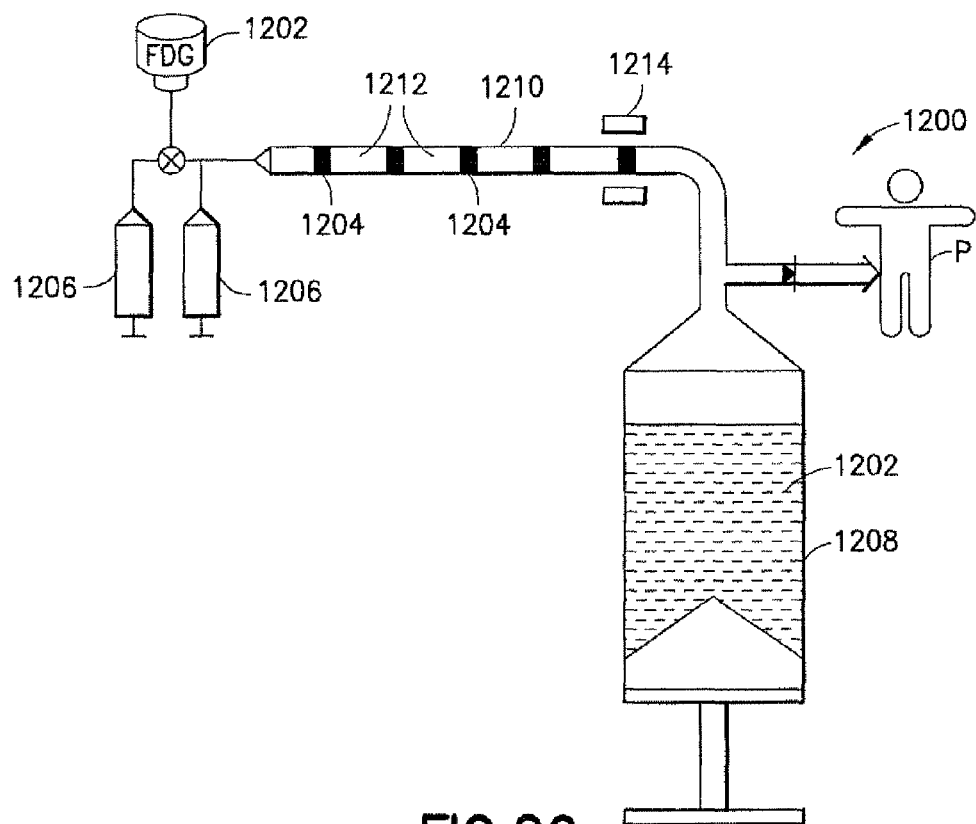
FIG. 26 is a schematic representation of a "slug" counting injector system for metering a calibrated fluid dose of radiopharmaceutical or another agent to a patient.

FIG. 26 shows a system 1200 for metering a calibrated fluid dose of FDG 1202, as an example (or other substance), to a patient P, hereinafter termed an FDG "slug" counting injector system 1200. Injector system 1200 is useful in that it overcomes well-known inaccuracies in conventional syringes due primarily to manufacturing variations in internal diameter and to "dead space" within the syringe. The disclosed arrangement provides a means to accurately control the amount of fluid and, therefore, the radiation dose by dividing the fluid into small, discrete "slugs" 1204 of FDG of precisely uniform volume which can be collected and recombined into a total dose for injection into a patient.

In injector system 1200, a micro-dosing syringe or multiple such syringes 1206 withdraws an FDG fluid volume less than one ml from a large container, such a large diameter syringe 1208, and then delivers it into a length of intermediate tubing 1210. After the fixed amount of FDG slug 1204 is injected into tubing 1210, a slug 1212 of intermediate air or another gas or potentially a viscous liquid is injected into tubing 1210, followed by another fixed amount of FDG slug 1204. Air slugs 1212 could also be replaced by a physical or mechanical spacing element, such as a plastic bead or rod, which prevents successive FDG slugs 1204 from mixing. As the alternating FDG slugs 1204 and air slugs 1212 (or equivalent spacing or separator elements) are introduced into tubing 1210, they are counted by an optical slug counter 1214. Alternating FDG slugs 1204 could be placed in a dose calibrator or an inexpensive dosimeter which could give a reading of radioactivity level per fixed FDG slug 1204. Optical slug counter 1214 would then count the number of fixed FDG slugs 1204 that pass by until reaching the desired total radioactive dose. A clip-on, in-line dosimeter such as dosimeter 1106a discussed previously in connection with FIG. 24 could be used as the dose calibrator in this embodiment.

Once the FDG slugs 1204 and air slugs 1212 (or equivalent separator elements) drop into a vertically-positioned syringe 1206, they would tend to naturally separate therein, for example, with air rising to the top and liquid FDG 1202 located below. This air would be expelled out of syringes 1206 either manually or through an air separator, such as a membrane filter from Celegard®, LLC., a division of Polypore®. Physical or mechanical separator elements would either float above the liquid FDG 1202 or sink below the liquid FDG 1202 depending on their relative density. Physical or mechanical separator elements would then be extracted mechanically. The fixed dose in the dose calibrator would decay naturally over time, and the activity level per fixed FDG slug 1204 would decrease accordingly. This would require more fixed FDG slugs 1204 to be delivered at the end of the day for a desired activity level, (for example, 15 fixed FDG slugs=15 milliCuries at 9:00 am and 30 fixed FDG slugs=15 milliCuries at 11:00 am). Alternatively, one fixed slug could be directed into the dose calibrator or directed past a dosimeter followed by a longer air column to obtain an initial radiation dose reading. Then the alternating FDG slugs 1204 and air slugs 1212 (or equivalent separator elements) could be sent down tubing 1210 and counted by optical slug counter 1214.

As described elsewhere herein, system 200 of FIGS. 3-4 generates, prepares, and delivers radiopharmaceuticals to a patient for an imaging study or therapeutic treatment. In the total or integrated systems 100, 100a of FIGS. 2A-2B, it is preferable that the radiopharmaceuticals be brought near the patient for the delivery such as through the use of a "mobile" system 200. However, there are some instances where it is too difficult to take portable or mobile system 200 to the patient or bring the patient to system 200. One example of such a situation is an in-patient PET or nuclear medicine study where it is advantageous to give the patient an FDG injection in their hospital room so that the patient can continue to be monitored and treated by using normal ward equipment and nursing staff rather than wait in a waiting area or on their bed in the hall near the imaging area where providing appropriate care is more difficult. The patient is only brought from his or her room to the imager after the appropriate time for dose uptake (step 60 described previously) is imaged relatively quickly after arrival, and is expeditiously returned to his or her room for continued care and treatment.

A second situation is for use with a portable gamma camera. While the modular and transportable nature of system 200, typically supported on wheels for portability, assists in its transport this structure may not be easy to move due to the weight of shielding needed to appropriately protect attending medical personnel and the operator. In some situations, it may be more convenient and more efficient to keep this unit in operation in association with its normal imager or integrated system 100 and just take the individual dose to a patient, for example, with a portable gamma camera. One example of a small, portable, hand held gamma camera is the eZ-Scope manufactured by eV Products of Saxonburg, Pa.

A third situation benefiting from the separate creation and delivery of individual doses of radiopharmaceutical agent is during a transition period where the hospital or health care facility may have one or more components of the total or integrated systems of FIGS. 2A-2B, one or more components in system 200 of FIG. 3-4, or one or more of the multi-fluid and multidirectional systems of FIG. 7, and have some non-integrated, often preexisting, equipment as well. Some embodiments are flexible enough to produce radiopharmaceuticals to be used and delivered remotely as well as to a patient in close proximity to other embodiments described in the foregoing. For use in these situations, this disclosure further includes physically separate embodiments of systems, devices, and methods to facilitate accurate and safe delivery of the radiopharmaceuticals to the patient.

Embodiments to facilitate remote delivery of a dose of radiopharmaceutical agent to a patient or multiple doses to multiple patients were described previously in connection with FIGS. 14-25. The foregoing discussion relating to FIGS. 14-16 in particular enables transfer of information as well as the radiopharmaceutical into a fluid delivery system with minimal handling of a radiopharmaceutical by the operator and thus minimal radiation dose to the operator. The remote delivery can still have significant aspects of integration, although it does not need to include physical proximity aspects. For example, the smart transport device or RS device 1002 described previously can, preferably wirelessly in real time (or through a wired communications port) or when docked with a fluid delivery system 1030 or even mobile system 200, communicate information about the patient, dose, and time at which the dose is administered to a central controller such as the integrated system controller 110 in total or integrated system 100 described previously, optionally via a hospital information system (HIS) or other network.

If a treatment facility such as a hospital prefers a less sophisticated solution, system 200 shown in FIGS. 3-4 can deliver a dose to a normal vial or syringe in a typical shielding configuration, for example, a cylindrical syringe shield with a lead glass window. This shielded syringe can then be put into a lead lined syringe carrier, such as available from Pinestar Technology Inc., Greenville Pa. (Model 001-182). A similar shielded syringe carrier is available from Lemer Pax of Carquefou-Nantes in France (Model Ref. SC3).

With the foregoing in mind, this disclosure turns to improvements to radiation shields which may be used in to shield an operator of a syringe when the syringe is used for the simplest delivery known in the nuclear medicine field, namely, a hand-held manual delivery. A typical syringe shield 810 is shown schematically shown in FIG. 27. As an example, syringe shield 810 may be constructed of 0.06 inch (1.5 mm) thick tungsten that will reduce radiation exposure from Tc-99m by 94%. Alternatively, syringe shield 810 may be made of 6 mm thick tungsten for use in PET emitters. Syringe shield 810 is intended to hold a sterile plastic disposable syringe 800. Syringe 800 has a plastic body or barrel 801 with a syringe plunger 802 disposed inside syringe barrel 801 and movable within syringe barrel 801 to pressurize a fluid in the syringe barrel 801 for filling or delivery. Syringe plunger 802 is moved via a piston or piston rod 803 which commonly has a syringe piston button 804 for finger or thumb actuation, or hand applied force. A penetrating needle 805 is provided at a distal end of syringe barrel 801. Syringe shield 810 comprises a cylinder body 811 which may be made of lead or tungsten with a lead glass window 812 for viewing the position of syringe plunger 802 in syringe barrel 801 and volume markings on the side of syringe barrel 801 so that the operator can manually control and confirm the injection of the proper amount of radiopharmaceutical. The window 812 is commonly used when manually filling the syringe 800.

Figure 27:
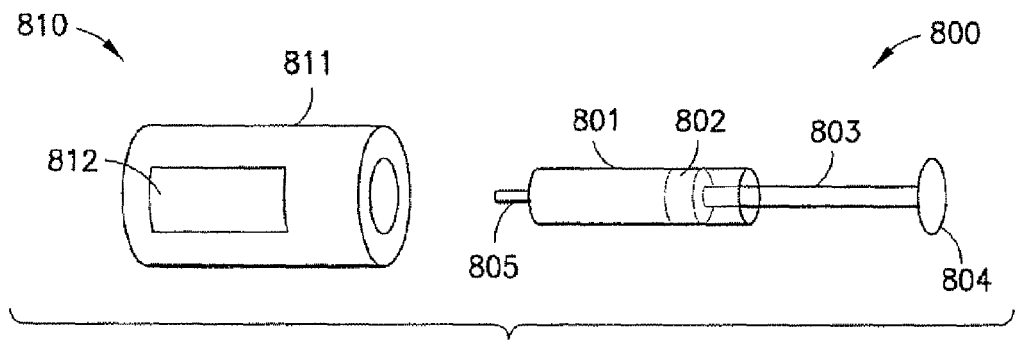
FIG. 27 is a schematic representation of a prior art manual syringe shield.
Figure 28:
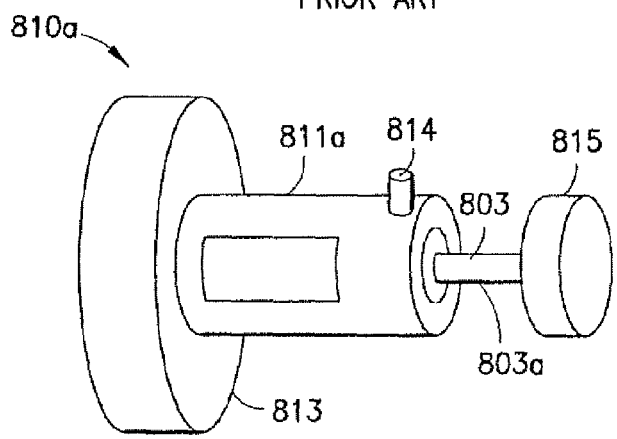
FIG. 28 is a schematic representation of a manual syringe shield according to one embodiment comprising a locking mechanism.

FIG. 28 shows an improved syringe shield 810a with a combination of different features. For example, a cuff or front shield 813 is available on syringe shields from Pinestar and may be incorporated into syringe shield 810a. Syringe shield 810a may also include a locking mechanisms 814 which can be a thumb screw, a spring loaded lever, or other mechanisms that can hold syringe body or barrel 801 (shown in FIG. 27) in shield cylinder body 811. The benefit of locking syringe 800 into syringe shield 810a is that the syringe shield 810a can then be use to turn the syringe barrel 801 to make a connection to a luer fitting as an alternative to a needle for fluid delivery purposes. By grasping syringe shield 810a, the operator receives less radiation dose than if they had to hold an unshielded syringe 800. A shielded button or disk 815 may be placed on syringe piston button 804. Such buttons are available, for example, from Lemer Pax.

Figure 29:
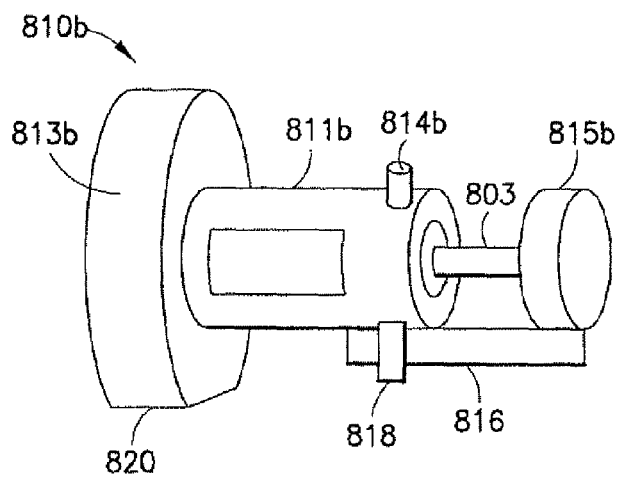
FIG. 29 is a schematic representation of the manual syringe shield of FIG. 28 further comprising an operable support rod.

In a modification of the foregoing syringe shields 810, 810a, as illustrated in FIG. 29, these syringe shields 810, 810a are combined with a support rod 816 so that shield button or disk 815b may be associated with shield cylinder body 811. Support rod 816 moves in a grove or through a sliding bearing 818. It is preferable that there be sufficient friction to help hold support rod 816 in place, as can be created with a rubber pad or spring. A locking mechanism (not shown) could be added in association with the support rod 816 so that once the syringe piston rod 803 is positioned, it cannot be moved either intentionally or inadvertently until the lock is released. By using support rod 816, the various parts of the syringe shield 810b are kept together and the lock or friction mechanism makes it less likely that there will be accidental movement of syringe piston rod 803. There can be one or more flat edges on cuff or front shield 813 to reduce the chance that the syringe in the holder will roll off a flat surface. A single flat edge 820 is shown as an example.

Figure 30:
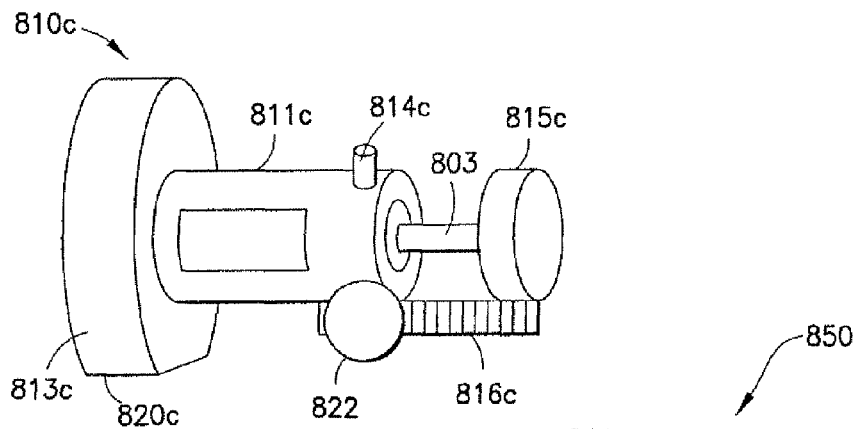
FIG. 30 is a schematic representation of the manual syringe shield of FIG. 29 wherein the support rod is optionally knurled or ribbed and structure is provided to operate the support rod.

A further embodiment of syringe shield 810c is shown in FIG. 30, wherein support rod 816c is knurled or ribbed, and a thumb wheel 822 is provided so that the operator can move the shield button or disk 815c in or out by rotating the thumb wheel 822. This configuration enables one handed operation to fill or deliver from syringe 800. Thumb wheel rack and pinion arrangements can be found on plastic pipetting devices, such as the Glasfirn Safety Pi-Pump 2500, made by Glasfirn of 35396 Giessen-Wieseck, Germany.

Figure 31:
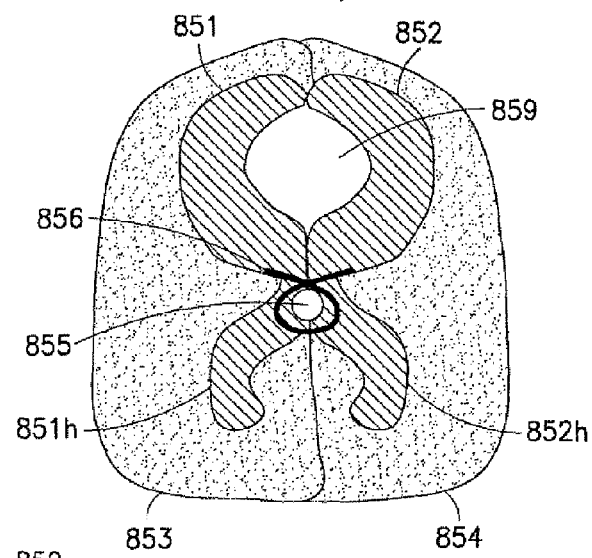
FIGS. 31-32 are schematic representations of a syringe shield system that operates in a clamshell manner.
Figure 32:
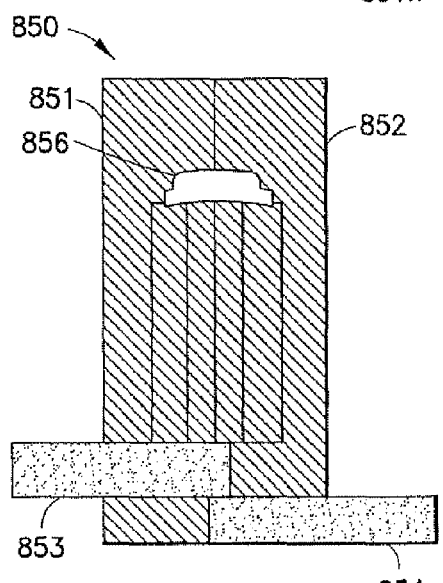

Another embodiment of a syringe shield system 850 is shown schematically in FIGS. 31-32. This syringe shield system 850, in operation, opens like a clamshell to allow a syringe 800 (shown in FIG. 27) to be put placed therein. This opening arrangement can be of tremendous benefit when placing syringes into or removing them from dose calibrators, as the syringe shield itself can act as a pair of shielded tongs to enable the operator to deposit and pick up a syringe from the carrier that is usually used to lower the syringe into the dose calibrator thereby providing significant shielding for their hands.

The components and operation of syringe shield system 850 will now be explained. There are four primary parts to syringe shield system 850. Barrel shield portion 851, 852 shield the barrel 801 of syringe 800 (shown in FIG. 27). There are wings or handles 851h, 852h that are rigidly associated with barrel shield portions 851, 852. These wings or handles 851h, 852h can be the same material, for example, lead, tungsten, or lead loaded acrylic, as barrel shield portions 851, 852 or can be a different material and be bonded or otherwise rigidly associated with the barrel shield portions 851, 852. Lead loaded acrylic has the benefit of the operator being able to see through this material as it is positioned to draw a dose or be placed in the dose calibrator syringe holder. The bottom cuff is also made in two cuff parts 853, 854. Cuff 853 is positionally associated with barrel shield portion 851 and cuff 854 is positionally associated with barrel shield portion 852. A pin 855 serves as a hinge pin to enable barrel shields 851, 852 to separate when the user squeezes on wings or handles 851h, 852h. There is also an optional spring 856 that provides a force to close the barrel shield portions 851, 852 when the operator releases wings or handles 851h, 852h. A central opening 859 is defined between barrel shield portions 851, 852 which accommodates syringe 800.

Figure 33:
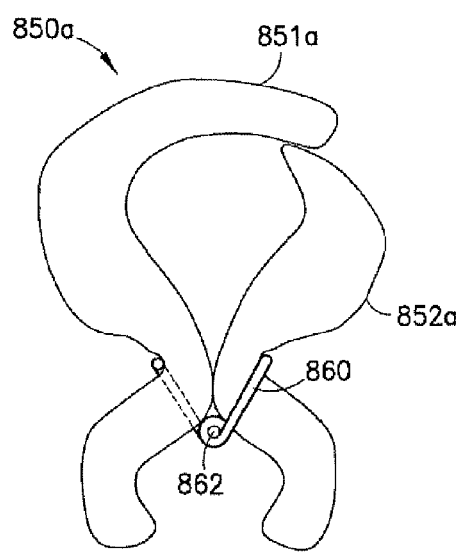
FIGS. 33-34 are schematic representations of an alternative embodiment of the syringe shield system of FIGS. 31-32.
Figure 34:
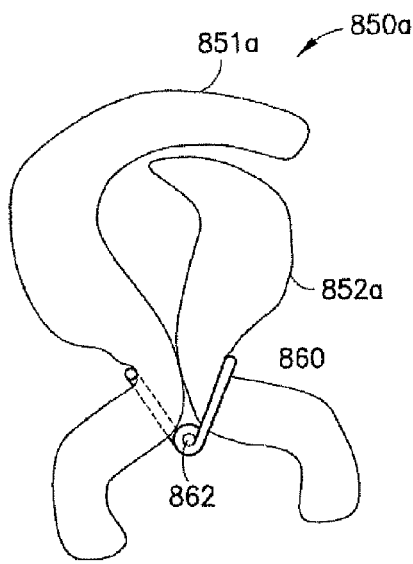

A modification to the clamshell syringe shield system 850a described above is shown in FIGS. 33-34. By making syringe shield system 850a from with two asymmetrical pieces 851a, 852a, it is possible for this device to hold and shield a variety of syringe diameters. These two asymmetrical pieces 851a, 852a are biased in a normally closed mode by a wire spring arrangement 860 similar to that of a wooden clothes pin operating around a central cylindrical member 862. Central cylindrical member 862 provides additional shielding for the radiation path between the two mating ends of asymmetrical pieces 851a, 852a. Bottom cuffs (853, 854), similar to those of the previous embodiment, can be included but are not shown in this embodiment. In typical syringe barrels such as syringes barrels 801 shown in FIG. 27, between one and ten milliliters are commonly used and, if they are of approximately the same length, the diameter ratio that needs to be accommodated is approximately 3.1 to 1. However, if as is discussed elsewhere in this disclosure, the shielded syringe is placed in an electronic servo-controlled feedback injector or pump, small volumes can be accurately delivered from a large diameter syringe; volumes on the order of 1% or better are achievable. In this case, one size syringe 800 (as shown in FIG. 27), for example, 10 ml can be used for all fluid deliveries, therefore, the range of syringe sizes can be greatly reduced. The manually operated syringe shield system embodiments just described can be incorporated into all the embodiments of this disclosure and can optionally incorporate additional features as well. Among the possible additional features are those related to RS device 1002, for example, electronic dosimetry, wireless communications, and data identification devices such as a bar code or label and electronically readable storage devices such as RFID. In addition, with a rack and pinion drive or other drive mechanism, they can be matted with a motorized drive system as shown, for example, in FIG. 37 discussed herein.

Figure 35A:
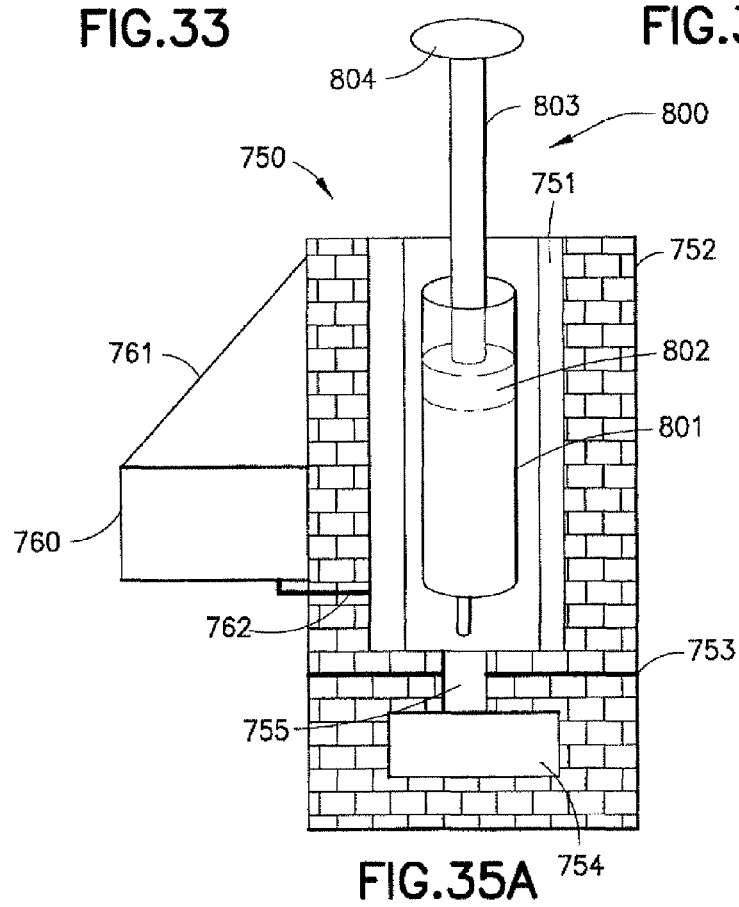
FIG. 35A is a schematic representation of a dose adjuster in accordance with other aspects of the invention set forth herein
Figure 35B:
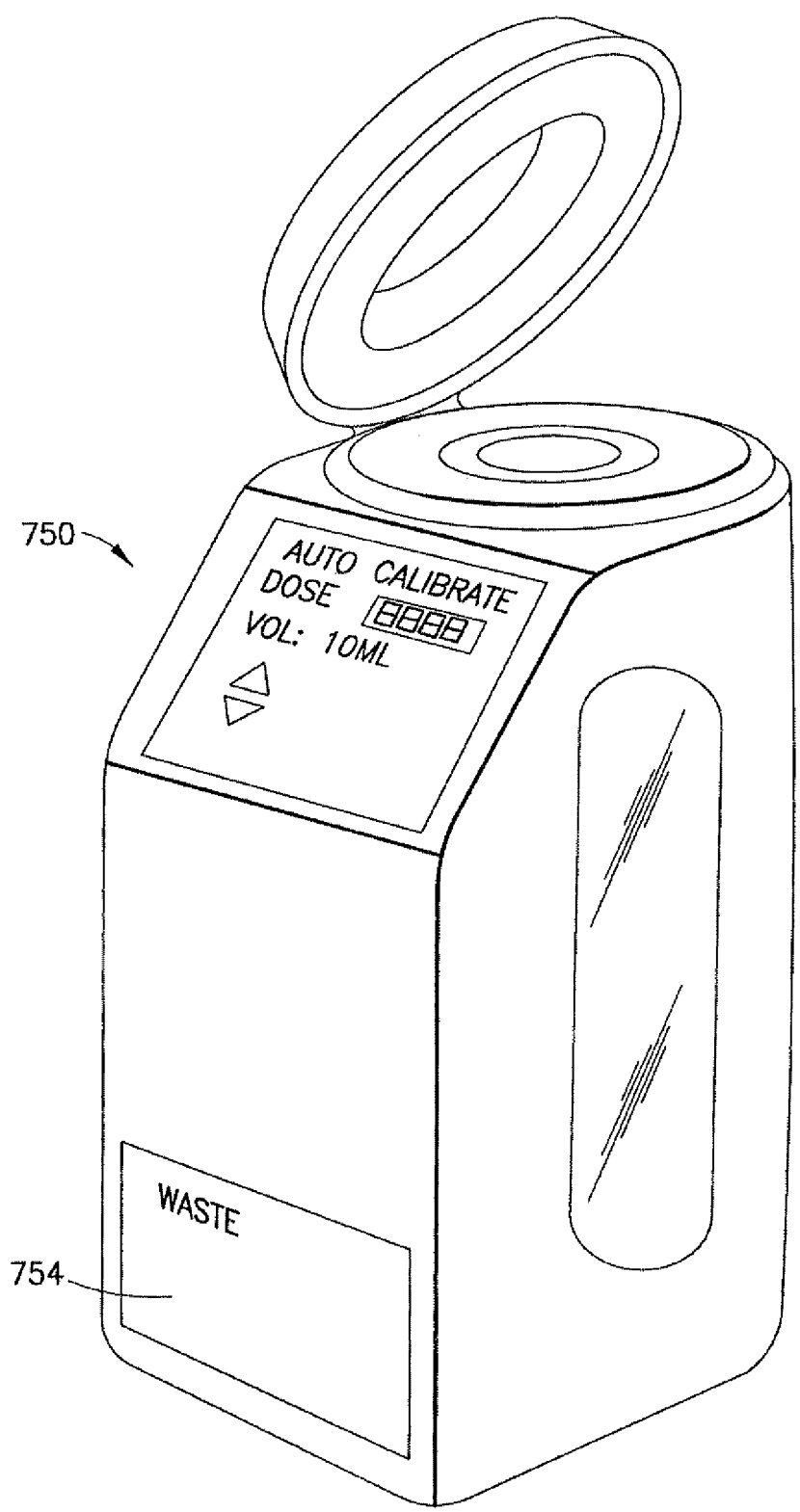
Figure 36A:
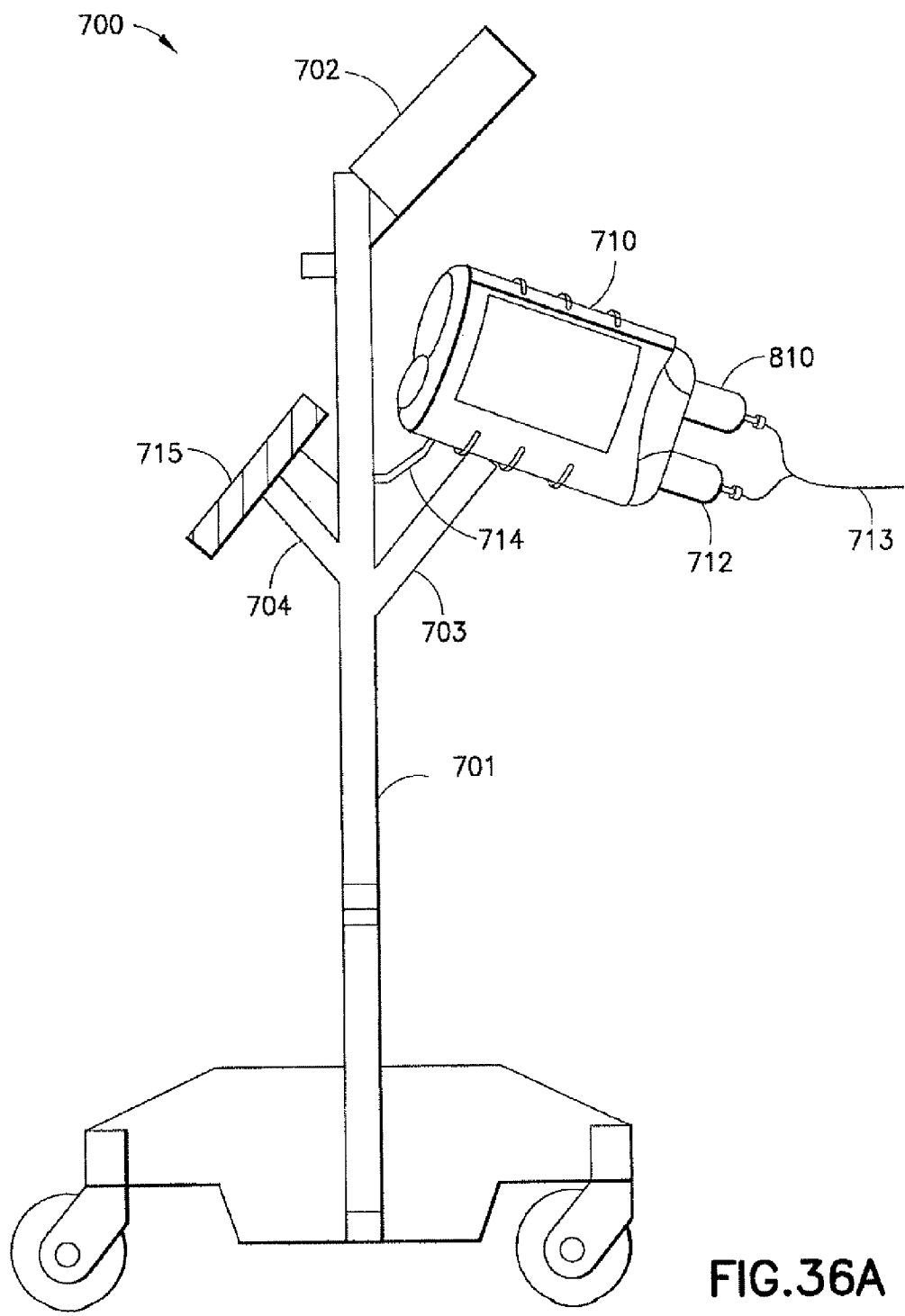
FIG. 36A is a schematic representation of a fluid delivery system utilizing a power injector platform.
Figure 36B:
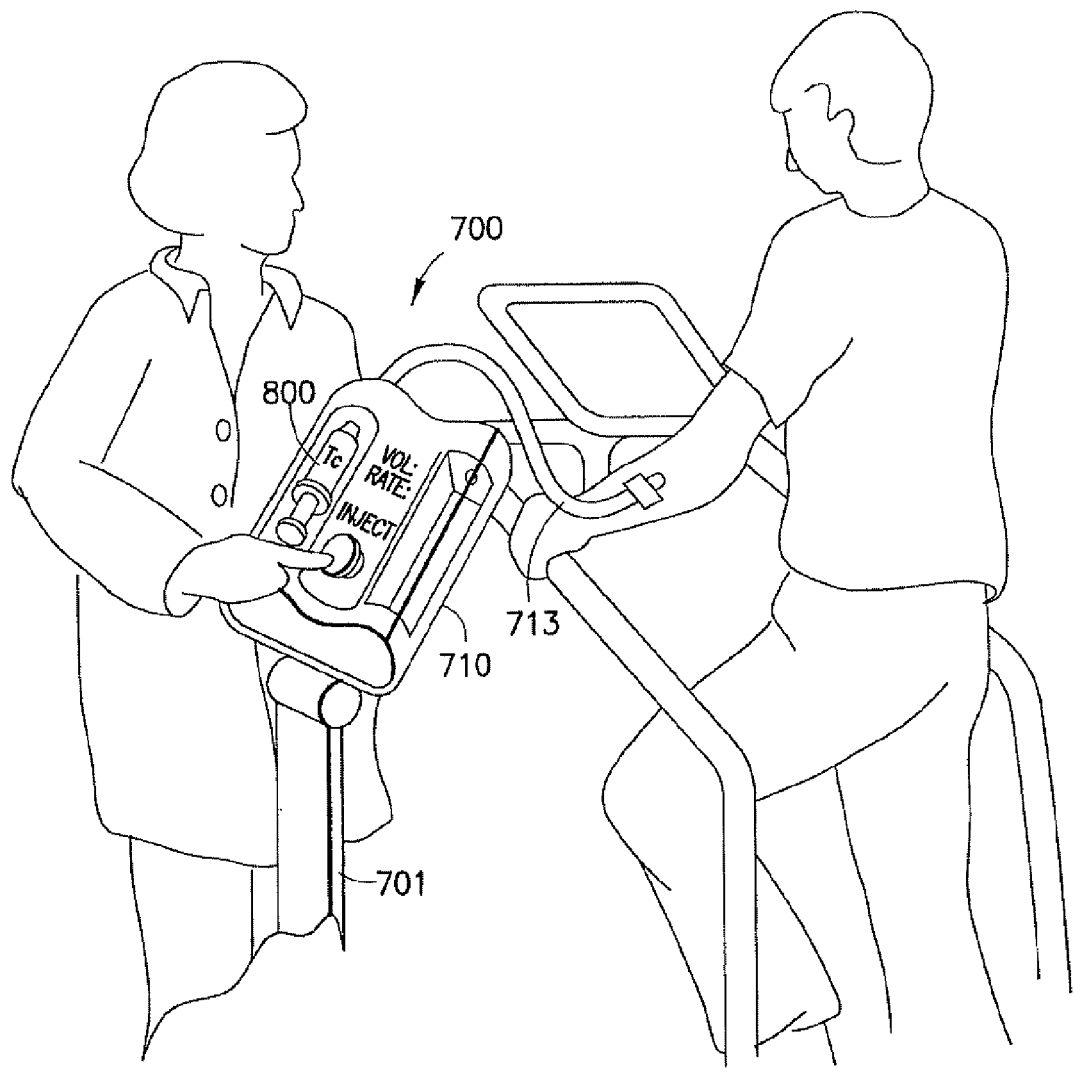
FIG. 36B is exterior or representative views of a portable implementation of the fluid delivery system of FIG. 36A.
Figure 37:
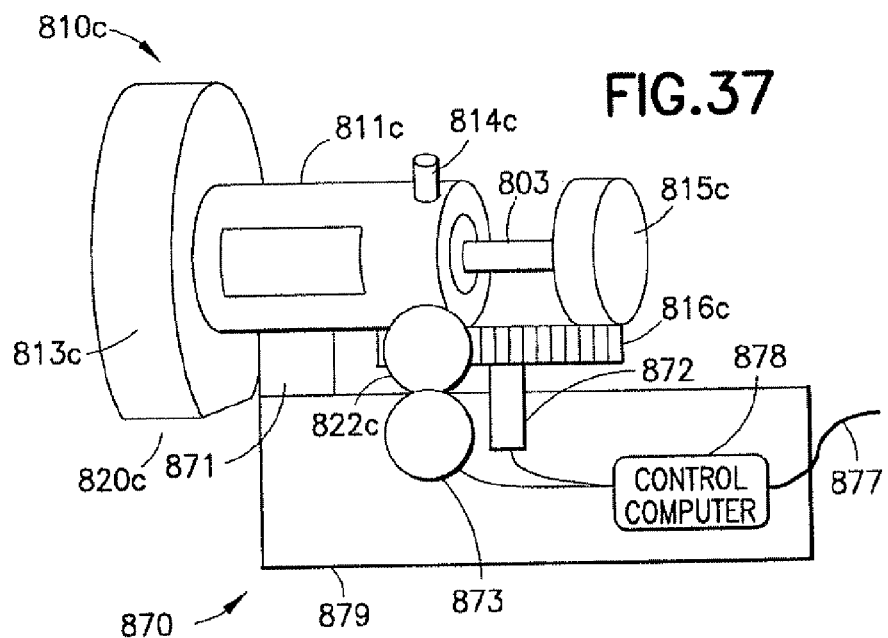
FIG. 37 is a schematic representation of a fluid delivery apparatus to which the syringe shield embodiment of FIG. 30 may be associated or engaged with an automatic power injection apparatus or similar apparatus.
Figure 38:
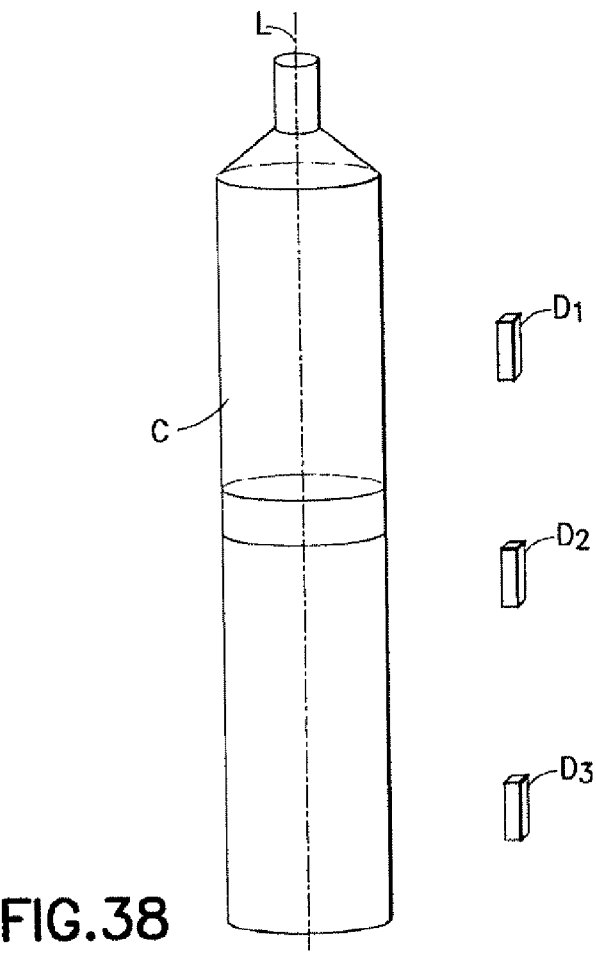
FIG. 38 is a schematic representation of a container with several associated dosimeters spaced at locations along the length of the container.

For the situations described in this disclosure wherein an injection dose is delivered to a patient at a site remote from its preparation, it may be necessary to overfill the syringe because the delay between filling and delivery may not be accurately known or controllable. In this case, it is useful to have a system that can adjust the dose in a syringe and like container without the need for a hot lab. If there is a dosimeter associated with the syringe shield, then all that is needed is a shielded waste container and the extra dose can be put into it. If there is not a dosimeter associated with the syringe shield, then a dose adjust device or system may be used. FIGS. 35-37 show several embodiments of such a device. FIG. 35A is a schematic representation of a dose adjuster 750, while FIGS. 35B-35C show exterior views of an exemplary implementation of dose adjuster 750 which may be utilized in practice. The components of dose adjuster 750 are a dosimeter including radiation sensor 751, control electronics 760, a user interface 761, shielding 752, a removable shielded waste container 754 which is separable and exchangeable at interface 753 and, optionally, a motor (not shown) to move the syringe piston rod 803 in radiopharmaceutical syringe 800. Because the dose adjuster 750 only needs to accommodate syringes up to a modest size, for example, 10 ml it need not be as big as normal laboratory dose calibrators. This means that for a given thickness of shielding, the weight is reduced in proportion to the square of the diameter reduction. In addition, an array of silicon diode dosimeters (as described previously) could be used as radiation sensor 751 and the dose calibrator can be made even smaller. In use, syringe 800 is inserted into the dose adjuster 750, either by manually removing it from its shield, or by having a telescoping shield as illustrated in FIG. 36C. The liquid is expelled a little bit at a time through opening 755 into waste container 754. To prevent spills there can be a rubber septum that is pierced by the syringe needle (not shown) or, preferably, there is an absorbent material in waste container 754 that traps the small amounts of liquid that will be injected. Because shielding is not absolute or 100%, radiation from the waste will be sensed to a modest degree by radiation sensor 751. This occurs continually, so before putting syringe 800 into the dose adjuster 750, control electronics 760 takes a measurement that represents only the dose from the nearby waste. This measurement is subtracted or tarred from the measurement of the dose in the syringe 800. The control electronics 760 may communicate the new adjusted dose to any of the many places mentioned elsewhere in this disclosure, for example, to an RFID or other device associated with syringe 800 or its syringe shield (not shown), to a hospital information system (HIS), to total or integrated systems 100, 100a described previously, etc. This communication may be done wirelessly or with wires, in real time or at some appropriate time. Labels can optionally be printed for various uses.

FIG. 35B shows waste container 754 being able to be removed from the front of dose adjuster 750. The syringe piston rod 803 of syringe 800 is not accessible by hand so this embodiment utilizes a motor to grip and drive the syringe piston rod 803. FIG. 35C uses a. telescoping syringe shield 712. This enables syringe 800 to be installed on dose adjuster 750 with syringe piston rod 803 extended so that the operator can express small volumes into the waste container 754 until the desired dose remains in syringe 800. Dose adjuster 750 may he operated as a standalone device for use in the current practice of nuclear medicine or it may be integrated into any of the various systems described herein. Once the syringe dose is adjusted to the right amount, it is ready for injection into a patient. The syringe 800 in a syringe shield 810 may be inserted directly into a fluid delivery system 700 comprising a syringe pump or, desirably, a power injector 710 as shown in FIG. 36A. In addition to radiopharmaceutical syringe 800, power injector 710 has a saline syringe 712 to flush the radiopharmaceutical from patient fluid line 713. Power injector 710 can control flow rate, volume, and pressure over time to deliver the optimum dose to the patient depending upon the study being performed. Various exemplary studies are discussed elsewhere in this disclosure and will not he repeated here. FIG. 36B shows a portable version of power injector 710 more akin to a syringe pump. All components associated with portable syringe pump 710 are similar to those shown in FIG. 36A. While syringe shield 810 is typically sufficient to shield the operator of fluid delivery system 700 from the radiopharmaceutical in syringe 800, fluid delivery in fluid delivery system 700 is generally very quick enough that the radiation dose from the radiopharmaceutical, while it is in the tubing comprising patient fluid 713, is relatively modest. Once the radiopharmaceutical is injected into the patient, the patient now becomes a significant source of radiation for the healthcare, workers around him or her. For this reason, vertical shields on wheels are sometimes employed so that the health care worker can be near the patient but be protected from radiation emanating from the patient.

In FIG. 36A, power injector 710 is mounted onto a wheeled shield stand 701 that incorporates a lead glass viewing port or window 702. Motors and control electronics are optionally contained in the body of power injector 710 which is supported on a mount 703 on the patient side of wheeled shield stand 701. Batteries can also be contained in the body of power injector 710 if desired. Syringe 800 is contained in syringe shield 810 and this assembled unit mounted to power injector 710 while a second syringe 712 forms a source of flush saline as indicated previously. Outputs from radiopharmaceutical syringe 800 and saline syringe 712 are desirably connected together and for association or fluid connection with patient fluid path 713. An operator user interface panel 715 is desirably provided on the operator side of wheeled shield stand 701 held by bracket 704 and connected to control electronics of power injector 710 via communications channel 714 or, optionally, via wireless communications. This arrangement along with an accompanying patient shield (not shown) is particularly advantageous when the fluid is being delivered over a length of time and the operator needs to stay near the patient or check on them at regular intervals. An operator can walk up to the operator's side of wheeled shield stand 701, check the injection status, and talk with the patient with a significantly reduced radiation dose to the operator. It is preferable that the fluid delivery system 700, and optionally all the various fluid manipulating devices and systems within this disclosure, also contain battery power for the fluid moving components and associated electronics so that fluid delivery system 700 can operate without an external power source.

As shown in FIG. 37, another benefit of, particularly, syringe shield 810c, discussed previously that incorporates a connection to syringe piston button 804 via shield button or disk 815c, is that this syringe shield 810c can easily mate with and be operated by a manual or an automatic injector or pump 870 with minimal radiation dose to the operator. A simple such embodiment is achieved by placing syringe 800 held in syringe shield 810c, for example, onto a motorized injector 870 by means of a mount 871 which is part of housing 879. Automatic injector or pump 870 has a drive mechanism 873, for example, a motor with gear reduction and a gear output that mates to thumb wheel 822 and a position sensor 872 that interacts with connecting rod 816c to sense the position of syringe piston rod 803. Drive mechanism 873 is controlled by an electronic control circuit or computer 878 that uses feedback from position sensor 872 and inputs 877 from a user interface or other system components to move the syringe piston rod 803 at the desired flow rate for the desired time. There can be a number of automatic pumps 870 that are at different places in the handling sequence of the radiopharmaceutical. The automatic pumps 870 can be battery-powered and small enough to be carried and held by hand, and can be used to replace manual filling, dose adjustment, and fluid delivery. As mentioned elsewhere, if computer-controlled electromechanical servo-pumps are used to deliver the radiopharmaceutical or radiopharmaceuticals because of their accuracy and control of motion, it is possible for almost all procedures on human patients to be accommodated by a 10 ml syringe. This standardization can lead to standardization among other equipment such as dose calibrators, syringe shields, syringe pumps, and much of the other equipment used in cardiac stress test procedures and similar nuclear-related procedures. This version of syringe shield 810c and a suitable mating injector apparatus 870 as shown in FIG. 37 are also applicable for use as patient administration module 160 of FIGS. 3-4.

Because transmission of radioactivity through shielding is an exponential function of the thickness of the shielding, the thickness of any shielding in any particular design is a function of the time the operator or others will spend in proximity to the device, the strength of the source, the type and energy of the radiation, and the effect of the weight of the shielding. The making of these tradeoffs is well-known to those skilled in the health physics and nuclear medicine fields. Thus, the shielding thicknesses of these embodiments are either not specifically constrained, or if they are given, can be appropriately adjusted for the specific needs of the application and are discussed for example only.

The term "pump" as used in the disclosure is intended to include all means of causing a controlled fluid flow, including controlled pumps or pressure sources and regulators, for example, peristaltic pumps, gear pumps, syringe pumps, electrokinetic pumps, gravity, compressed gas, controlled gas evolving devices, spring pumps, centripetal pumps or any system which does not require continuing human exertion of motive force when the fluid is flowing, although hand activated pumps are equally suitable in many of the foregoing embodiments.

The specific radiopharmaceuticals or drugs mentioned in this disclosure or other pharmaceuticals as desired can be included in or associated with ultrasound bubbles. The systems described in the foregoing are available to deliver such bubbles to the region of interest and then ultrasound energy can be used to destroy the bubbles and promote the delivery of the associated radiopharmaceutical, drug, or other pharmaceutical to the intended tissue. The uses of ultrasound bubbles to deliver and release a drug or pharmaceutical to a region of interest is disclosed in U.S. Pat. No. 6,397,098, assigned to the assignee of this disclosure, the disclosure of which is incorporated herein by reference.

Another aspect described hereinafter relates to systems and methods and associated components or devices for more accurately determining a radiopharmaceutical dose administered to a patient by relying on a time factor. Broadly contemplated herein is the administration of a dose on the basis of an elapsed time from when a dose was last accurately measured, for example, at the time of filling into a container to when it is injected into a patient. The foregoing concept is discussed in connection with RS device 1002 discussed previously in connection with system 1000. In system 1000, RS device 1002 is initially associated with fill station 1010 as a bulk radiopharmaceutical filing station and configured to hold RP container 1004 to be filled from chemistry unit 1008. RP container 1004 is pre-located in RS device as described previously. As noted previously, device and drug data recorder 1028 has an identification arrangement ("ID") for uniquely identifying RS device 1002 and the contents of RP container 1004 and, desirably, RP container 1004 itself. Device and drug data recorder 1028 further records radiation dose information via dosimeter 1024 and dosimeter control 1026 so that this information is available to fill system control 1016 and displayable on fill system user interface 1018. Accordingly, RS device 1002 has the ability to read, ascertain, or measure the radiation dose (radioactivity level) present in RP container 1004. Furthermore, device and drug data recorder 1028 desirably includes a clock ("clock 1") which establishes a time-point at which the RP container 1004 is filled with radiopharmaceutical. Accordingly, when RP container 1004 is filled at fill system 1010, a radiation dose is recorded along with the time-point of filling. This information is then available when the RS device 1002 is transported to fluid delivery system 1030. This version of radiopharmaceutical system 1000 and RS device 1002 therein are also applicable for use as or in patient administration module 160 of FIGS. 3-4.

Once transported to the fluid delivery system 1030, the dose in the RP container 1004 may be calculated based on the time-point of filing associated with RP container 1004 and the known half-life of its contents. This calculation may be done by fluid delivery system control 1036 and may take into account the time at which the contents of RP container 1004 are to be administered to a patient. Thus, a calculation is made which takes into account two distinct time-points, the time of filling and the time at which it is desired to ascertain the radiation dose again, such as when it is to be administered to a patient and the known half-life of the radiopharmaceutical, so as to clearly establish the degree to which the radiopharmaceutical may have decayed and thus lost potency.

In another embodiment, the radiopharmaceutical dose is measured at a time of filling one or more "dose" containers, similar to RP container 1004 discussed previously. At such a time, both the time-point and radiation dose are recorded and associated with ID information on the dose container. An associated transport device or station, for example, a cart or transport container (i.e., pig), has a clock that is synchronized with a clock associated with the filling station clock so it will present a similar time base as the filling station. More particularly, the radiopharmaceutical dose is preferably measured at a single time of filling one or more dose containers. At such a time, both the time-point and radiation dose are recorded and associated with ID information on a dose container. The transport container, cart, or other transport conveyance has a clock which is synchronized with a clock associated with the filling station clock so it will present a similar time base as the filling station.

As per convention, a bulk radiopharmaceutical filing station is configured to hold a single or multiple dose containers to be filled from a bulk supply. The dose container is then placed in a shielded transport container (i.e., pig), cart, or other conveyance for transport to a patient dose administration system. Desirably, the dose container has an ID arrangement, such as a barcode or RFID, that can easily be read by suitable apparatus such as a reader r1 at the filling station, and the filling station has another data collection arrangement r2 for reading, ascertaining, or measuring the radiation dose (radioactivity level) present in the dose container. Furthermore, the filling station also preferably includes a clock ("clock 1") which establishes a time-point at which the dose container is filled with radiopharmaceutical.

When the dose container is filled at the filling station, the radiation dose is recorded along with the time-point of filling. The transport container will include a clock ("clock 2") which is synchronized with clock 1. Upon being loaded into the transport container, another reader (r3) may read the ID information of the transport container or this may be read by a reader present at a patient dose administration system. The ID information is also preferably read immediately before radiopharmaceutical is administered to a patient.

A suitable communication link is provided between the filling station and transport container, for instance, via wireless communication between antennae at the filling station and transport container ("ant. 1" and "ant. 2", respectively). This communication link permits data to be exchanged in a manner to readily ascertain the radiation dose administered to a patient. As such, this embodiment serves to obviate the need to directly measure a dose of radiopharmaceutical administered to a patient when it is being administered to the patient. Once at a patient dose administration system, the dose in the dose container is automatically and reliably calculated without human intervention and thus possibly without error based on the time associated with the dose container and the known half-life of its contents. Thus, a calculation is made which takes into account two distinct time-points, the time of filling and the time at which it is desired to ascertain the radiation dose again, such as when it is to be administered to a patient, and the known half-life of the radiopharmaceutical so as to clearly establish the degree to which the radiopharmaceutical may have decayed and thus lost potency. The filling station and transport container clocks, clocks 1 and 2, can reference a wireless time standard such as those based at the United States Time Service of the United States Naval Observatory or the National Institute of Science and Technology (NIST). If the system is to be employed outside of the United States, similar time standards (such as governmental time standards) in other countries can also be employed. Or, a single clock, for example, a digital quartz watch, may be associated with and transported with RP container 1004 to obviate the need for synchronization of multiple clocks.

At times, it may be desirable to add a non-radioactive diluent to the dose container such that the total volume in the dose container comprises the volume of the radiopharmaceutical plus that of the added diluent. If this is the case, the radioactivity of the contents of the dose container can be measured after it has been diluted. The ID information on the dose container further provides information on the type of radionuclide that comprises the radiopharmaceutical. Ultimately, the half-life of the radiopharmaceutical can be obtained by a look-up table in order to help calculate the radioactive decay between the two time-points mentioned previously. Alternatively, such information on the radiopharmaceutical can be entered by an operator at any suitable time.

A data repository may also be provided for recording all pertinent data. The repository could be an additional component remote from the filling station or transport container, or could be integral to the filling station or transport container. Again, the recorded information can include the time the dose container is filled, the level of radioactivity contained in the dose container immediately after the dose container is filled, the name of the radionuclide of the radiopharmaceutical or its decay half-life, and the identification information of that portable dose container recorded from the ID arrangement of the dose container. To the extent that a data repository is remote with respect to either the filling station or transport container or both, a suitable communication link (such as the wireless radio frequency link discussed hereinabove or an alternative arrangement such as an optical/infrared or wired communications link) could be employed to exchange data with the data repository. All such data exchanged can be encrypted to secure the data against unauthorized reading, and the repository itself can be secured against deliberate or unintended alteration.

The data repository can optionally be expanded is scope through various data communications devices and systems to include all data related to or generated from the medical procedures assisted by the devices and systems or using the methods of this disclosure. This can include retrieving, utilizing and storing information about, for example, the patient, patient scheduling, dosing, timing, and results of the study. It can optionally involve successively larger scopes of communication, including that among many centers for benchmarking or procedure improvement, as disclosed United States Patent Application Publication No. 2003/0212707 entitled "System and Method for Automated Benchmarking for the Recognition of Best Medical Practices and Products and for Establishing Standards for Medical Procedures", incorporated herein by reference.

GPS (Global Positioning System) receivers and transponders (either cell phone, satellite, or other means) can be incorporated in various components of this disclosure. For example, incorporating them into RS device 1002 described previously could allow tracking of the doses and possible rerouting while in transit. It could also better enable JIT (Just in Time) inventory management practices. Even within a patient treatment facility, knowing where a dose is and when it will arrive can improve patient throughput and equipment utilization. Providing a GPS device to a patient could allow the hospital to track the patient, and if it is a cell phone with limited capability, to even call the patient and tell them that they need to report for their procedure. Alternatively, a device similar to the RF paging systems, an example of which is described in U.S. Pat. No. 6,542,751 incorporated herein by reference, is used in busy restaurants and can be further provided with GPS systems to track the patients and then issue an "alarm" to indicate when the patient should return to the desk for further instructions.

The sophistication, integration, and flexibility of the devices, systems, and methods of this disclosure enable a flexibility and sophistication of procedures that is impossible or very difficult without the use of the various embodiments described hereinabove. An exemplary improvement mentioned in this disclosure includes the controlled dosing with "hot" and "cold" pharmaceuticals. A number of exemplary procedures will now be explained. In regards to FDG, the study is not normally done if blood glucose level is too high. An example threshold is 100 mg/dl. If blood sugar level is too high, it competes with FDG for admission to cells and too little FDG is taken up. Following this line of reasoning, for sequential quantitative FDG studies, it is desirable that a sufficiently similar blood glucose level be achieved for subsequent studies. To achieve this, patient monitor 160 in integrated system 100 could actively measure blood glucose, or a blood glucose reading could be entered into the integrated system controller through user interface 115. This information can then be used to determine an infusion of a drug, for example, sugar water, insulin, or some other drug that affects blood sugar level from fluid handling system 150. When blood glucose level is at the desired level, the FDG can be injected for the study. This reduces this source of variability in current medical practice. It can also facilitate a new procedure similar to that of competitive receptor studies in the brain. FDG can be injected and the imaging started. Then, after an appropriate amount of time has elapsed, glucose can be injected, and the effect on FDG uptake can be assessed. Optionally, at the same time, patient monitor 160 can measure the actual blood glucose level. This competitive uptake can provide additional information about the physiology of the cells being studied in the patient.

If a specific time course of radiopharmaceutical concentration in the blood or in a tissue is desired, and initial flow profile can be determined using the models of H. Schwilden disclosed in "A General Method for calculating the Dosage Scheme in Linear Pharmacokinetics" published in the European Journal of Clinical Pharmacology, (1981) 20:379-386, and incorporated herein by reference. With the fluid handling system 150 integrated with the imager 130, data concerning uptake in an area of measurement or an area of interest can be used to adjust or optimize the injection during the injection, if the injection duration is long enough for this to be effective. Details of this process are discussed in U.S. Pat. No. 5,840,026, incorporated herein by reference. It is also possible, as discussed in U.S. Pat. No. 5,840,026 to use an appropriate detector (radiation detector in this case) on some other part of the body, such as an ear lobe or a finger to sense the approximate arrival time and level over time of the radiopharmaceutical. Time course measurements of concentration in a tissue can be used, for example, for functional imaging or for physiological monitoring of a specific region of interest. The level at one area or region of the patient can be used to trigger the beginning of the scanning of the region of interest. Or, alternatively, the scanning can be triggered or synchronized to another measurement of the patient monitor, for example, ECG, respiration, EEG, or a sensation being perceived by the patient. Additionally, fluid handling system 150 may contain a pharmaceutical and its antagonist drug so that if, because of physiological delays, too much of the first drug is injected, patient monitor 160 can detect the overreaction and inject some of the antagonist to cancel some of the effect.

Because of the increased use of nuclear medicine, it is optionally preferable that integrated system 100 measure the radioactivity of the patient before the injection, to make sure that there is no effect from a previous study that might confound the current measurements. This could be done with the imager 130 or with a separate hand held radiation detector. For short lived isotopes, this is not a problem. This strategy could also be employed, preferably using a handheld radiation detector or camera to assess concentration of the isotope in the liver and the bladder and thus readiness for scanning with main imager 130.

While numerous embodiments have been disclosed with certain features, this is primarily for clarity of explanation and understanding of these features and the example synergy and benefits achieved by the specific integrations discussed. It will be recognized by those skilled in the art that other combinations or integrations are possible, and even desirable, but cannot all be described herein. For example, blood sampling discussed in relation to the concepts of FIG. 7 can be included in the total or integrated system of FIG. 2A. The disclosed in-line dosimeters or other activity measurement devices may be used to assess the activity in such a sample. Likewise, a system can be envisioned that does not require every feature for it to be useful for specific applications. For example, the integrated system of FIG. 2A would be very useful for many medical procedures without a way to provide a stimulus to the patient. While the devices, systems, and methods of this disclosure have been described in relation to medical procedures on humans and on animals, they can be used on all biological systems. Accordingly, the foregoing description is intended to be illustrative rather than restrictive. The inventions described hereinabove are defined by the appended claims and all changes to the invention that fall within the meaning and the range of equivalency of the claims are to be embraced within their scope.

The invention claimed is:

1. A hazardous fluid handling system comprising:
   a pump;
   a pump control device electronically linked to the pump;

a user interface wirelessly coupled to the pump control device;

a radiation shielded internal chamber disposed within a housing and configured to hold a container having a radioactive fluid contained therein and having a known internal geometry;

at least two radioactivity detectors positioned within the shielded internal chamber in operational proximity to the radioactive fluid in the container; and a dosimeter control device electronically coupled to each of the at least two radioactivity detectors, wherein the dosimeter control device is operational for determining information on a fill volume of the radioactive fluid in the container based on individual measurements received from the at least two radioactivity detectors, and wherein the dosimeter control device is configured to use the individual measurements received from the at least two radioactivity detectors for determining error information comprising at least one of a presence of bubbles in the container and a presence of spills or leaks of the radioactive fluid from the container.

2. The hazardous fluid handling system of claim 1, wherein the dosimeter control device is electronically linked to the pump control device.

3. The hazardous fluid handling system of claim 1, further comprising a data recording device electronically linked to the dosimeter control device.

4. The hazardous fluid handling system of claim 1, further comprising a communications interface electronically linked to the pump control device.

5. The hazardous fluid handling system of claim 4, wherein the communications interface is configured to wirelessly link to an information network.

6. The hazardous fluid handling system of claim 1, further comprising a fluid path in fluid communication with the pump.

7. The hazardous fluid handling system of claim 1, wherein the user interface is a handheld user interface wirelessly coupled to the pump control device.

8. The hazardous fluid handling system of claim 1, wherein the hazardous fluid handling system is integrated into a patient support platform.

9. The hazardous fluid handling system of claim 8, wherein the patient support platform comprises:

a patient stimulus apparatus;

an imager proximate the patient support platform;

a radiopharmaceutical fluid delivery system for infusing the radiopharmaceutical fluid into a patient;

a patient monitor to be associated with the patient; and an integrated system controller operably associated with the patient stimulus apparatus, the imager, the radiopharmaceutical fluid delivery system, and the patient monitor.

10. The hazardous fluid handling system of claim 1, wherein the dosimeter control device receives a signal from each of the at least two radioactivity detectors and is capable of determining an activity of the radioactive fluid in the container.

11. The hazardous fluid handling system of claim 1, wherein each of the at least two radioactivity detectors are positioned at a different vertical location relative to the shielded internal chamber.

12. The hazardous fluid handling system of claim 1, further comprising at least one position sensor, wherein the dosimeter control device is operational for determining the fill volume and one or more additional property of the system based on individual measurements received from the at least two radioactivity detectors and the at least one position sensor.

13. A hazardous fluid handling system comprising:

a pump;

a pump control device electronically linked to the pump;

a user interface wirelessly coupled to the pump control device;

a radiation shielded internal chamber disposed within a housing and configured to hold a container having a radioactive fluid contained therein and having a known internal geometry;

at least one radioactivity detector positioned within the shielded internal chamber in operational proximity to detect radiation emitted by the radioactive fluid in the container;

a position sensor; and a dosimeter control device electronically coupled with the at least one radioactivity detector and the position sensor, wherein the dosimeter control device is operational for determining an activity of the radioactive fluid in the container based on measurements received from the at least one radioactivity detector and the position sensor, and wherein the dosimeter control device is configured to use individual measurements received from the at least one radioactivity detector and the position sensor for determining error information comprising at least one of a presence of bubbles in the container and a presence of spills or leaks of the radioactive fluid from the container.

14. The hazardous fluid handling system of claim 13, further comprising a data recording device electronically linked to the dosimeter control device.

15. The hazardous fluid handling system of claim 13, wherein the dosimeter control device receives a signal from at least two radioactivity detectors and the position sensor and is capable of determining the activity of the radioactive fluid in the container and at least one additional property of the system.

16. The hazardous fluid handling system of claim 13, wherein the dosimeter control device is electronically linked to the pump control device.

17. The hazardous fluid handling system of claim 16, further comprising a communications interface electronically linked to the pump control device and wirelessly linked to an information network.

18. The hazardous fluid handling system of claim 13, wherein the user interface is a handheld user interface wirelessly coupled to the pump control device.

19. The hazardous fluid handling system of claim 13, wherein the hazardous fluid handling system is integrated into a patient support platform.

20. The hazardous fluid handling system of claim 19, wherein the patient support platform comprises:

a patient stimulus apparatus;

an imager proximate the patient support platform;

a radiopharmaceutical fluid delivery system for infusing the radiopharmaceutical fluid into a patient;

a patient monitor to be associated with the patient; and an integrated system controller operably associated with the patient stimulus apparatus, the imager, the radiopharmaceutical fluid delivery system, and the patient monitor.

* * * * *

UNITED STATES PATENT AND TRADEMARK OFFICE
CERTIFICATE OF CORRECTION

PATENT NO. : 10,016,618 B2  
APPLICATION NO. : 15/142000  
DATED : July 10, 2018  
INVENTOR(S) : Hirschman et al.

Page 1 of 1

It is certified that error appears in the above-identified patent and that said Letters Patent is hereby corrected as shown below:

On the Title Page
In Item (72), under "Inventors", in Column 1, Line 7, delete "Ford City, PA" and insert -- Coppell, TX --, therefor.

In the Drawings
In Fig. 16, Sheet 18 of 35, delete Tag "1018'a" and insert Tag -- 1018a' --, therefor.
In Fig. 16, Sheet 18 of 35, delete Tag "1018'b" and insert Tag -- 1018b' --, therefor.
In Fig. 16, Sheet 18 of 35, delete Tag "1018'a" and insert Tag -- 1018a' --, therefor.
In Fig. 16, Sheet 18 of 35, delete Tag "1018'b" and insert Tag -- 1018b' --, therefor.

In the Specification
In Column 1, Line 9, delete "Divisional" and insert -- Continuation --, therefor.
In Column 11, Line 2, delete "form" and insert -- from --, therefor.
In Column 20, Line 25, delete "PACS (Picture Archiving and Storage)" and insert -- PACS (Picture Archiving and Communication System) --, therefor.
In Column 36, Line 61, delete "elutations" and insert -- elutions --, therefor.

Signed and Sealed this
Twenty-third Day of October, 2018

Andrei Iancu
*Director of the United States Patent and Trademark Office*